United States Patent
Inoue et al.

(10) Patent No.: US 9,265,235 B2
(45) Date of Patent: Feb. 23, 2016

(54) ACCIDENTAL INGESTION DETECTION APPARATUS, ACCIDENTAL INGESTION DETECTION SYSTEM, AND ACCIDENTAL INGESTION DETECTION METHOD

(71) Applicant: Panasonic Intellectual Property Corporation of America, Torrance, CA (US)

(72) Inventors: Ryuji Inoue, Osaka (JP); Yoshihiro Kojima, Hyogo (JP); Toru Tanigawa, Osaka (JP)

(73) Assignee: Panasonic Intellectual Property Corporation of America, Torrance, CA (US)

(*) Notice: Subject to any disclaimer, the term of this patent is extended or adjusted under 35 U.S.C. 154(b) by 0 days.

(21) Appl. No.: 14/251,969

(22) Filed: Apr. 14, 2014

(65) Prior Publication Data

US 2014/0306827 A1     Oct. 16, 2014

(30) Foreign Application Priority Data

Apr. 16, 2013 (JP) .................... 2013-085346

(51) Int. Cl.
- *G08B 23/00* (2006.01)
- *A01K 29/00* (2006.01)
- *A61D 1/12* (2006.01)

(52) U.S. Cl.
CPC ............. *A01K 29/005* (2013.01); *A61D 1/12* (2013.01)

(58) Field of Classification Search
CPC ........... A61K 48/0041; A61K 48/005; A61K 9/1647; A61K 9/5153; A61K 31/7048; A61K 38/177; A61K 48/00; A61K 48/0025; A61K 47/42; A61K 47/38; A61K 47/48784; A61K 9/0056; A61K 9/06; A01N 59/00
USPC .......... 340/573.3, 573.1, 572.1–572.9, 568.1, 340/571, 573.2
See application file for complete search history.

(56) References Cited

U.S. PATENT DOCUMENTS

| | | | |
|---|---|---|---|
| 2005/0131281 A1* | 6/2005 | Ayer et al. ...................... 600/302 |
| 2006/0064037 A1* | 3/2006 | Shalon et al. .................. 600/586 |
| 2010/0162960 A1* | 7/2010 | Moon ......................... 119/51.02 |
| 2011/0111108 A1* | 5/2011 | Craig et al. ..................... 426/442 |
| 2012/0236690 A1* | 9/2012 | Rader ............................. 368/10 |
| 2013/0104796 A1* | 5/2013 | Bhat et al. ......................... 116/2 |

FOREIGN PATENT DOCUMENTS

| | | |
|---|---|---|
| JP | 2012-70671 | 4/2012 |
| JP | 2013-17694 | 1/2013 |

* cited by examiner

*Primary Examiner* — Daniel Previl
(74) *Attorney, Agent, or Firm* — Wenderoth, Lind & Ponack, L.L.P.

(57) ABSTRACT

An accidental ingestion detecting apparatus according to the present disclosure includes: a swallowing sensing unit which senses swallowing by an animal; a swallowing detecting unit which detects swallowing based on sensing data outputted by the swallowing sensing unit and which outputs swallowing information that is information related to the swallowing; a feeding information inputting unit which accepts input of information related to feeding of the animal and which outputs the information as feeding information; and an accidental ingestion determining unit which determines accidental ingestion by the animal, wherein the accidental ingestion determining unit determines accidental ingestion by the animal based on date/time information included in the swallowing information and date/time information included in the feeding information.

20 Claims, 40 Drawing Sheets

FIG. 4

EXAMPLE OF SWALLOWING
INFORMATION

| | |
|---|---|
| 401 | 13:48:32 ON MARCH 18, 2013 |
| 402 | 13:49:05 ON MARCH 18, 2013 |
| | ... |
| 403 | 14:08:18 ON MARCH 18, 2013 |

FIG. 5

EXAMPLE OF FEEDING
INFORMATION

EXAMPLE OF ACCIDENTAL INGESTION
NOTIFICATION INFORMATION

EXAMPLE OF CONFIRMATION
RESULT INFORMATION

1401

| 14:08:18 ON MARCH 18, 2013 | ACCIDENTAL INGESTION |

FIG. 15

EXAMPLE OF CONFIRMATION
RESULT INFORMATION TABLE

| CONFIRMED SWALLOWING DATE/TIME | CONFIRMATION RESULT |
|---|---|
| 15:12:06 ON MARCH 17, 2013 | NOT ACCIDENTAL INGESTION |
| 14:08:18 ON MARCH 18, 2013 | ACCIDENTAL INGESTION |
| 19:45:52 ON MARCH 21, 2013 | NOT ACCIDENTAL INGESTION |

FIG. 19

EXAMPLE OF ACCIDENTAL INGESTION
NOTIFICATION INFORMATION

1901

| 14:08:18 ON MARCH 18, 2013 | A DEGREES B MINUTES 32 SECONDS NORTH, C DEGREES D MINUTES 37 SECONDS EAST |
|---|---|

FIG. 20

EXAMPLE OF CONFIRMATION
RESULT INFORMATION

2001

| 14:08:18 ON MARCH 18, 2013 | A DEGREES B MINUTES 32 SECONDS NORTH, C DEGREES D MINUTES 37 SECONDS EAST | ACCIDENTAL INGESTION |

FIG. 21

EXAMPLE OF CONFIRMATION
RESULT INFORMATION TABLE

| CONFIRMED SWALLOWING DATE/TIME | CONFIRMED SWALLOWING POSITION | CONFIRMATION RESULT |
|---|---|---|
| 14:08:18 ON MARCH 18, 2013 | A DEGREES B MINUTES 32 SECONDS NORTH, C DEGREES D MINUTES 37 SECONDS EAST | ACCIDENTAL INGESTION |
| 19:45:52 ON MARCH 21, 2013 | A DEGREES E MINUTES 15 SECONDS NORTH, C DEGREES F MINUTES 24 SECONDS EAST | NOT ACCIDENTAL INGESTION |

2700

A DEGREES B MINUTES 32.08 SECONDS NORTH,
C DEGREES D MINUTES 37.06 SECONDS EAST

2702

A DEGREES B MINUTES 32.51 SECONDS NORTH,
C DEGREES D MINUTES 37.05 SECONDS EAST

2700

A DEGREES B MINUTES 32.08 SECONDS NORTH,
C DEGREES D MINUTES 37.06 SECONDS EAST

2702

A DEGREES B MINUTES 32.09 SECONDS NORTH,
C DEGREES D MINUTES 37.05 SECONDS EAST

EXAMPLE OF ACCIDENTAL INGESTION
NOTIFICATION INFORMATION

FIG. 36

EXAMPLE OF IMAGE
FEATURE QUANTITY TABLE

| FEATURE QUANTITY ID | FEATURE QUANTITY | TYPE | NAME |
|---|---|---|---|
| F0001 | (21, 175, ···) | PERSON | TARO |
| F0002 | (124, 56, ···) | FOOD | DRY FOOD |

3601 / 3602 / 3603 / 3604

ACCIDENTAL INGESTION DETECTION APPARATUS, ACCIDENTAL INGESTION DETECTION SYSTEM, AND ACCIDENTAL INGESTION DETECTION METHOD

BACKGROUND OF THE INVENTION

1. Field of the Invention

The present disclosure relates to an apparatus, a system, and a method for detecting accidental ingestion by animals.

2. Description of the Related Art

There has been a recent increase in the number of pet owners that consider an animal bred at home to be a "member of the family" instead of a simple pet. Such owners are extremely attentive to a state of health of the animal being bred, and assess the state of health by checking the amount of food, the amount and state of excrement, hair condition, skin condition, and the like.

Meanwhile, incidents of accidental ingestion where an animal inadvertently swallows an object other than food continue to occur. An owner must be careful not to leave objects that can be swallowed by an animal within a range of action of the animal. However, no matter how careful the owner may be, there is always a chance that the animal may seek out and swallow an object that the owner had hidden in a closet or that the animal may break an object in the owner's absence and swallow one of the fragments.

When an accidental ingestion by an animal occurs, depending on what had been swallowed, the animal may experience gastric or intestinal obstruction which may cause violent vomiting or appetite loss. Since delayed medical attention may prove fatal, the owner must immediately take the animal to a veterinary upon realizing that accidental ingestion has occurred. However, since accidental ingestion by an animal is not always immediately manifested as a symptom, the owner often fails to realize that accidental ingestion by the animal has occurred for a certain amount of time after the accidental ingestion had taken place.

Conventionally, there is a system that determines whether or not a bolus has passed through the esophagus by measuring and analyzing a sound of laryngeal action that accompanies a swallowing action of a measurement subject for the purpose of measuring a swallowing function of a patient with a swallowing (swallowing of food or a fluid) disorder (for example, refer to Japanese Patent Application Laid-open No. 2013-017694).

In addition, there is a system which outputs stimuli (a scent or a sound) that an animal dislikes upon detecting an object approaching the mouth of the animal for the purpose of restricting feeding of the animal (for example, refer to Japanese Patent Application Laid-open No. 2012-070671).

However, the configuration of the prior art requires further improvements.

SUMMARY OF THE INVENTION

An accidental ingestion detecting apparatus according to an aspect of the present disclosure includes: a swallowing sensing unit which senses swallowing by an animal; a swallowing detecting unit which detects swallowing based on sensing data outputted by the swallowing sensing unit and which outputs swallowing information that is information related to the swallowing; a feeding information inputting unit which accepts input of information related to feeding of the animal and which outputs the information as feeding information; and an accidental ingestion determining unit which determines accidental ingestion by the animal, wherein the accidental ingestion determining unit determines accidental ingestion by the animal based on date/time information included in the swallowing information and date/time information included in the feeding information.

The inclusive or specific aspect may be realized by a system, a method, an integrated circuit, a computer program, a computer-readable storage medium such as a CD-ROM, or any combination of a system, a method, an integrated circuit, a computer program, and a storage medium.

According to the aspect described above, further improvements can be achieved.

BRIEF DESCRIPTION OF THE DRAWINGS

FIG. 4 is a diagram showing an example of swallowing information;

FIG. 5 is a diagram showing an example of feeding information;

FIG. 9 is a diagram showing an example of accidental ingestion notification information according to Embodiment 2;

FIG. 14 is a diagram showing an example of confirmation result information according to Embodiment 3;

FIG. 15 is a diagram showing an example of a confirmation result information table according to Embodiment 3;

FIG. 19 is a diagram showing an example of accidental ingestion notification information according to Embodiment 4;

FIG. 20 is a diagram showing an example of confirmation result information according to Embodiment 4;

FIG. 21 is a diagram showing an example of a confirmation result information table according to Embodiment 4;

FIG. 36 is a diagram showing an example of an image feature quantity table;

DESCRIPTION OF THE PREFERRED EMBODIMENTS

Findings Underlying Present Invention

Figure 1:
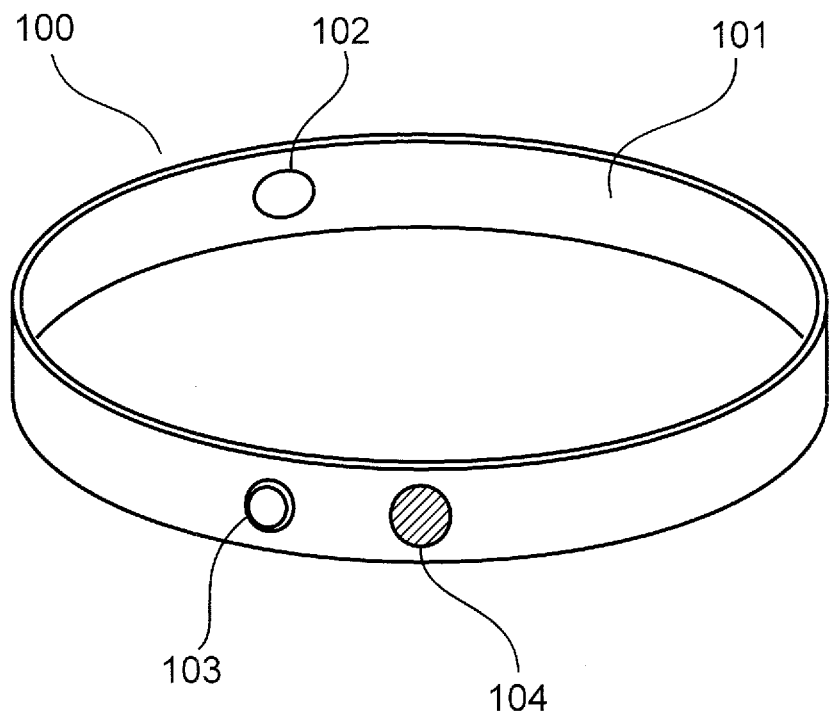
FIG. 1 is a diagram showing an appearance of an accidental ingestion detecting apparatus according to Embodiment 1.

As described earlier, patent document 1 discloses a technique for determining whether or not a bolus has passed through the esophagus by measuring and analyzing a sound of laryngeal action that accompanies a swallowing action of a measurement subject.

However, even if the technique enables detection of the passage of some kind of object through the esophagus of an animal, the technique is unable to determine whether or not the object is food given by an owner.

In addition, patent document 2 discloses a technique for outputting stimuli (a scent or a sound) that an animal dislikes upon detecting an object approaching the mouth of the animal.

However, this technique is intended to prevent an animal from putting an object that is not permitted as food into its mouth. Therefore, even if the animal grows accustomed to or manages to withstand the stimuli and swallows the object, the swallowing of the object cannot be detected.

In order to solve such problems, an accidental ingestion detecting apparatus according to an aspect of the present disclosure includes: a swallowing sensing unit that senses swallowing by an animal; a swallowing detecting unit which detects swallowing based on sensing data outputted by the swallowing sensing unit and which outputs swallowing information that is information related to the swallowing; a feeding information inputting unit which accepts input of information related to feeding of the animal and which outputs the information as feeding information; and an accidental ingestion determining unit that determines accidental ingestion by the animal, wherein the accidental ingestion determining unit determines accidental ingestion by the animal based on date/time information included in the swallowing information and date/time information included in the feeding information.

According to such a configuration, accidental ingestion by an animal can be detected by comparing the date/time at which swallowing by the animal is detected with the date/time included in information which is related to feeding of the animal and which is inputted by an owner.

In addition, for example, the accidental ingestion detecting apparatus may further include a notifying unit which notifies a user that accidental ingestion by the animal has occurred when the accidental ingestion determining unit determines that accidental ingestion by the animal has occurred.

According to such a configuration, detection of accidental ingestion by the animal by the accidental ingestion detecting apparatus can be notified to the owner.

Furthermore, for example, the notifying unit may issue a notification using at least one of light, sound, text, and images.

According to such a configuration, the fact that accidental ingestion has occurred can be visually, audibly, or perceptually notified to the owner.

In addition, an accidental ingestion detecting system according to another aspect of the present disclosure is an accidental ingestion detecting system including an accidental ingestion detecting apparatus that detects accidental ingestion by an animal and a feeding information inputting apparatus that accepts information related to feeding of the animal and that outputs the information as feeding information, wherein the accidental ingestion detecting apparatus includes a swallowing sensing unit which senses swallowing by an animal, a swallowing detecting unit which detects swallowing based on sensing data outputted by the swallowing sensing unit and which outputs first swallowing information that is information related to the swallowing, an accidental ingestion determining unit which determines accidental ingestion by the animal, and a communicating unit which performs communication with the feeding information inputting apparatus, and the accidental ingestion determining unit determines accidental ingestion by the animal based on date/time information included in the first swallowing information and date/time information included in feeding information, which is inputted using the feeding information inputting apparatus and which is included in feeding information obtained through the communicating unit.

According to such a configuration, accidental ingestion by an animal can be detected by comparing the date/time at which swallowing by the animal is detected with the date/time included in information which is related to feeding of the animal and which is separately inputted by an owner or inputted using the feeding information inputting apparatus.

Furthermore, for example, the accidental ingestion detecting apparatus may further include a first notifying unit which notifies a user that accidental ingestion by the animal has occurred when the accidental ingestion determining unit determines that accidental ingestion by the animal has occurred.

According to such a configuration, the accidental ingestion detecting apparatus itself can notify the owner that accidental ingestion by the animal has occurred.

In addition, for example, the accidental ingestion detecting system may further include a second notifying unit that is independent of the accidental ingestion detecting apparatus, wherein when the accidental ingestion determining unit determines that accidental ingestion by the animal has occurred, the second notifying unit may communicate with a communicating unit included in the accidental ingestion detecting apparatus and notify a user that accidental ingestion by the animal has occurred.

According to such a configuration, detection of accidental ingestion by the animal by the accidental ingestion detecting apparatus can be notified to the owner through, for example, an apparatus carried by the owner.

Furthermore, for example, the accidental ingestion detecting system may further include a first notifying unit which notifies a user that accidental ingestion by the animal has occurred when the accidental ingestion determining unit determines that accidental ingestion by the animal has occurred, a second notifying unit which is independent of the accidental ingestion detecting apparatus and which communicates with a communicating unit included in the accidental ingestion detecting apparatus and notifies the user that accidental ingestion by the animal has occurred when the accidental ingestion determining unit determines that accidental ingestion by the animal has occurred, and a confirmation inputting unit to which is inputted a confirmation result by the user indicating whether or not the swallowing represented by the accidental ingestion notification that is notified by at least one of the first notifying unit and the second notifying unit is accidental ingestion.

In addition, for example, the accidental ingestion detecting system may further include a confirmation result storing unit that stores confirmation result information, in which the confirmation result inputted using the confirmation inputting unit and second swallowing information including date/time information of swallowing indicated by the accidental ingestion notification to which the confirmation result had been inputted are association with each other, wherein the accidental ingestion determining unit may determine that the swallowing indicated by the first swallowing information is not accidental ingestion in a case where a first swallowing date/time indicated by the first swallowing information is not within a predetermined first time range with respect to a feeding date/time indicated by the feeding information when confirmation result information indicating that the swallowing is not accidental ingestion is stored in the confirmation result storing unit within a predetermined second time range with respect to the first swallowing date/time.

According to such a configuration, after the owner inputs a confirmation result of "not accidental ingestion" with respect to swallowing that is "detected as accidental ingestion even though the swallowing is actually not accidental ingestion", a determination of accidental ingestion is no longer made as long as food or a treat is given at roughly the same time of day even if input of feeding information using the feeding information inputting apparatus is not performed. Therefore, an accidental ingestion notification can be prevented from being needlessly made to the owner.

Furthermore, for example, the accidental ingestion detecting system may further include a location positioning unit which measures a position of the accidental ingestion detecting apparatus and which outputs positioning data, and a confirmation result storing unit which stores confirmation result information, in which the confirmation result inputted using the confirmation inputting unit and second swallowing information including a position of the accidental ingestion detecting apparatus upon input of the confirmation result are association with each other, wherein the first swallowing information may include a first swallowing date/time indicating a date/time of swallowing and first location information indicating a location where the swallowing had occurred, and the accidental ingestion determining unit may determine that the swallowing indicated by the first swallowing information is not accidental ingestion in a case where the first swallowing date/time is not within a predetermined first time range with respect to a feeding date/time indicated by the feeding information when confirmation result information indicating that the swallowing is not accidental ingestion is stored in the confirmation result storing unit within a predetermined distance range with respect to the first location information.

According to such a configuration, after the owner inputs a confirmation result of "not accidental ingestion", a determination of accidental ingestion is no longer made as long as food or a treat is given at roughly the same location even if input of feeding information using the feeding information inputting apparatus is not performed. Therefore, an accidental ingestion notification can be prevented from being needlessly made to the owner.

In addition, for example, the accidental ingestion detecting system may further include a location positioning unit which measures a position of the accidental ingestion detecting apparatus and which outputs positioning data, a position monitoring unit which monitors the position of the accidental ingestion detecting apparatus based on positioning data from the location positioning unit, and a confirmation result storing unit that stores confirmation result information, in which the confirmation result inputted using the confirmation inputting unit and second swallowing information including date/time information of swallowing and a position of the accidental ingestion detecting apparatus upon input of the confirmation result are association with each other, wherein at least one of the first notifying unit and the second notifying unit may notify the user that the animal has approached a location where accidental ingestion by the animal had previously occurred when the position monitoring unit detects that the accidental ingestion detecting apparatus has entered a predetermined distance range from a confirmation result input position where a confirmation result that swallowing is accidental ingestion had been previously inputted.

According to such a configuration, when the animal mounted with the accidental ingestion detecting apparatus approaches a location where the owner had previously inputted a confirmation result that "accidental ingestion has occurred", the possibility that accidental ingestion may occur is notified to the owner. Therefore, the owner can pay close attention so that the animal does not perform accidental ingestion when the animal approaches such a location.

Furthermore, for example, the accidental ingestion detecting system may further include a location positioning unit which measures a position of the accidental ingestion detecting apparatus and which outputs positioning data and a user location positioning unit which measures a position of the user and which outputs user positioning data, wherein the accidental ingestion determining unit may determine accidental ingestion based on the positioning data outputted by the location positioning unit and the user positioning data outputted by the user location positioning unit at the time point of detection of swallowing.

In addition, for example, the accidental ingestion detecting system may further include a distance measuring unit which measures a distance between the accidental ingestion detecting apparatus and the user and which outputs distance data, wherein the accidental ingestion determining unit may determine accidental ingestion based on distance data outputted by the distance measuring unit at the time point of detection of swallowing.

According to such a configuration, since a determination of accidental ingestion is not made when a distance between an owner and an animal mounted with the accidental ingestion detecting apparatus is short, an accidental ingestion notification can be prevented from being needlessly made to the owner.

Furthermore, for example, the accidental ingestion detecting system may further include a first notifying unit which notifies a user that accidental ingestion by the animal has occurred when the accidental ingestion determining unit determines that accidental ingestion by the animal has occurred, a second notifying unit which is independent of the accidental ingestion detecting apparatus and which communicates with a communicating unit included in the accidental ingestion detecting apparatus and notifies the user that accidental ingestion by the animal has occurred when the accidental ingestion determining unit determines that accidental ingestion by the animal has occurred, an imaging unit which captures an image of a vicinity of the accidental ingestion detecting apparatus, and a captured image storing unit which stores an image captured by the imaging unit, wherein when the accidental ingestion determining unit determines that accidental ingestion by the animal has occurred, at least one of the first notifying unit and the second notifying unit may include an image which is stored in the captured image storing unit and which had been captured during a certain past time period since detection of the accidental ingestion in an accidental ingestion notification for notifying the user that accidental ingestion by the animal has occurred.

According to such a configuration, by checking an image captured at a time point slightly preceding the detection of accidental ingestion when the owner receives an accidental ingestion notification from the accidental ingestion detecting system, whether or not a swallowed object is food can be confirmed.

In addition, for example, the accidental ingestion detecting system may further include an imaging unit that captures an image of a vicinity of the accidental ingestion detecting apparatus, an image feature quantity storing unit that stores a feature quantity of a predetermined image in advance, and an image feature analyzing unit which analyzes an image captured by the imaging unit to extract a feature quantity and which compares the feature quantity with a feature quantity stored in the image feature quantity storing unit, wherein the accidental ingestion determining unit may determine accidental ingestion based on the feature quantity of an image captured by the imaging unit from a predetermined period of time prior to a time point of detection of swallowing and a feature quantity of the predetermined image that is stored in the image feature quantity storing unit.

According to such a configuration, a determination of accidental ingestion is not made if an owner or food registered in advance appears in an image captured at a time point slightly preceding detection of swallowing. Therefore, an accidental ingestion notification can be prevented from being needlessly made to the owner.

Furthermore, for example, the accidental ingestion detecting system may further include an odor sensing unit that measures an odor in a vicinity of the accidental ingestion detecting apparatus, an odor feature quantity storing unit that stores a feature quantity of a predetermined odor in advance, and an odor feature analyzing unit which analyzes odor data obtained from the odor sensing unit to extract a feature quantity and compare the feature quantity with the feature quantity stored in the odor feature quantity storing unit, wherein the accidental ingestion determining unit may determine accidental ingestion based on the feature quantity of an odor measured by the odor sensing unit from a predetermined period of time prior to a time point of detection of swallowing and a feature quantity of the predetermined odor that is stored in the odor feature quantity storing unit.

According to such a configuration, a determination of accidental ingestion is not made if an odor similar to an odor of an owner or food registered in advance is contained in odor information from a time point slightly preceding the detection of swallowing. Therefore, an accidental ingestion notification can be prevented from being needlessly made to the owner.

In addition, for example, the accidental ingestion detecting system may further include a second notifying unit which is independent of the accidental ingestion detecting apparatus and which communicates with a communicating unit included in the accidental ingestion detecting apparatus and notifies the user that accidental ingestion by the animal has occurred when the accidental ingestion determining unit determines that accidental ingestion by the animal has occurred, wherein the first notifying unit and the second notifying unit may issue a notification using at least one of light, sound, text, and an image.

According to such a configuration, the accidental ingestion detecting apparatus itself can notify the owner that the accidental ingestion detecting apparatus has detected accidental ingestion by the animal. Alternatively, detection of accidental ingestion by the animal by the accidental ingestion detecting apparatus can be notified to the owner through, for example, an apparatus carried by the owner.

Furthermore, for example, in the accidental ingestion detecting apparatus, the swallowing sensing unit may be a sound pickup sensor which is mounted to a neck area of the animal and which picks up sound generated in the throat during swallowing, and the swallowing detecting unit may detect swallowing by performing a frequency analysis on sound signal data that is outputted from the sound pickup sensor.

Furthermore, for example, in the accidental ingestion detecting apparatus, the swallowing sensing unit may be a sound pickup sensor which is mounted to at least one of a chest area and an abdomen area of the animal and which picks up sound generated in at least one of an esophagus and a stomach during swallowing, and the swallowing detecting unit may detect swallowing by performing a frequency analysis on sound signal data that is outputted from the sound pickup sensor.

These inclusive or specific aspects may be realized by a system, a method, an integrated circuit, a computer program, a computer-readable storage medium such as a CD-ROM, or any combination of a system, a method, an integrated circuit, a computer program, and a storage medium.

Hereinafter, embodiments of the present invention will be described with reference to the drawings. It is to be understood that the embodiments described below all represent specific examples of the present invention. Numerical values, shapes, components, steps, sequences of steps, and the like described in the following embodiments are merely examples and are not intended to limit the present invention. In addition, components not described in independent claims that represent top concepts among the components of the following embodiments will be described as arbitrary components. Furthermore, with respect to all of the embodiments, respective contents thereof can be combined.

Embodiment 1

An accidental ingestion detecting apparatus according to Embodiment 1 detects swallowing by an animal and compares a date/time of the occurrence of the swallowing with a date/time included in information which is related to feeding of the animal and which is inputted by an owner. When the date/times are within a predetermined time range, the detected swallowing is determined not to be accidental ingestion. However, when the date/times are not within a predetermined time range, a determination of accidental ingestion is made and notifying means notifies the occurrence of accidental ingestion by the animal to an owner.

FIG. 1 is a diagram showing an appearance of an accidental ingestion detecting apparatus according to Embodiment 1.

As shown in FIG. 1, an accidental ingestion detecting apparatus 100 includes a collar-type main body unit 101 mounted to an animal, a sound pickup sensor 102, an inputting apparatus 103, and a display apparatus 104. The sound pickup sensor 102 is mounted to the inside (a side that comes into contact with the animal) of the collar-type main body unit 101 so as to come into close contact with a neck area of the animal and to collect swallowing sounds created in the neck area.

The inputting apparatus 103 is a switch for inputting the fact that "the animal will now be fed" to the accidental ingestion detecting apparatus 100 when the owner feeds the animal and is mounted to the outside of the collar-type main body unit 101. The inputting apparatus 103 is, for example, a push switch.

The display apparatus 104 is a display apparatus for notifying people around the animal that "accidental ingestion by the animal has occurred". The display apparatus 104 is constituted by a member such as a light emitting diode (LED) and blinking of the display apparatus 104 is controlled so as to be noticeable when notifying accidental ingestion.

Figure 2:
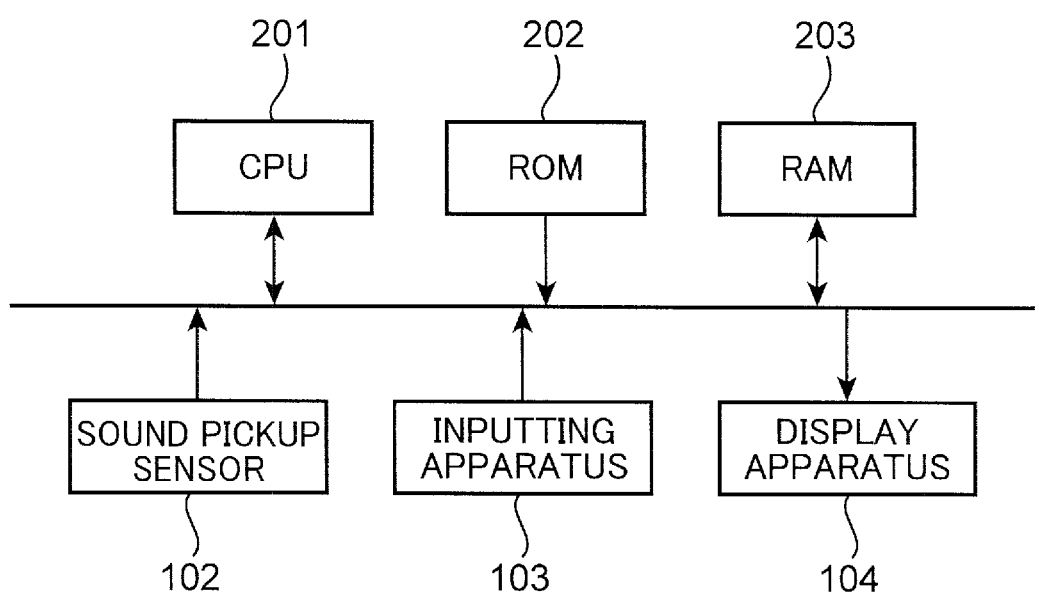
FIG. 2 is a diagram showing a hardware configuration of the accidental ingestion detecting apparatus according to Embodiment 1.

FIG. 2 is a diagram showing a hardware configuration of the accidental ingestion detecting apparatus 100 according to Embodiment 1. The accidental ingestion detecting apparatus 100 includes a central processing unit (CPU) 201, a read only memory (ROM) 202, a random access memory (RAM) 203, the sound pickup sensor 102, the inputting apparatus 103, and the display apparatus 104. Sound data obtained by the sound pickup sensor 102 and feeding information inputted using the inputting apparatus 103 are temporarily stored in the RAM 203. The CPU 201 reads a program for determining accidental ingestion from the ROM 202 and executes the program, and determines accidental ingestion based on the sound data and the feeding information stored in the RAM 203. Furthermore, when the CPU 201 determines that accidental ingestion has occurred, the CPU 201 performs control so that a display for notifying the accidental ingestion is performed by the display apparatus 104.

Figure 3:
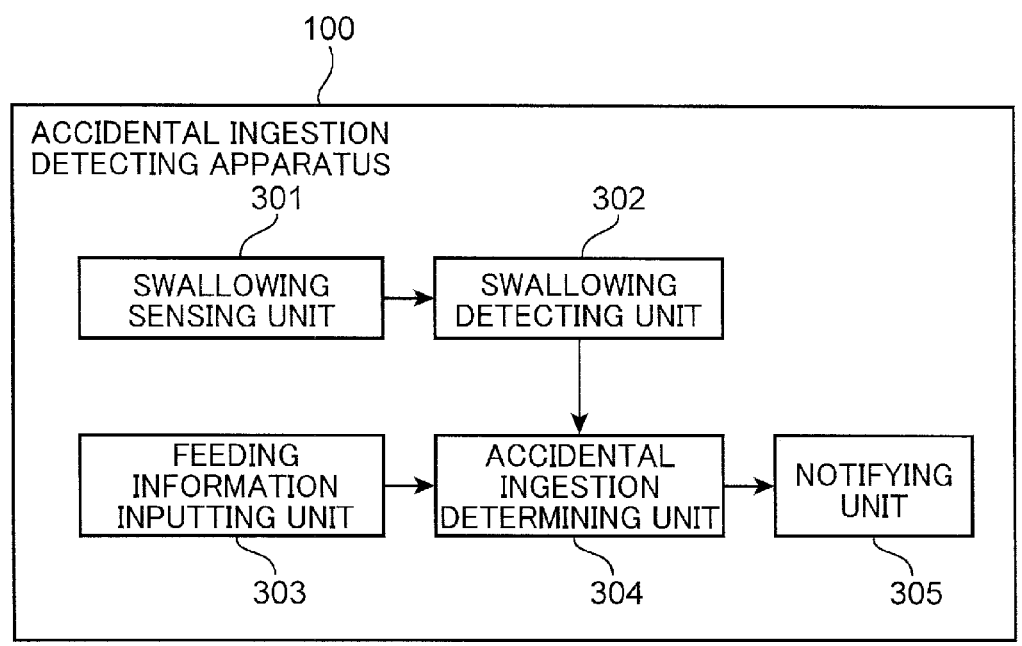
FIG. 3 is a block diagram showing a functional configuration of the accidental ingestion detecting apparatus according to Embodiment 1.

FIG. 3 is a block diagram showing a functional configuration of the accidental ingestion detecting apparatus 100 according to Embodiment 1. The accidental ingestion detecting apparatus 100 includes a swallowing sensing unit 301, a swallowing detecting unit 302, a feeding information inputting unit 303, an accidental ingestion determining unit 304, and a notifying unit 305. The swallowing sensing unit 301 corresponds to the sound pickup sensor 102 shown in FIGS. 1 and 2, the feeding information inputting unit 303 corresponds to the inputting apparatus 103 shown in FIGS. 1 and 2, and the notifying unit 305 corresponds to the display apparatus 104 shown in FIGS. 1 and 2. In addition, the swallowing detecting unit 302 and the accidental ingestion determining unit 304 are realized by the CPU 201 shown in FIG. 2 by executing a program for determining accidental ingestion which is stored in the ROM 202.

The swallowing detecting unit 302 detects swallowing by an animal or, in other words, detects that the animal has swallowed an object based on the sound data collected by the swallowing sensing unit 301. Since methods of detecting swallowing of an object are known techniques, a detailed description will not be given herein. For example, as shown in patent document 1, a method can be adopted which involves collecting a sound of laryngeal action by the swallowing sensing unit 301 and subjecting the obtained sound data to frequency analysis such as wavelet transform to extract a sound made when a bolus passes through the esophagus.

Upon detecting swallowing by the animal, the swallowing detecting unit 302 outputs swallowing information to the accidental ingestion determining unit 304. FIG. 4 is a diagram showing an example of swallowing information. As shown in FIG. 4, swallowing information is constituted by information on a date/time at which swallowing is detected and is outputted from the swallowing detecting unit 302 to the accidental ingestion determining unit 304 every time swallowing is detected. For example, in FIG. 4, swallowing information 401 indicates that an animal mounted with the accidental ingestion detecting apparatus 100 had performed swallowing on 13:48:32 on Mar. 18, 2013, swallowing information 402 indicates that swallowing had been performed on 13:49:05, Mar. 18, 2013, and swallowing information 403 indicates that swallowing had been performed on 14:08:18, Mar. 18, 2013.

When feeding the animal, the owner inputs that "the animal will now be fed" using the feeding information inputting unit 303 of the accidental ingestion detecting apparatus 100. Specifically, when the feeding information inputting unit 303 (the inputting apparatus 103) is constituted by a push switch, the owner can input that "the animal will now be fed" by simply pressing the push switch. Upon accepting an input by the owner, the feeding information inputting unit 303 outputs feeding information to the accidental ingestion determining unit 304.

The accidental ingestion determining unit 304 determines accidental ingestion by the animal based on date/time information included in the swallowing information outputted from the swallowing detecting unit 302 and date/time information included in feeding information outputted from the feeding information inputting unit 303. In this case, the accidental ingestion determining unit 304 may store the accepted swallowing information and feeding information in, for example, the RAM 203.

FIG. 5 is a diagram showing an example of feeding information. As shown in FIG. 5, feeding information is constituted by information of a date/time (feeding information input date/time) at which the owner had performed input using the feeding information inputting unit 303 with the intention of feeding the animal. For example, feeding information 501 shown in FIG. 5 indicates that the owner had performed input using the feeding information inputting unit 303 at 13:48:17, Mar. 18, 2013.

Figure 6:
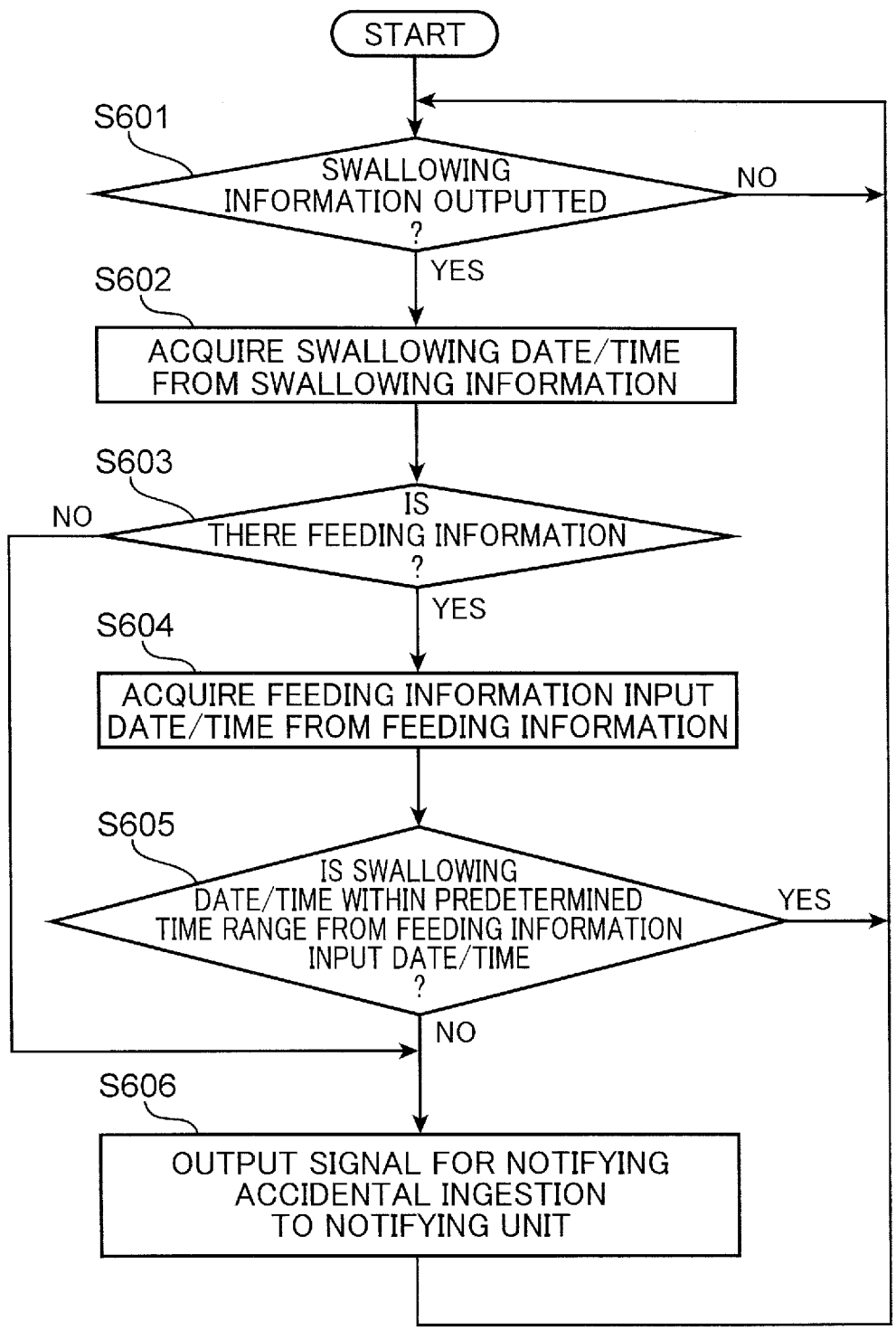
FIG. 6 is a flow chart showing an example of an operation of an accidental ingestion determining unit according to Embodiment 1.

FIG. 6 is a flow chart showing an example of an operation of the accidental ingestion determining unit 304.

The accidental ingestion determining unit 304 checks whether swallowing information has been outputted from the swallowing detecting unit 302 (S601), and when swallowing information has been outputted from the swallowing detecting unit 302 (Yes in S601), acquires a swallowing date/time from the received swallowing information (S602).

Next, the accidental ingestion determining unit 304 checks whether feeding information has been outputted from the feeding information inputting unit 303 (S603). If feeding information has not been outputted from the feeding information inputting unit 303 (No in S603), the accidental ingestion determining unit 304 determines that accidental ingestion by the animal has occurred and outputs a signal for notifying accidental ingestion to the notifying unit 305 (S606). If feeding information has been outputted from the feeding information inputting unit 303 (Yes in S603), a feeding information input date/time is acquired from the feeding information (S604). In other words, in S603, a determination of No is made if feeding information has never been outputted by the feeding information inputting unit 303, and a determination of Yes is made if feeding information has been outputted one or more times. At this point, when a plurality of pieces of feeding information have been outputted by the feeding information inputting unit 303, the accidental ingestion determining unit 304 may acquire latest feeding information.

Subsequently, the accidental ingestion determining unit 304 checks whether the swallowing date/time is within a predetermined time range from the feeding information input date/time (S605). When the swallowing date/time is within a predetermined time range from the feeding information input date/time (Yes in S605), the accidental ingestion determining unit 304 determines that accidental ingestion has not occurred and returns processing to monitoring (S601) of swallowing information. On the other hand, when the swallowing date/time is not within a predetermined time range from the feeding information input date/time (No in S605), the accidental ingestion determining unit 304 determines that accidental ingestion has occurred and outputs a signal for notifying accidental ingestion to the notifying unit 305 (S606), and returns processing to monitoring (S601) of swallowing information.

For example, let us assume that the predetermined time range in S605 is 10 minutes and that swallowing information 401 to 403 shown in FIG. 4 and feeding information shown in FIG. 5 have been obtained. In this case, feeding information 501 indicates that the feeding information input date/time is 13:48:17, Mar. 18, 2013. Therefore, during a period of time from this time until 10 minutes later (13:58:17, Mar. 18, 2013), the accidental ingestion determining unit 304 does not make a determination of accidental ingestion even if swallowing is detected. Since the pieces of swallowing information 401 and 402 shown in FIG. 4 fall within this time range, a determination of accidental ingestion is not made. However, since swallowing information 403 shown in FIG. 4 does not fall within this time range, the accidental ingestion determining unit 304 determines that the swallowing is accidental ingestion and notifies the accidental ingestion by causing the notifying unit 305 to blink.

As described above, with the accidental ingestion detecting apparatus 100 according to Embodiment 1, swallowing by an animal is detected, a date/time of occurrence of the swallowing and a date/time included in information related to feeding of the animal that is inputted by an owner are compared to one another, and the detected swallowing is determined not to be accidental ingestion when the date/times are within a predetermined time range. On the other hand, when the date/times are not within a predetermined time range, a determination of accidental ingestion is made and the notifying unit 305 notifies the owner and people around the animal that accidental ingestion by the animal has occurred. Therefore, accidental ingestion can be detected with high accuracy.

Moreover, while the accidental ingestion detecting apparatus 100 according to the present embodiment is configured so that the notifying unit 305 that notifies accidental ingestion is constituted by an LED and performs notification by causing the LED to blink, this is simply an example. For example, the notifying unit 305 may be constituted by an acoustic generating apparatus such as a buzzer of a speaker instead of a light emitting member such as an LED, whereby accidental ingestion may be notified by sound. Alternatively, the notifying unit 305 may be constituted by a liquid crystal display, an organic electro luminescence (EL) display, or the like instead of a light emitting member such as an LED, whereby accidental ingestion may be notified by displaying a text or an image indicating an occurrence of accidental ingestion. Furthermore, the notifying unit 305 may notify accidental ingestion by combining two or more of light, sound, text, and image display.

In addition, while feeding information according to the present embodiment has been described as information indicating a date/time at which input is performed by the user using the feeding information inputting unit 303 with the intention of feeding the animal, feeding information may alternatively indicate a scheduled data and time of feeding.

Embodiment 2

Figure 7:
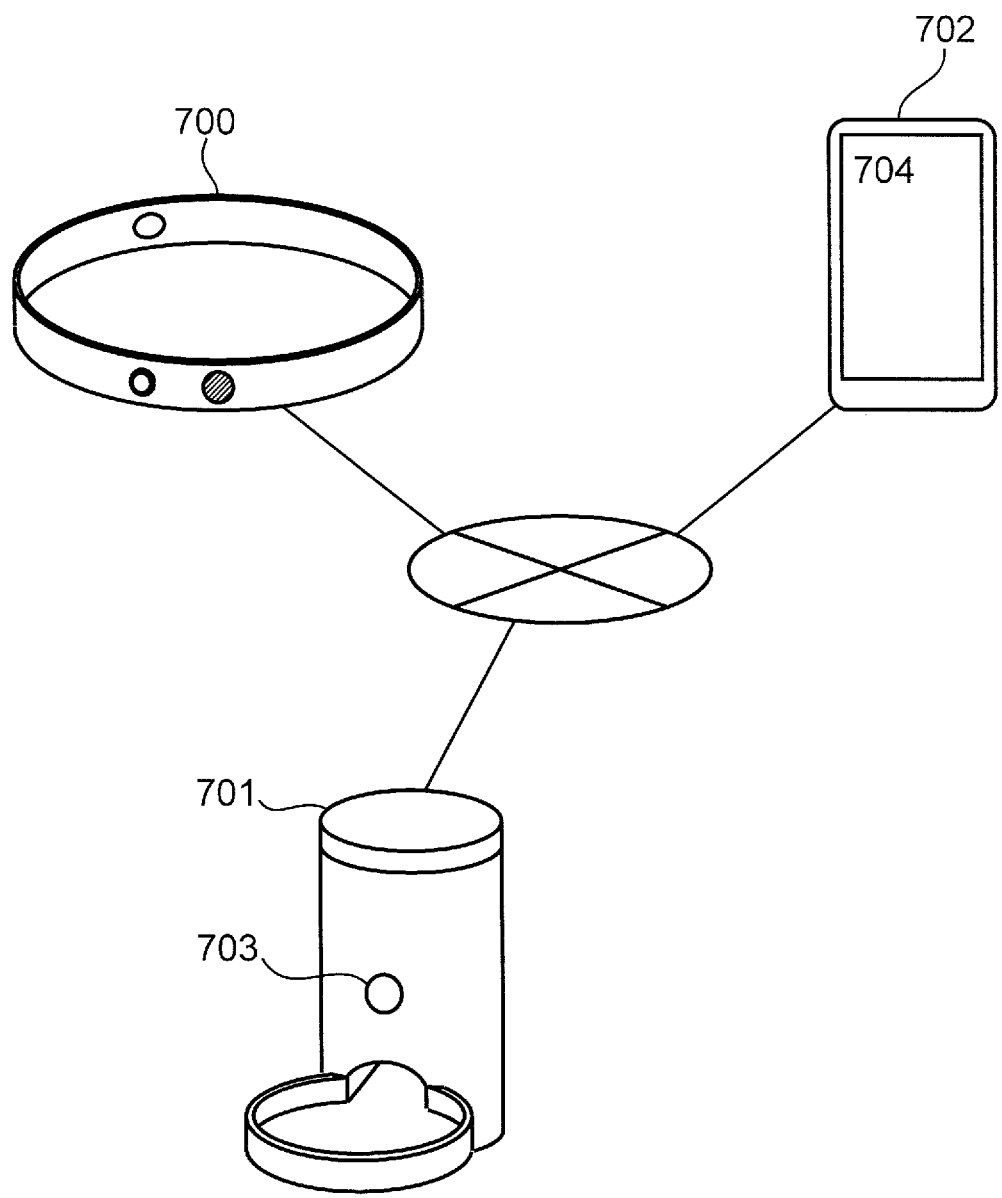
FIG. 7 is a diagram showing an apparatus configuration of an accidental ingestion detecting system according to Embodiment 2.

FIG. 7 is a diagram showing an apparatus configuration of an accidental ingestion detecting system according to Embodiment 2. With the accidental ingestion detecting system according to Embodiment 2, an accidental ingestion detecting apparatus 700 mounted to an animal detects swallowing by the animal, and a date/time of occurrence of the swallowing and a date/time included in feeding information inputted using a feeding information inputting apparatus 701 that differs from the accidental ingestion detecting apparatus 700 are compared to one another. When the date/times are within a predetermined time range, the detected swallowing is determined not to be accidental ingestion. However, when the date/times are not within a predetermined time range, a determination of accidental ingestion is made. Subsequently, a notifying unit 305 of the accidental ingestion detecting apparatus 700 and a notifying apparatus 702 that is a different apparatus from the accidental ingestion detecting apparatus 700 notify an owner that accidental ingestion by the animal has occurred.

According to this configuration, when the owner is at a location separated from the animal such as when the owner has stepped out of the house while leaving the animal behind or when the owner and the animal are both at home but are at locations that differ from one another, an occurrence of accidental ingestion by the animal can be notified to the owner.

As shown in FIG. 7, the accidental ingestion detecting system includes the accidental ingestion detecting apparatus 700 that is mounted to an animal, the feeding information inputting apparatus 701, and the notifying apparatus 702 (an example of a second notifying unit). Specifically, the feeding information inputting apparatus 701 is an automatic feeder that automatically feeds the animal and is an apparatus that dispenses food stored in a main body to a tray at the time set by the owner in an amount set by the owner. In addition to an apparatus configuration of a known automatic feeder, the feeding information inputting apparatus 701 includes a proximity sensor 703 which detects that an animal is approaching and a communicating unit (not shown). In this case, the communicating unit is constituted by a communicating apparatus capable of communicating with a communicating unit 802 of the accidental ingestion detecting apparatus 700 and, for example, an IEEE 802.11 series or IEEE802.15 series wireless communication apparatus can be adopted.

The notifying apparatus 702 is, specifically, an information processing device such as a mobile phone. The notifying apparatus 702 includes a communicating unit (not shown) and a display unit 704 constituted by a liquid crystal display with a touch panel, and performs display for notifying accidental ingestion on the display unit 704 when a notification of accidental ingestion is issued by the accidental ingestion detecting apparatus 700. In this case, the communicating unit of the notifying apparatus 702 is constituted by a communicating apparatus capable of communicating with a communicating unit 802 of the accidental ingestion detecting apparatus 700 in a similar manner to the communicating unit of the feeding information inputting apparatus 701 and, for example, an IEEE 802.11 series or IEEE802.15 series wireless communication apparatus can be adopted.

Figure 8:
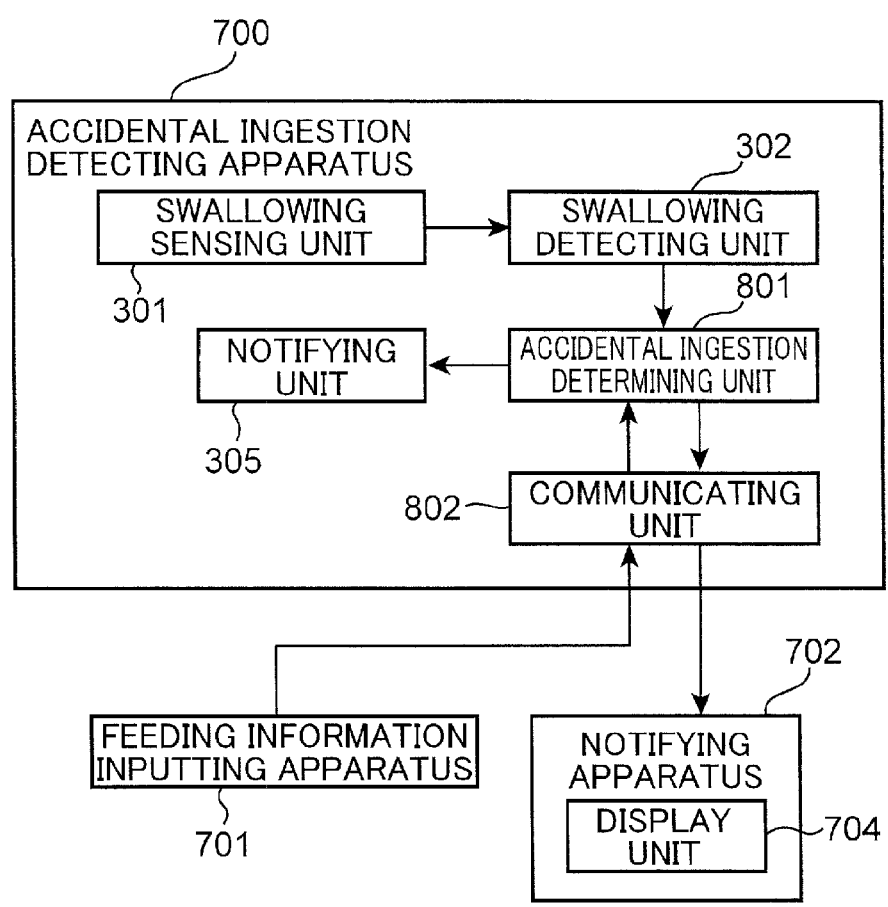
FIG. 8 is a block diagram showing a functional configuration of the accidental ingestion detecting system according to Embodiment 2.

FIG. 8 is a block diagram showing a functional configuration of the accidental ingestion detecting system according to Embodiment 2. The accidental ingestion detecting system includes the accidental ingestion detecting apparatus 700 that is mounted to an animal, a feeding information inputting apparatus 701, and a notifying apparatus 702.

The accidental ingestion detecting apparatus 700 includes a swallowing sensing unit 301, a swallowing detecting unit 302, an accidental ingestion determining unit 801, a notifying unit 305, and the communicating unit 802. Since the swallowing sensing unit 301, the swallowing detecting unit 302, and the notifying unit 305 are the same as the respective units of the accidental ingestion detecting apparatus 100 according to Embodiment 1, a description thereof will be omitted.

The accidental ingestion determining unit 801 determines an occurrence of accidental ingestion by an animal based on date/time information (an example of a first swallowing date/time) included in swallowing information (an example of first swallowing information) that is outputted by the swallowing detecting unit 302 and on date/time information included in feeding information which is outputted by the feeding information inputting apparatus 701 and which is acquired through the communicating unit 802. In addition, upon detecting accidental ingestion, the accidental ingestion determining unit 801 transmits accidental ingestion notification information for notifying the owner that accidental ingestion by the animal has occurred to the notifying apparatus 702 through the communicating unit 802. Moreover, details of an operation of the accidental ingestion determining unit 801 will be described later.

The communicating unit 802 is constituted by a communicating apparatus that communicates with the communicating unit (not shown) of the feeding information inputting apparatus 701 and the communicating unit (not shown) of the notifying apparatus 702 and, for example, an IEEE 802.11 series or IEEE802.15 series wireless communication apparatus can be adopted.

When an approach by the animal is detected by the proximity sensor 703 within a predetermined period of time from a feeding time set by the owner, the feeding information inputting apparatus 701 transmits feeding information to the accidental ingestion detecting apparatus 700 through a communicating unit (not shown).

When accidental ingestion is detected by the accidental ingestion detecting apparatus 700, the notifying apparatus 702 receives accidental ingestion notification information that is transmitted by the accidental ingestion detecting apparatus 700 through the communicating unit 802 and displays contents thereof on the display unit 704 to notify the accidental ingestion by the animal to the owner.

FIG. 9 is a diagram showing an example of the accidental ingestion notification information 901. As shown in FIG. 9, the accidental ingestion notification information 901 includes information of a date/time at which swallowing determined as accidental ingestion had been detected. For example, the accidental ingestion notification information 901 shown in FIG. 9 indicates that swallowing detected at 14:08:18 on Mar. 3, 2013 has been determined to be accidental ingestion.

Figure 10:
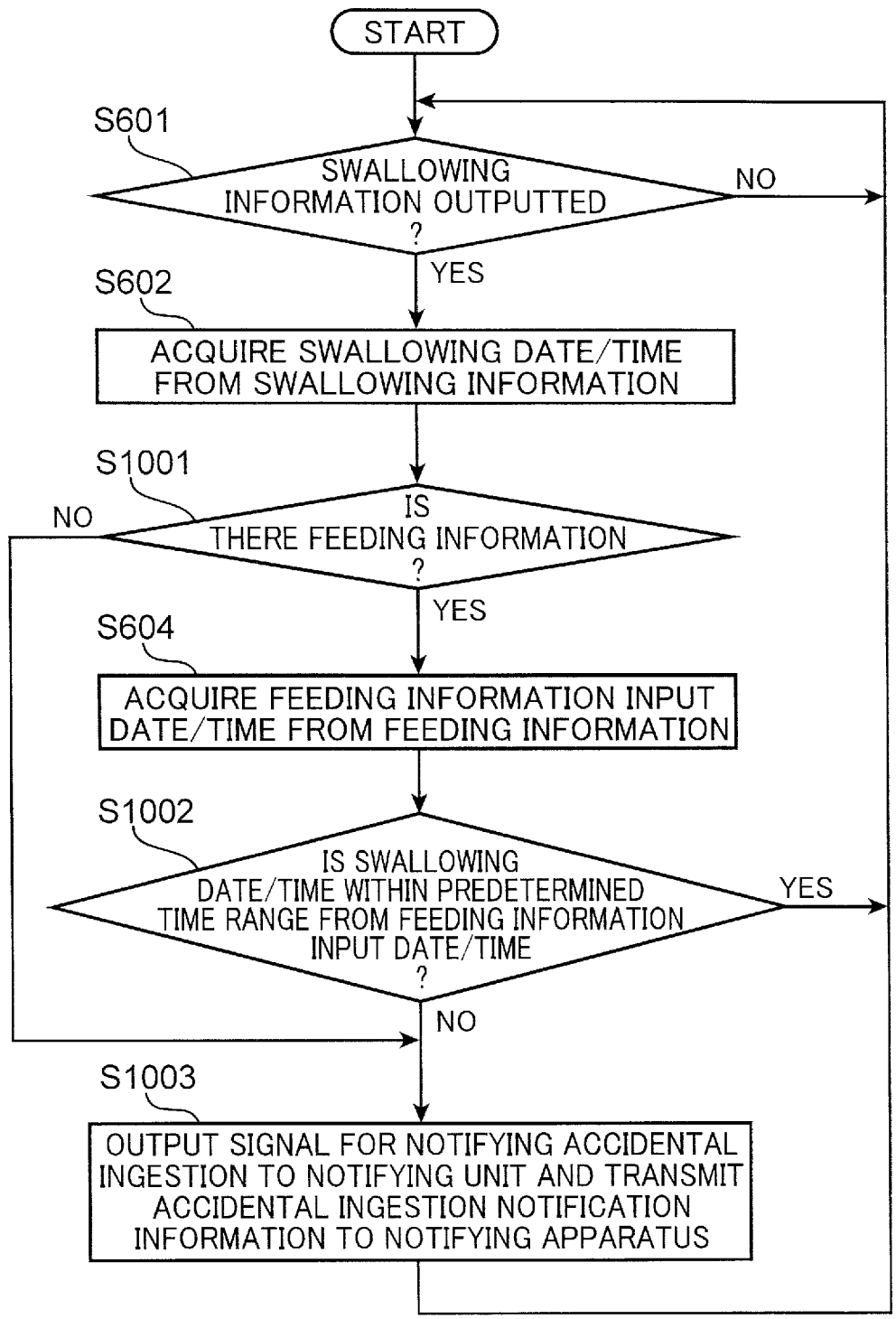
FIG. 10 is a flow chart showing an example of an operation of an accidental ingestion determining unit according to Embodiment 2.

FIG. 10 is a flow chart showing an example of an operation of the accidental ingestion determining unit 801.

Since S601, S602, and S604 following the start of operation of the accidental ingestion determining unit 801 are the same as S601, S602, and S604 shown in FIG. 6 which shows an example of an operation according to Embodiment 1, a description will be omitted.

In S1001, the accidental ingestion determining unit 801 checks whether feeding information has been outputted by the feeding information inputting apparatus 701. If feeding information has not been outputted by the feeding information inputting apparatus 701 (No in S1001), the accidental ingestion determining unit 801 advances processing to S1003. If feeding information has been outputted from the feeding information inputting apparatus 701 (Yes in S1001), a feeding information input date/time is acquired from the feeding information (S604).

After acquiring feeding information input date/time from the feeding information in S604, the accidental ingestion determining unit 801 checks whether the swallowing date/time is within a predetermined time range from the feeding information input date/time (S1002). When the swallowing date/time is within a predetermined time range from the feeding information input date/time (Yes in S1002), the accidental ingestion determining unit 801 determines that accidental ingestion has not occurred and returns processing to monitoring (S601) of swallowing information. When the swallowing date/time is not within a predetermined time range from the feeding information input date/time (No in S1002), the accidental ingestion determining unit 801 determines that accidental ingestion has occurred. Subsequently, the accidental ingestion determining unit 801 outputs a signal for notifying accidental ingestion to the notifying unit 305 and transmits accidental ingestion notification information for notifying accidental ingestion to the notifying apparatus 702 via the communicating unit 802 (S1003), and returns processing to the monitoring (S601) of swallowing information.

Figure 11:
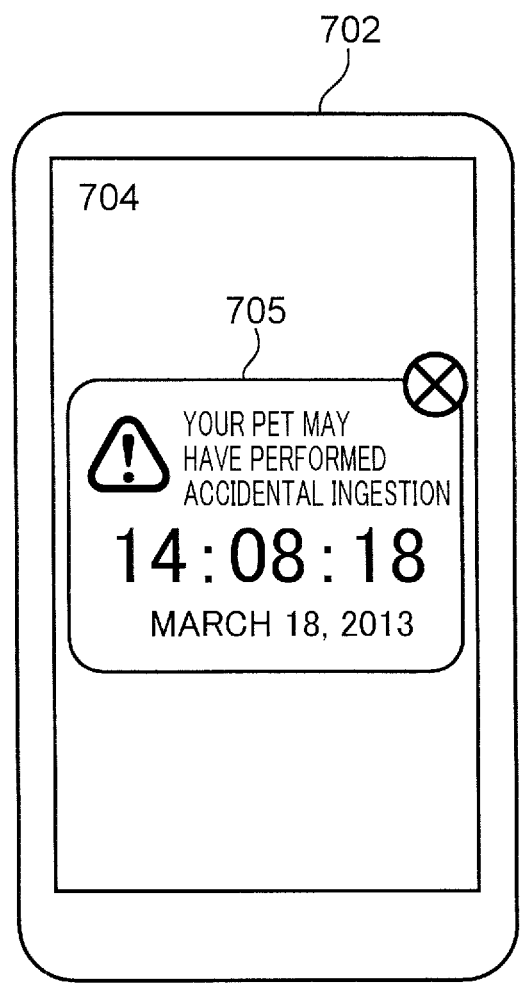
FIG. 11 is a diagram showing an example of display content that is displayed by a notifying apparatus according to Embodiment 2.

FIG. 11 is a diagram showing an example of display contents displayed by the notifying apparatus 702 having received the accidental ingestion notification information. As shown in FIG. 11, upon receiving accidental ingestion notification information, the notifying apparatus 702 causes a pop-up image 705 to be displayed on the display unit 704 based on contents thereof and notifies accidental ingestion by the animal to the owner. The pop-up image 705 shown in FIG. 11 is created based on accidental ingestion notification information 901 shown in FIG. 9. In this case, the accidental ingestion notification information 901 shown in FIG. 9 includes a description reading "14:08:18, Mar. 18, 2013". Therefore, the notifying apparatus 702 creates the pop-up image 705 containing a text conveying the possibility that accidental ingestion by a pet has occurred at 14:08:18, Mar. 18, 2013".

As described above, with the accidental ingestion detecting system according to Embodiment 2, swallowing by an animal is detected by an accidental ingestion detecting apparatus 700 that is mounted to an animal, a date/time of occurrence of the swallowing and a date/time included in feeding information that is inputted using a feeding information inputting apparatus 701 that is a different apparatus from the accidental ingestion detecting apparatus 700 are compared to one another, and the detected swallowing is determined not to be accidental ingestion when the date/times are within a predetermined time range. On the other hand, a determination of accidental ingestion is made when the date/times are not within a predetermined time range, and the accidental ingestion by the animal is notified to an owner by a notifying unit 305 of the accidental ingestion detecting apparatus 700 and a notifying apparatus 702 that is a different apparatus from the accidental ingestion detecting apparatus 700.

While the accidental ingestion detecting system according to the present embodiment has been described on the assumption that the feeding information inputting apparatus 701 is an automatic feeder, the feeding information inputting apparatus 701 may alternatively be an information processing device such as a mobile phone. Such a configuration is useful when the owner is at home and the animal is fed by the owner without using an automatic feeder.

In this case, a dedicated application for notifying feeding information is activated by the information processing device and a display of the information processing device displays an input button for inputting "the animal will now be fed". Subsequently, immediately before feeding the animal, the owner need only press the input button that is displayed on the display to cause the accidental ingestion detecting apparatus 700 to output feeding information.

In addition, while the notifying apparatus 702 has been described to be an information processing device and particularly a mobile phone, the notifying apparatus 702 is not limited to a mobile phone and may be any device as long as similar functions of receiving and displaying accidental ingestion notification information are provided. For example, the notifying apparatus 702 may be constituted by a television set, a personal computer, or a tablet information terminal having similar functions. Accordingly, even in a case where an owner is at home watching television or using a personal computer or a tablet information terminal and accidental ingestion by an animal occurs at a location which differs from that of the owner, the owner can be immediately informed of the accidental ingestion by the animal.

Embodiment 3

Figure 12:
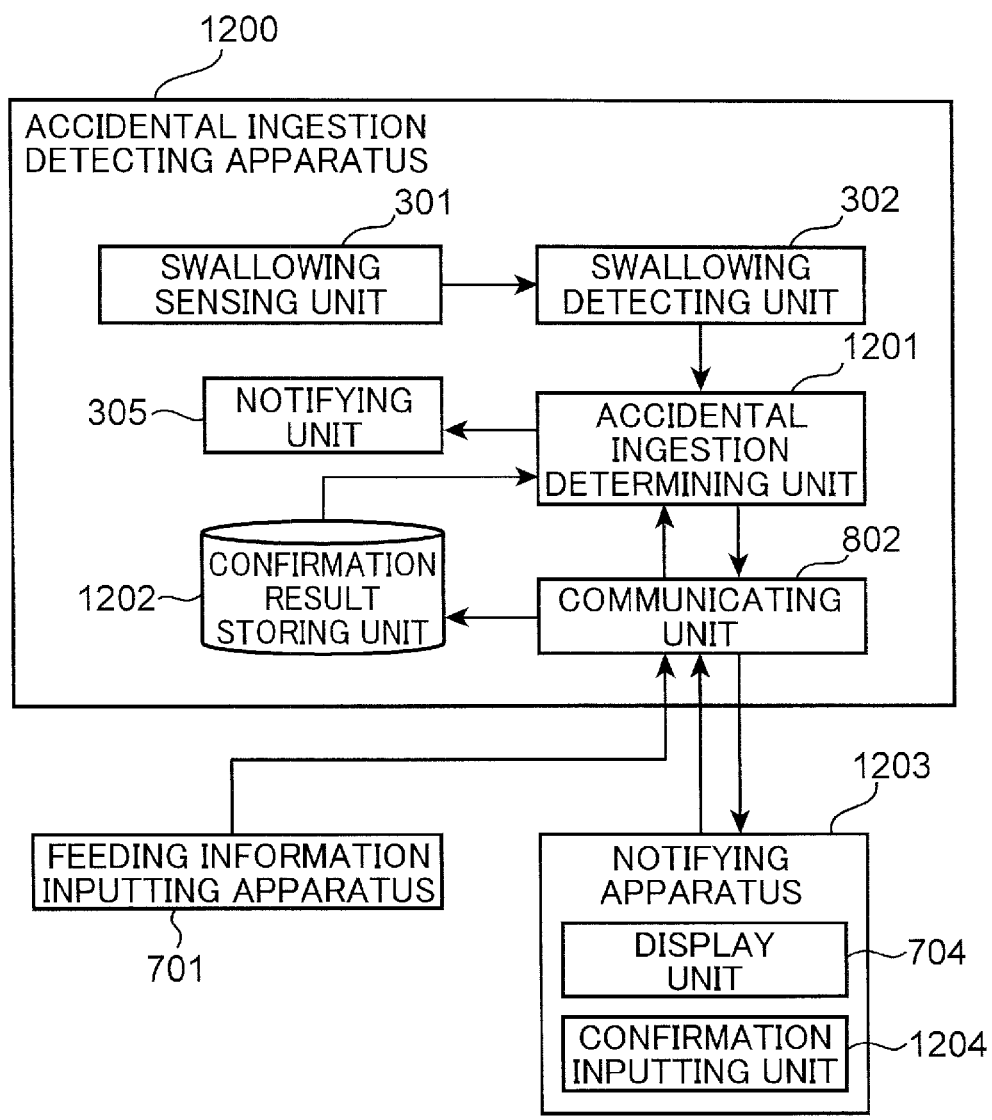
FIG. 12 is a block diagram showing a functional configuration of an accidental ingestion detecting system according to Embodiment 3.

FIG. 12 is a block diagram showing a functional configuration of an accidental ingestion detecting system according to Embodiment 3. The accidental ingestion detecting system according to Embodiment 3 further includes a confirmation inputting unit 1204 which is used by an owner having received an accidental ingestion notification to input a confirmation result regarding whether accidental ingestion has actually occurred and a confirmation result storing unit 1202 that stores a confirmation result inputted using the confirmation inputting unit 1204.

Upon detecting swallowing by an animal, a swallowing detecting unit 302 compares a date/time of the occurrence of the swallowing with a date/time included in feeding information which is inputted using a feeding information inputting apparatus 701 that differs from an accidental ingestion detecting apparatus 1200. When the date/times are within a predetermined time range, the detected swallowing is determined not to be accidental ingestion. On the other hand, when the date/times are not within a predetermined time range, a check is performed to determine whether there is "swallowing confirmed not to be accidental ingestion by the owner" within a predetermined time range from the time of the current swallowing among previous confirmation results stored in the confirmation result storing unit 1202. When such swallowing exists, the detected swallowing is determined not to be accidental ingestion. On the other hand, a determination of accidental ingestion is made when such swallowing does not exist and an occurrence of accidental ingestion by the animal is notified to the owner by a notifying unit 305 of the accidental ingestion detecting apparatus 1200 and the notifying apparatus 1203.

With the accidental ingestion detecting system according to Embodiment 2, when the feeding information inputting apparatus 701 is an automatic feeder or the like, a determination of accidental ingestion is made when an owner manually feeds an animal food or a treat instead of using the automatic feeder. Even with a configuration in which the feeding information inputting apparatus 701 is an information processing device such as a mobile phone, a determination of accidental ingestion is made when the owner forgets to input feeding information before giving food or a treat to the animal. Therefore, conceivably, the owner ends up receiving an excessive number of accidental ingestion notifications.

With the accidental ingestion detecting system according to Embodiment 3, after the owner inputs a confirmation result indicating "not an accidental ingestion" with respect to swallowing that is "detected as accidental ingestion even though the swallowing is actually not accidental ingestion", the swallowing is no longer determined to be accidental ingestion. Therefore, since a determination of accidental ingestion is not made as long as food or a treat is given at roughly the same time of day even if input of feeding information using the feeding information inputting apparatus 701 is not performed, the owner can avoid receiving an excessive number of accidental ingestion notifications.

As shown in FIG. 12, the accidental ingestion detecting system includes the accidental ingestion detecting apparatus 1200 that is mounted to an animal, the feeding information inputting apparatus 701, and the notifying apparatus 1203.

The accidental ingestion detecting apparatus 1200 includes a swallowing sensing unit 301, a swallowing detecting unit 302, an accidental ingestion determining unit 1201, the confirmation result storing unit 1202, a notifying unit 305, and the communicating unit 802. Since the swallowing sensing unit 301, the swallowing detecting unit 302, the notifying unit 305, and the communicating unit 802 are the same as the respective units of the accidental ingestion detecting apparatuses 100 and 1200 according to Embodiments 1 and 2, a description thereof will be omitted. The accidental ingestion determining unit 1201 is realized by the CPU 201 by executing a program for determining accidental ingestion which is stored in the ROM 202. Even when the time of the currently detected swallowing is not within a predetermined first time range with respect to the time included in feeding information, as long as confirmation result information 1401 of "not accidental ingestion" that is within a predetermined second time range with respect to the time of the currently detected swallowing exists in the confirmation result information 1401 stored in the confirmation result storing unit 1202, the accidental ingestion determining unit 1201 determines that the currently detected swallowing is not accidental ingestion. Details of an operation of the accidental ingestion determining unit 1201 will be described later. The confirmation result storing unit 1202 corresponds to the RAM 203. The confirmation result storing unit 1202 stores confirmation result information (FIG. 14). Details of the confirmation result information will be described later. The above also applies to subsequent embodiments.

Since the feeding information inputting apparatus 701 is the same as the feeding information inputting apparatus 701 in the accidental ingestion detecting system according to Embodiment 2, a description thereof will be omitted.

The notifying apparatus 1203 is, specifically, an information processing device such as a mobile phone. The notifying apparatus 1203 includes a communicating unit (not shown), a display unit 704 that is constituted by a liquid crystal display with a touch panel, and a confirmation inputting unit 1204 that is used by the owner to input a confirmation result with respect to an accidental ingestion notification displayed on the display unit 704.

Figure 13:
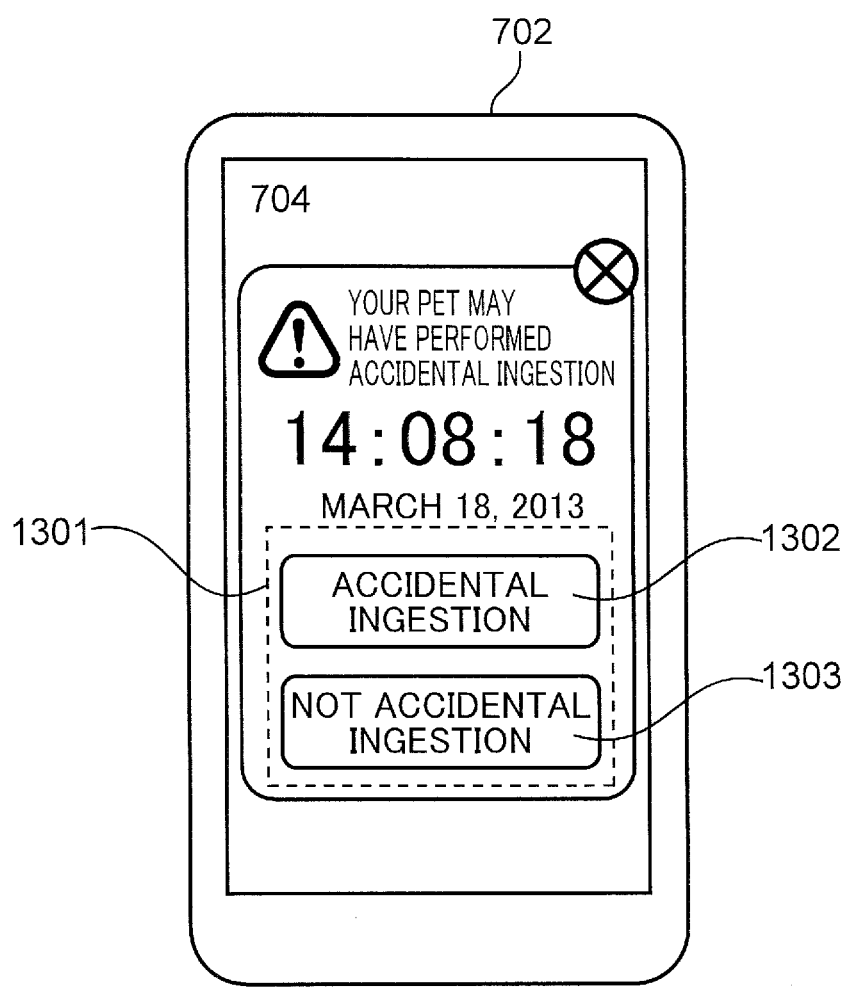
FIG. 13 is a diagram showing an example of display content that is displayed by a notifying apparatus according to Embodiment 3.

FIG. 13 is a diagram showing an example of display contents displayed by the notifying apparatus 1203 having received the accidental ingestion notification information. In addition to an image for notifying accidental ingestion to the owner, the display unit 704 displays a confirmation input graphical user interface (GUI) 1301 to be used by the owner to input a confirmation result regarding whether accidental ingestion by the animal had actually occurred. The confirmation input GUI 1301 is an example of the confirmation inputting unit 1204. The confirmation input GUI 1301 includes a button 1302 labeled "accidental ingestion" and a button 1303 labeled "not accidental ingestion". The owner having received an accidental ingestion notification confirms whether accidental ingestion by the animal had actually occurred, and the owner operates the button 1302 when it is confirmed that accidental ingestion by the animal had actually occurred. Meanwhile, when accidental ingestion had not occurred or, in other words, when the owner had explicitly given food or the like, the owner operates the button 1303.

FIG. 14 is a diagram showing an example of confirmation result information 1401 that is a unit of information used when storing a confirmation result inputted using the confirmation input GUI 1301 and swallowing information related to swallowing of a confirmation object in association with one another. As shown in FIG. 14, the confirmation result information 1401 includes information (an example of second swallowing information) on a date/time of detection of swallowing that had been confirmed by the owner as to whether the swallowing is accidental ingestion and information on a confirmation result by the owner with respect to the swallowing. For example, the confirmation result information 1401 shown in FIG. 14 indicates that the swallowing detected at 14:08:18 on Mar. 3, 2013 has been confirmed by the owner to be "accidental ingestion". When the owner performs a confirmation of "not accidental ingestion", information of "not accidental ingestion" is recorded together with a swallowing date/time in the confirmation result information 1401.

In the present embodiment, the confirmation result information 1401 is generated by the notifying apparatus 1203 after the owner operates the confirmation input GUI 1301 and is transmitted to the accidental ingestion detecting apparatus 1200. The confirmation result information 1401 received by the accidental ingestion detecting apparatus 1200 is stored in the confirmation result storing unit 1202.

FIG. 15 is a diagram showing an example of a confirmation result information table that is stored in the confirmation result storing unit 1202. As shown in FIG. 15, the confirmation result information 1401 received by the accidental ingestion detecting apparatus 1200 is recorded in an order of reception in the confirmation result information table. Specifically, the confirmation result information table includes fields of confirmed swallowing date/time 1501 and confirmation result 1502. A swallowing date/time recorded by the confirmation result information 1401 is recorded in the field of confirmed swallowing date/time 1501 and a confirmation result recorded by the confirmation result information 1401 is recorded in the field of confirmation result 1502. In this case, a swallowing date/time at which the owner had performed confirmation as to whether the swallowing is accidental ingestion among the confirmation result information 1401 will be referred to as a confirmed swallowing date/time.

Figure 16:
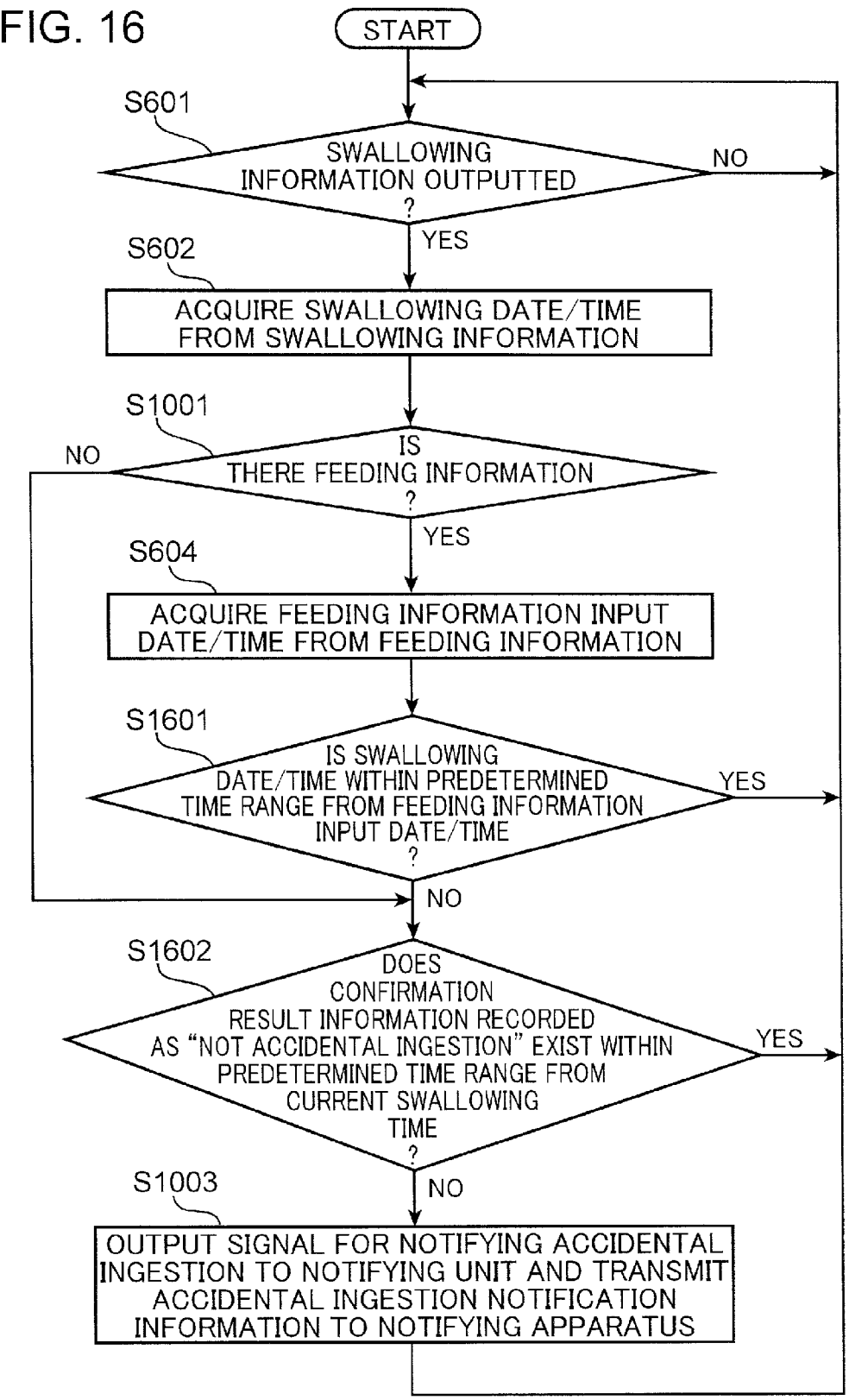
FIG. 16 is a flow chart showing an example of an operation of an accidental ingestion determining unit according to Embodiment 3.

FIG. 16 is a flow chart showing an example of an operation of the accidental ingestion determining unit 1201.

Since S601, S602, and S604 following the start of operation of the accidental ingestion determining unit 1201 are the same as S601, S602, and S604 shown in FIG. 6 which shows an example of an operation of the accidental ingestion detecting apparatus 100 according to Embodiment 1, a description will be omitted. In addition, since S1001 is approximately the same as S1001 in FIG. 10 which shows an example of an operation of the accidental ingestion detecting apparatus 700 according to Embodiment 2, a description will be omitted.

After acquiring feeding information input date/time from the feeding information in S604, the accidental ingestion determining unit 1201 checks whether the swallowing date/time is within a predetermined time range (an example of a first time range: for example, 10 minutes) from the feeding information input date/time (S1601). When the swallowing date/time is within a predetermined time range from the feeding information input date/time (Yes in S1601), the accidental ingestion determining unit 1201 determines that accidental ingestion has not occurred and returns processing to monitoring (S601) of swallowing information. On the other hand, when the swallowing date/time is not within a predetermined time range from the feeding information input date/time (No in S1601), the accidental ingestion determining unit 1201 refers to the confirmation result information table stored in the confirmation result storing unit 1202 and checks whether confirmation result information 1401 recording "not accidental ingestion" exists within a predetermined time range (an example of a second time range) from the currently detected swallowing (S1602). When corresponding confirmation result information 1401 exists (Yes in S1602), the accidental ingestion determining unit 1201 determines that the currently detected swallowing is not accidental ingestion and returns processing to monitoring (S601) of swallowing information. When corresponding confirmation result information 1401 does not exist (No in S1602), the accidental ingestion determining unit 1201 determines that the currently detected swallowing is accidental ingestion. Subsequently, the accidental ingestion determining unit 1201 outputs a signal for notifying accidental ingestion to the notifying unit 305 and transmits accidental ingestion notification information for notifying accidental ingestion to the notifying apparatus 1203 via the communicating unit 802 (S1003), and returns processing to the monitoring (S601) of swallowing information.

Figure 17:
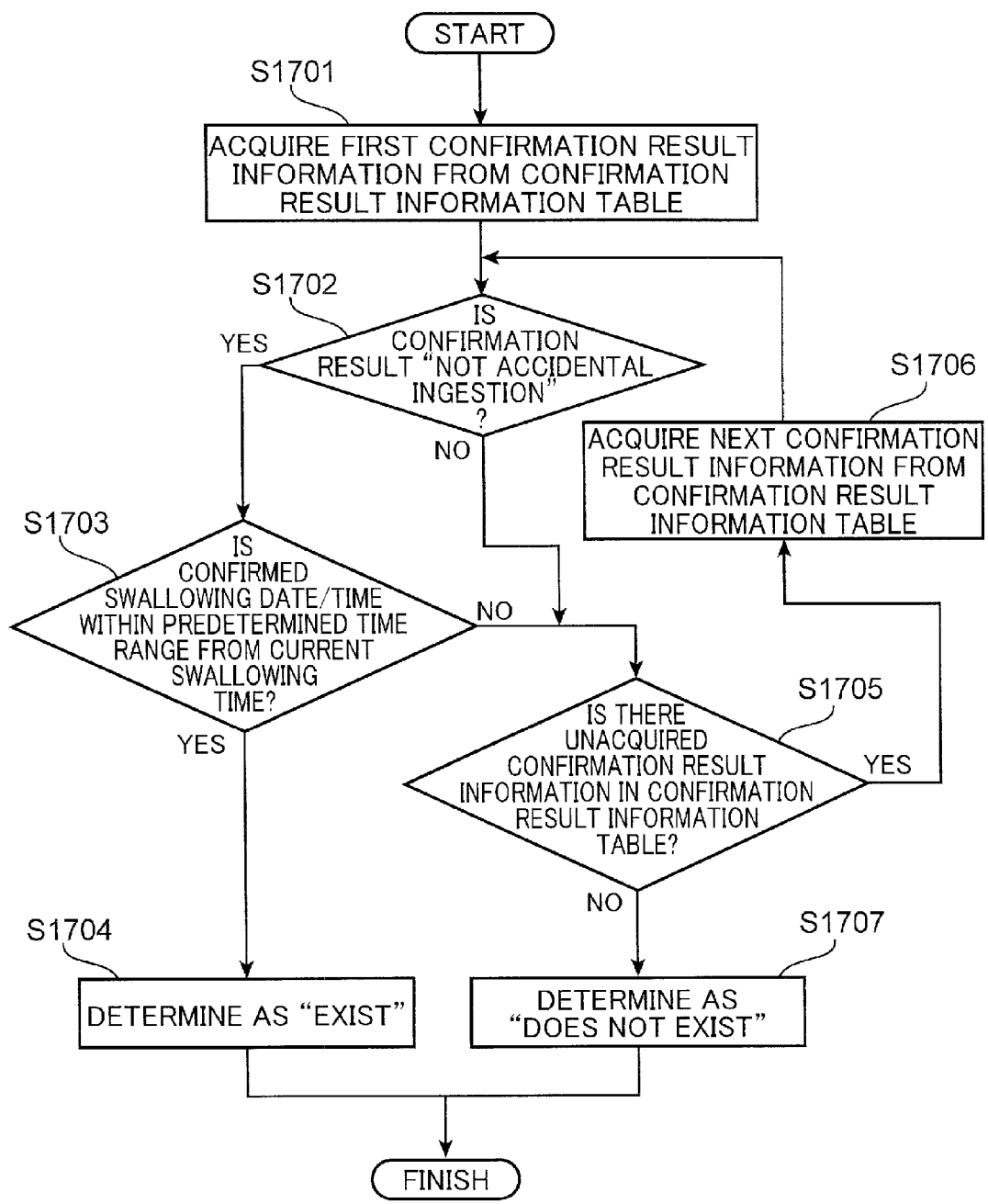
FIG. 17 is a flow chart showing an example of an operation of a part of an accidental ingestion determining unit according to Embodiment 3.

The operation of S1602 will now be described in detail with reference to FIG. 17. The accidental ingestion determining unit 1201 acquires a first piece of confirmation result information 1401 from the confirmation result information table (S1701). Next, a check is made regarding whether "not accidental ingestion" is recorded in the acquired confirmation result information 1401 (S1702). When the check reveals that "not accidental ingestion" is recorded (Yes in S1702), the accidental ingestion determining unit 1201 advances processing to S1703. On the other hand, when "accidental ingestion" is recorded in the acquired confirmation result information 1401 (No in S1702), the accidental ingestion determining unit 1201 advances processing to S1705.

In S1703, the accidental ingestion determining unit 1201 checks whether the confirmed swallowing date/time included in the confirmation result information 1401 is within a predetermined time range from the time of the currently notified swallowing. When within a predetermined time range (Yes in S1703), the accidental ingestion determining unit 1201 determines that there "exists" confirmation result information 1401 recording "not accidental ingestion" within a predetermined time range from the current swallowing time (S1704) and finishes processing. In this case, a Yes determination is made in S1602 and processing is returned to monitoring (S601) of swallowing. In other words, the currently detected swallowing is determined not to be accidental ingestion. On the other hand, when not within a predetermined time range (No in S1703), the accidental ingestion determining unit 1201 advances processing to S1705.

In S1705, the accidental ingestion determining unit 1201 checks whether unacquired confirmation result information 1401 remains in the confirmation result information table. If unacquired confirmation result information 1401 does not remain (No in S1705), the accidental ingestion determining unit 1201 determines that there "does not exist" confirmation result information 1401 recording "not accidental ingestion" within a predetermined time range from the current swallowing time (S1707) and finishes processing. In this case, a determination of No is made in S1602 and processing advances to S1003. In other words, the currently detected swallowing is determined to be accidental ingestion.

On the other hand, when unacquired confirmation result information 1401 remains (Yes in S1705), the accidental ingestion determining unit 1201 acquires next confirmation result information 1401 from the confirmation result information table (S1706), advances processing to S1702, and continues processing.

For example, a case will be considered where the confirmation result information table shown in FIG. 15 is stored in the confirmation result storing unit 1202, swallowing is detected at 15:03:24 on Mar. 22, 2013, and feeding information has not been inputted. In addition, the predetermined time range in S1602 and S1703 is assumed to be 15 minutes.

When swallowing is detected at the date/time described above, the accidental ingestion determining unit 1201 refers to the confirmation result information table to check whether there exists swallowing which had occurred within the predetermined time range (for example, 15 minutes) from 15:03:24 that is the time of the swallowing or, in other words, during a time period from 14:48:24 (a time 15 minutes before 15:03:24) until 15:18:24 (a time 15 minutes after 15:03:24) and which had been confirmed "not accidental ingestion" by the owner. A result of a confirmation of "not accidental ingestion" by the owner is recorded with respect to swallowing that had occurred at 15:12:06 on Mar. 17, 2013 in row 1 of the confirmation result information table shown in FIG. 15. Since 15:12:06 that is the time of swallowing confirmed as "not accidental ingestion" is within the range from 14:48:24 to 15:18:24 described above (Yes in S1703), corresponding swallowing is determined to "exist" (S1704). Therefore, the accidental ingestion determining unit 1201 determines that the current swallowing is "not accidental ingestion".

As shown, the accidental ingestion detecting system according to Embodiment 3 further includes a confirmation inputting unit 1204 which is used by an owner notified of detection of accidental ingestion to input a confirmation result regarding whether accidental ingestion has actually occurred and the confirmation result storing unit 1202 that stores a confirmation result inputted using the confirmation inputting unit 1204. Swallowing (swallowing of an object) by an animal is detected by the accidental ingestion detecting apparatus 1200 mounted to the animal, and a date/time at which the swallowing had occurred and a date/time included in feeding information inputted using the feeding information inputting apparatus 701 are compared to each other. When the date/times are within a predetermined time range, the detected swallowing is determined not to be accidental ingestion. On the other hand, when the date/times are not within a predetermined time range, a check is performed to determine whether there is "swallowing confirmed not to be accidental ingestion by the owner" within a predetermined time range from the time of the current swallowing among previous confirmation results stored in the confirmation result storing unit 1202. When such swallowing exists, the detected swallowing is determined not to be accidental ingestion. On the other hand, a determination of accidental ingestion is made when such swallowing does not exist and an occurrence of accidental ingestion by the animal is notified to the owner by a notifying unit 305 of the accidental ingestion detecting apparatus 1200 and the notifying apparatus 1203. Therefore, an accidental ingestion notification can be prevented from being needlessly made to the owner.

Moreover, while the confirmation result storing unit 1202 has been described as being provided inside the accidental ingestion detecting apparatus 1200 in the accidental ingestion detecting system according to the present embodiment, the confirmation result storing unit 1202 may alternatively be provided outside of the accidental ingestion detecting apparatus 1200. For example, the confirmation result storing unit 1202 may be provided inside the notifying apparatus 1203, inside the feeding information inputting apparatus 701, or in a separate information processing apparatus (such as a home server or a server on the Internet).

In addition, while the confirmation input GUI 1301 has been adopted as an example of the confirmation inputting unit 1204, the confirmation inputting unit 1204 may be provided in other forms. For example, the confirmation inputting unit 1204 may be constituted by a confirmation input switch that is independent from the display unit 704 on the notifying apparatus 1203. Alternatively, the confirmation inputting unit 1204 may be provided in a different housing as the notifying apparatus 1203. For example, a confirmation input switch may be provided in the accidental ingestion detecting apparatus 1200.

Embodiment 4

Figure 18:
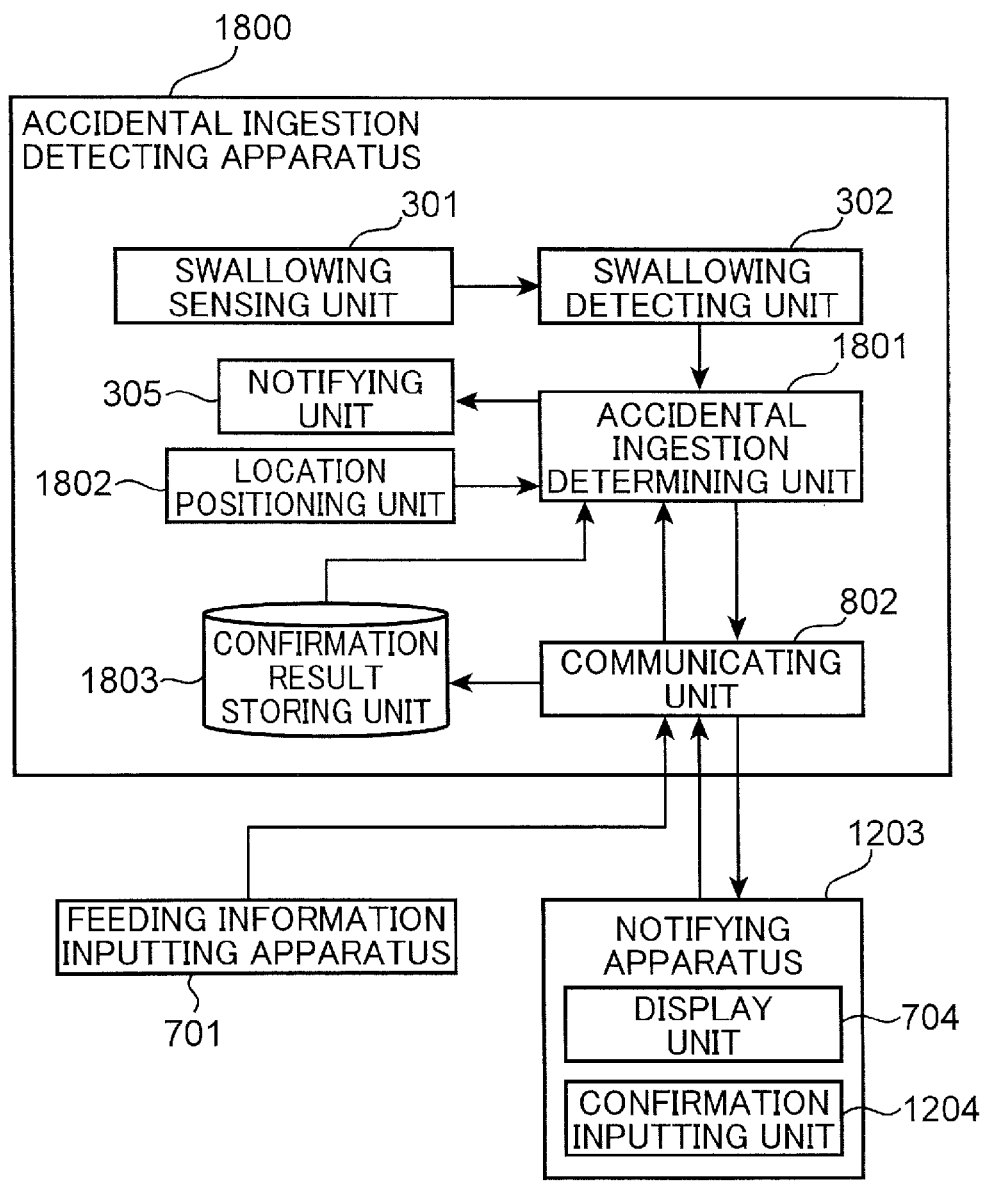
FIG. 18 is a block diagram showing a functional configuration of an accidental ingestion detecting system according to Embodiment 4.

FIG. 18 is a block diagram showing a functional configuration of an accidental ingestion detecting system according to Embodiment 4. In addition to the configuration described in Embodiment 3, the accidental ingestion detecting system according to Embodiment 4 further includes a location positioning unit 1802 that measures a position of an accidental ingestion detecting apparatus 1800.

When the accidental ingestion detecting apparatus 1800 mounted to the animal detects swallowing by the animal, a date/time of the occurrence of the swallowing and a date/time included in feeding information which is inputted using a feeding information inputting apparatus 701 that differs from the accidental ingestion detecting apparatus 1800 are compared with one another. When the date/times are within a predetermined time range, the detected swallowing is determined not to be accidental ingestion. On the other hand, when the date/times are not within a predetermined time range, a check is performed to determine whether there is "swallowing confirmed not to be accidental ingestion by the owner" within a predetermined distance range from a location where the current swallowing had occurred among previous confirmation results stored in the confirmation result storing unit 1803.

When such swallowing exists, the detected swallowing is determined not to be accidental ingestion. On the other hand, a determination of accidental ingestion is made when such swallowing does not exist and an occurrence of accidental ingestion by the animal is notified to the owner by a notifying unit 305 of the accidental ingestion detecting apparatus 1800 and the notifying apparatus 1203.

With the accidental ingestion detecting system according to Embodiment 2, when the feeding information inputting apparatus 701 is an automatic feeder or the like, a determination of accidental ingestion is made when an owner manually feeds an animal food or a treat instead of using the automatic feeder at a regular location when going outdoors such as during a walk or at a roughly regular location inside the house. Even with a configuration in which the feeding information inputting apparatus 701 is an information processing device such as a mobile phone, a determination of accidental ingestion is made when input of feeding information before giving food or a treat to the animal is forgotten.

With the accidental ingestion detecting system according to present Embodiment 4, after the owner inputs a confirmation result of "not accidental ingestion", a determination of accidental ingestion is not made as long as food or a treat is given at roughly the same location even if input of feeding information using the feeding information inputting apparatus 701 is not performed. Therefore, an accidental ingestion notification is prevented from being needlessly made to the owner.

As shown in FIG. 18, the accidental ingestion detecting system includes the accidental ingestion detecting apparatus 1800 that is mounted to an animal, the feeding information inputting apparatus 701, and the notifying apparatus 1203.

The accidental ingestion detecting apparatus 1800 includes a swallowing sensing unit 301, a swallowing detecting unit 302, an accidental ingestion determining unit 1801, a location positioning unit 1802, a confirmation result storing unit 1803, a notifying unit 305, and a communicating unit 802. Since the swallowing sensing unit 301, the swallowing detecting unit 302, the notifying unit 305, and the communicating unit 802 are the same as the respective units of the accidental ingestion detecting apparatuses 100 and 800 according to Embodiments 1 and 2, a description thereof will be omitted. Even when swallowing detected by the swallowing detecting unit 302 is not within a predetermined time range with respect to a date/time indicated by feeding information, the accidental ingestion determining unit 1801 determines that the detected swallowing is not accidental ingestion if confirmation result information indicating "not accidental ingestion" within a predetermined distance range with respect to a swallowing location of the detected swallowing is stored in the confirmation result storing unit 1803. Moreover, details of an operation of the accidental ingestion determining unit 1801 will be described later.

The location positioning unit 1802 is constituted by a positioning sensor. In the present embodiment, the positioning sensor is a GPS sensor. The location positioning unit 1802 measures a current position of the accidental ingestion detecting apparatus 1800 and outputs positioning data to the accidental ingestion determining unit 1801.

Since the feeding information inputting apparatus 701 is the same as the feeding information inputting apparatus 701 in the accidental ingestion detecting system according to Embodiment 2, a description thereof will be omitted.

FIG. 19 is a diagram showing an example of accidental ingestion notification information 1901 received by the notifying apparatus 1203 from the accidental ingestion detecting apparatus 1800. As shown in FIG. 19, the accidental ingestion notification information 1901 includes information on a date/time of detection of swallowing that had been determined to be accidental ingestion and information on a position of the accidental ingestion detecting apparatus 1800 at a time point of detection of the swallowing that had been determined to be accidental ingestion. For example, the accidental ingestion notification information 1901 shown in FIG. 19 indicates that swallowing detected at a position of A degrees B minutes 32 seconds north and C degrees D minutes 37 seconds east at 14:08:18 on Mar. 18, 2013 has been determined to be accidental ingestion.

Upon receiving the accidental ingestion notification information 1901, the notifying apparatus 1203 displays as the confirmation inputting unit 1204 a confirmation input graphical user interface (GUI) 1301 for inputting a result of confirming whether accidental ingestion by the animal had actually occurred on the display unit 704 in addition to a notification regarding accidental ingestion. An example of display contents is as shown in FIG. 13. The owner having received an accidental ingestion notification confirms whether accidental ingestion by the animal had actually occurred and operates the button 1302 labeled "accidental ingestion" when it is confirmed that accidental ingestion by the animal had actually occurred. Meanwhile, when accidental ingestion had not occurred or, in other words, when the owner had explicitly given food or the like, the owner operates the button 1303 labeled "not accidental ingestion".

FIG. 20 is a diagram showing an example of confirmation result information 2001 that is a unit of information used when storing a confirmation result inputted using the confirmation input GUI 1301 and swallowing information related to swallowing of a confirmation object in association with one another. As shown in FIG. 20, the confirmation result information 2001 includes information on a date/time of detection of swallowing that had been confirmed as to whether the swallowing is accidental ingestion, information (an example of second swallowing information) on a position of the accidental ingestion detecting apparatus 1800 at the time point of detection of the swallowing, and information on a confirmation result by the owner with respect to the swallowing. For example, the confirmation result information 2001 shown in FIG. 20 indicates that swallowing detected at a position of A degrees B minutes 32 seconds north and C degrees D minutes 37 seconds east at 14:08:18 on Mar. 18, 2013 has been confirmed to be "accidental ingestion" by the owner. When the owner performs a confirmation of "not accidental ingestion", information of "not accidental ingestion" is recorded together with a swallowing date/time and a swallowing detection position in the confirmation result information.

In the present embodiment, the confirmation result information 2001 is generated by the notifying apparatus 1203 after the owner operates the confirmation input GUI 1301 and is transmitted to the accidental ingestion detecting apparatus 1800. The confirmation result information 2001 received by the accidental ingestion detecting apparatus 1800 is stored in the confirmation result storing unit 1803.

FIG. 21 is a diagram showing an example of a confirmation result information table that is stored in the confirmation result storing unit 1803. As shown in FIG. 21, the confirmation result information 2001 received by the accidental ingestion detecting apparatus 1800 is recorded in an order of reception in the confirmation result information table. Hereinafter, among the stored confirmation result information, a date/time and position of swallowing that has been confirmed as to whether the swallowing is accidental ingestion will be respectively referred to as confirmed swallowing date/time and confirmed swallowing position.

Figure 22:
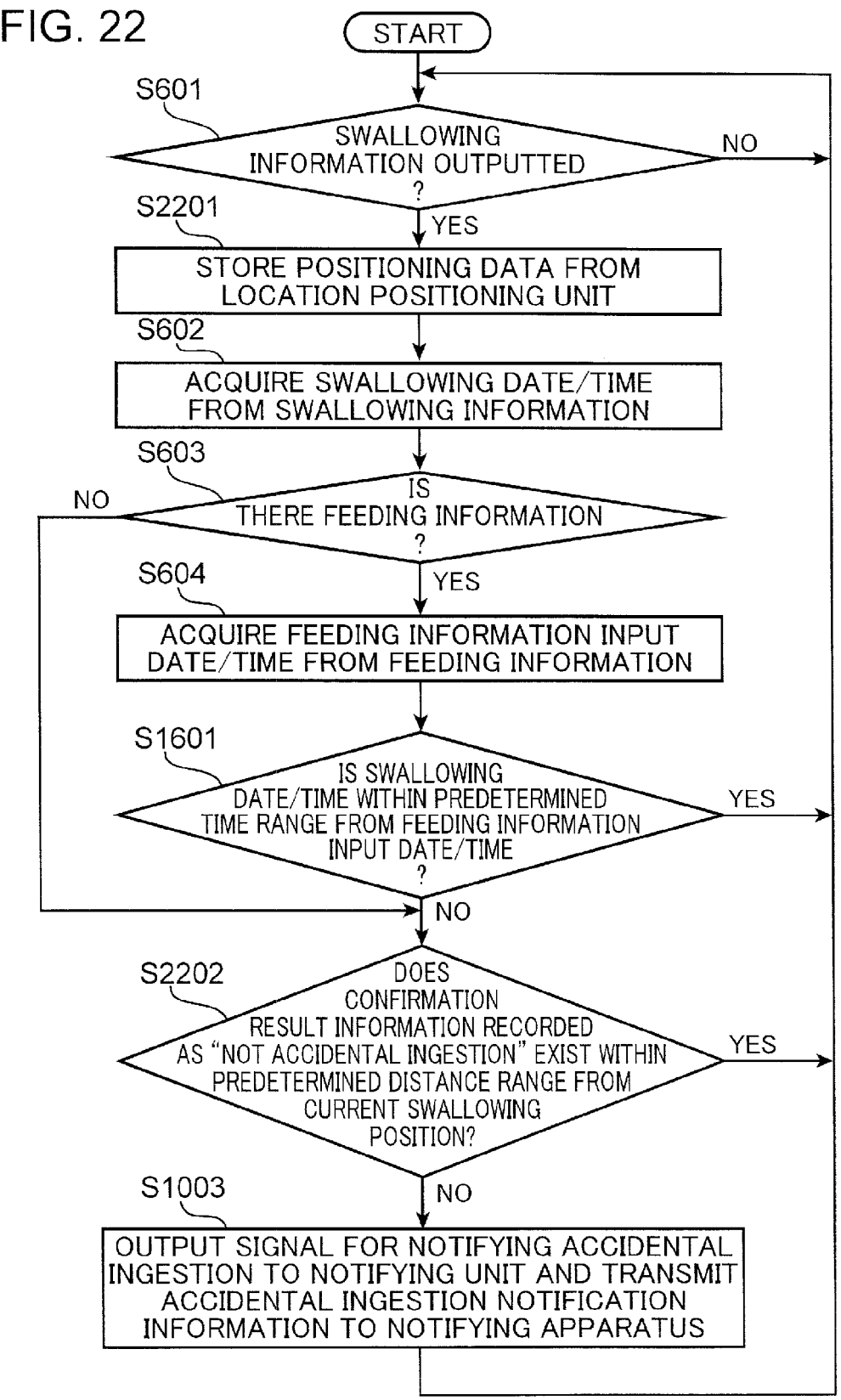
FIG. 22 is a flow chart showing an example of an operation of an accidental ingestion determining unit according to Embodiment 4.

FIG. 22 is a flow chart showing an example of an operation of the accidental ingestion determining unit 1801. Since steps other than S2201 and S2202 are the same as operations in the respective steps in FIG. 16 that shows an example of an operation according to Embodiment 3, a description thereof will be omitted.

In S2201, the accidental ingestion determining unit 1801 temporarily stores positioning data from the location positioning unit 1802. This is performed in order to embed information on a position at the time point where swallowing by the animal had occurred in the accidental ingestion notification information 1901 when the current swallowing is determined to be accidental ingestion in a subsequent step.

Next, S2202 will be described. When a determination of No is made in S603 or S1601, the accidental ingestion determining unit 1801 refers to a confirmation result information table stored in the confirmation result storing unit 1803 and checks whether there exists confirmation result information 2001 related to "swallowing that is not accidental ingestion" within a predetermined distance range from a position of the accidental ingestion detecting apparatus 1800 upon detection of the current swallowing (S2202). When corresponding confirmation result information 2001 exists (Yes in S2202), the accidental ingestion determining unit 1801 makes a determination of "not accidental ingestion" and returns processing to monitoring (S601) of swallowing information. When corresponding confirmation result information 2001 does not exist (No in S1601), the accidental ingestion determining unit 1801 makes a determination of "accidental ingestion" and outputs a signal for notifying accidental ingestion to the notifying unit 305, transmits accidental ingestion notification information 1901 for notifying accidental ingestion to the notifying apparatus 1203 via the communicating unit 802 (S1003), and returns processing to the monitoring (S601) of swallowing information. In S1003, the accidental ingestion determining unit 1801 generates accidental ingestion notification information 1901 such as that shown in FIG. 19 using a swallowing date/time (an example of first swallowing date/time) acquired in S602 and positioning data (an example of first location information) stored in S2201.

Figure 23:
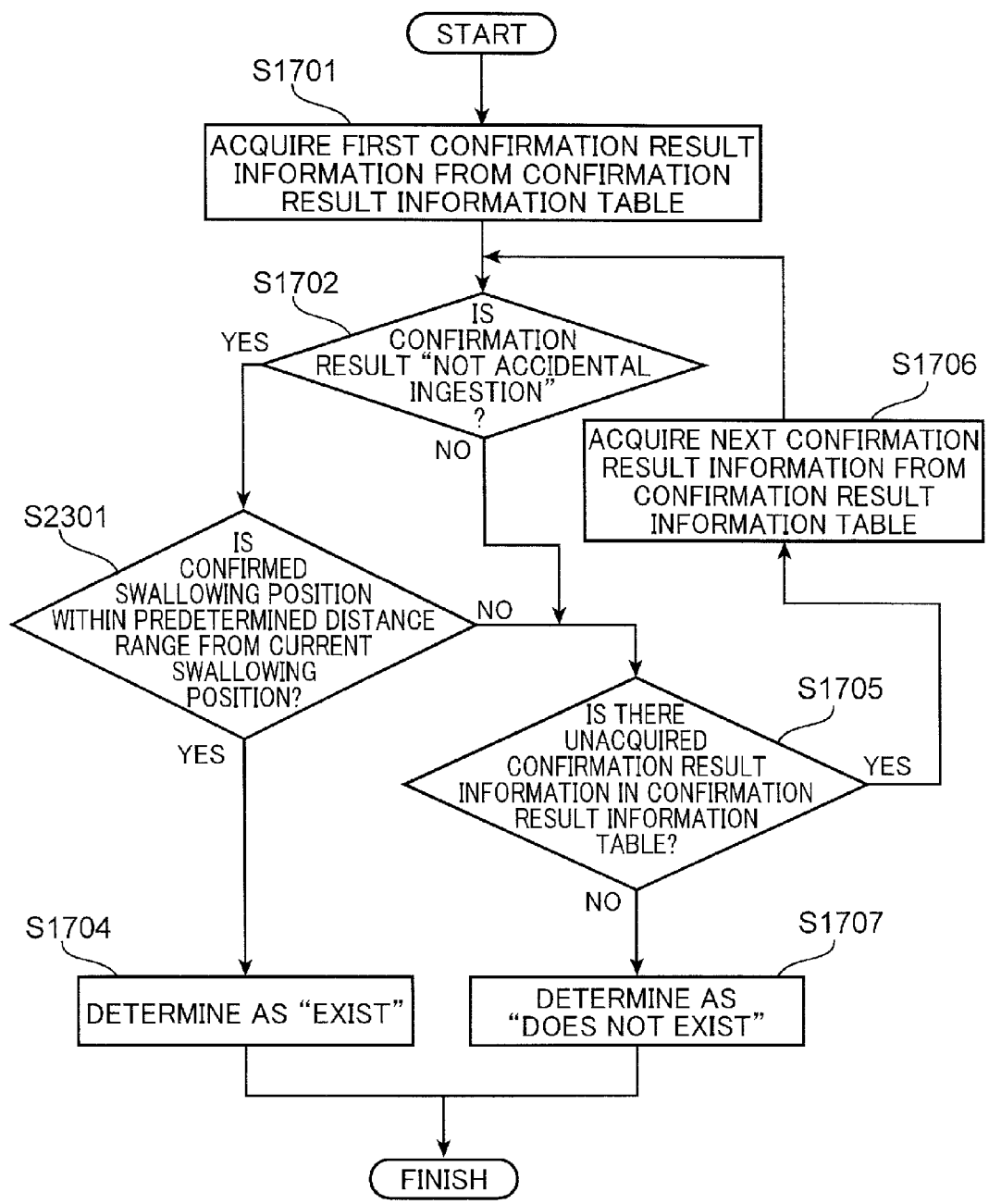
FIG. 23 is a flow chart showing an example of an operation of a part of the accidental ingestion determining unit according to Embodiment 4.

The operation of S2202 will now be described in detail with reference to FIG. 23. Since steps other than S2301 are the same as operations in the respective steps in FIG. 17 that shows an example of an operation according to Embodiment 3, a description thereof will be omitted. In S1702, when it is determined that a confirmation result of acquired confirmation result information is "not accidental ingestion" (Yes in S1702), the accidental ingestion determining unit 1801 checks in S2301 whether a confirmed swallowing position included in confirmation result information 2001 is within a predetermined distance range from a position of currently notified swallowing. When within the predetermined distance range (Yes in S2301), the accidental ingestion determining unit 1801 determines that the corresponding swallowing "exists" (S1704) and finishes processing. When not within the predetermined distance range (No in S1702), the accidental ingestion determining unit 1801 advances processing to S1705.

For example, a case will be considered where the confirmation result information table shown in FIG. 21 is stored in the confirmation result storing unit 1803, swallowing is detected at 15:03:24 on Mar. 22, 2013 at a position of A degrees E minutes 14 seconds north and C degrees F. minutes 23 seconds east (where E#B and F#D), and feeding information has not been inputted. In addition, the predetermined distance range in S2202 and S2301 is assumed to be plus or minus 2 seconds for both latitude and longitude. Since the earth is not a perfect sphere and distances per second differ depending on the latitude or longitude as well as the direction of measurement, in this case, the distance per second is assumed to be 30 m for purposes of simplification. Therefore, the predetermined distance range is plus or minus 60 m.

When swallowing is detected at the date/time and position described above, the accidental ingestion determining unit 1801 refers to the confirmation result information table to check whether there exists previous swallowing which had been detected within a predetermined time range (plus or minus 2 seconds) from A degrees E minutes 14 seconds north and C degrees F. minutes 23 seconds east that is the position where the swallowing had been detected or, in other words, within a range of A degrees E minutes 12 seconds north to A degrees E minutes 16 seconds north and C degrees F. minutes 21 seconds east to C degrees F. minutes 25 seconds east and which had been confirmed by the owner to be "not accidental ingestion". Since a result of a confirmation of "accidental ingestion" by the owner is recorded with respect to swallowing that had occurred at 14:08:18 on Mar. 18, 2013 in the confirmation result information 2001 in row 1 of the confirmation result information table shown in FIG. 21, no corresponding swallowing is found. Next, a result of a confirmation of "not accidental ingestion" by the owner is recorded with respect to swallowing that had occurred at 19:45:52 on Mar. 21, 2013 at a position of A degrees E minutes 15 seconds north and C degrees F. minutes 24 seconds east in the confirmation result information 2001 in row 2 of the confirmation result information table. A degrees E minutes 15 seconds north and C degrees F. minutes 24 seconds east that is the position where swallowing which had been confirmed to be "not accidental ingestion" is within the range described above of A degrees E minutes 12 seconds north to A degrees E minutes 16 seconds north and C degrees F. minutes 21 seconds east to C degrees F. minutes 25 seconds east. Therefore, since a corresponding swallowing "exists", the accidental ingestion determining unit 1801 determines that the current swallowing is "not accidental ingestion".

As shown, in addition to the configuration described in Embodiment 3, the accidental ingestion detecting system according to Embodiment 4 further includes a location positioning unit 1802 that measures a position of an accidental ingestion detecting apparatus 1800. The accidental ingestion detecting apparatus 1800 that is mounted to the animal detects swallowing by the animal, and a date/time of the occurrence of the swallowing and a date/time included in feeding information which is inputted using a feeding information inputting apparatus 701 that differs from the accidental ingestion detecting apparatus 1800 are compared with one another. When the date/times are within a predetermined time range, the detected swallowing is determined not to be accidental ingestion. On the other hand, when the date/times are not within a predetermined time range, a check is performed to determine whether there is "swallowing confirmed not to be accidental ingestion by the owner" within a predetermined distance range from a position where the current swallowing had occurred among previous confirmation results stored in a confirmation result storing unit 1803. When such swallowing exists, the detected swallowing is determined not to be accidental ingestion. On the other hand, a determination of accidental ingestion is made when such swallowing does not exist. Subsequently, a notifying unit 305 of the accidental ingestion detecting apparatus 1800 and a notifying apparatus 1203 that is a different apparatus from the accidental ingestion detecting apparatus 1800 notify an owner that accidental ingestion by the animal has occurred. Therefore, even if feeding information is not inputted using the feeding information inputting apparatus 701, a determination of accidental ingestion is not made if food or a treat is given at a roughly regular location. As a result, an accidental ingestion notification can be prevented from being needlessly made to the owner.

While the location positioning unit 1802 has been described to be a GPS sensor in the accidental ingestion detecting system according to the present embodiment, the location positioning unit 1802 is not limited thereto and positioning may be performed using a wireless communication system for which standards are formulated as, for example, the IEEE 802.11 series and the IEEE 802.15 series. Accordingly, it is expected that positioning of the accidental ingestion detecting apparatus 1800 can also be performed indoors.

In addition, in the present embodiment, the process of S1602 in FIG. 16 may be inserted between S1601 and S2202 shown in FIG. 22. In this case, even in a case where the time of the currently detected swallowing is not within a predetermined time range with respect to a feeding date/time indicated by feeding information, the currently detected swallowing is not determined to be accidental ingestion if confirmation result information 2001 indicating "not accidental ingestion" within the predetermined time range with respect to the time of the currently detected swallowing is stored in the confirmation result storing unit 1803.

Embodiment 5

Figure 24:
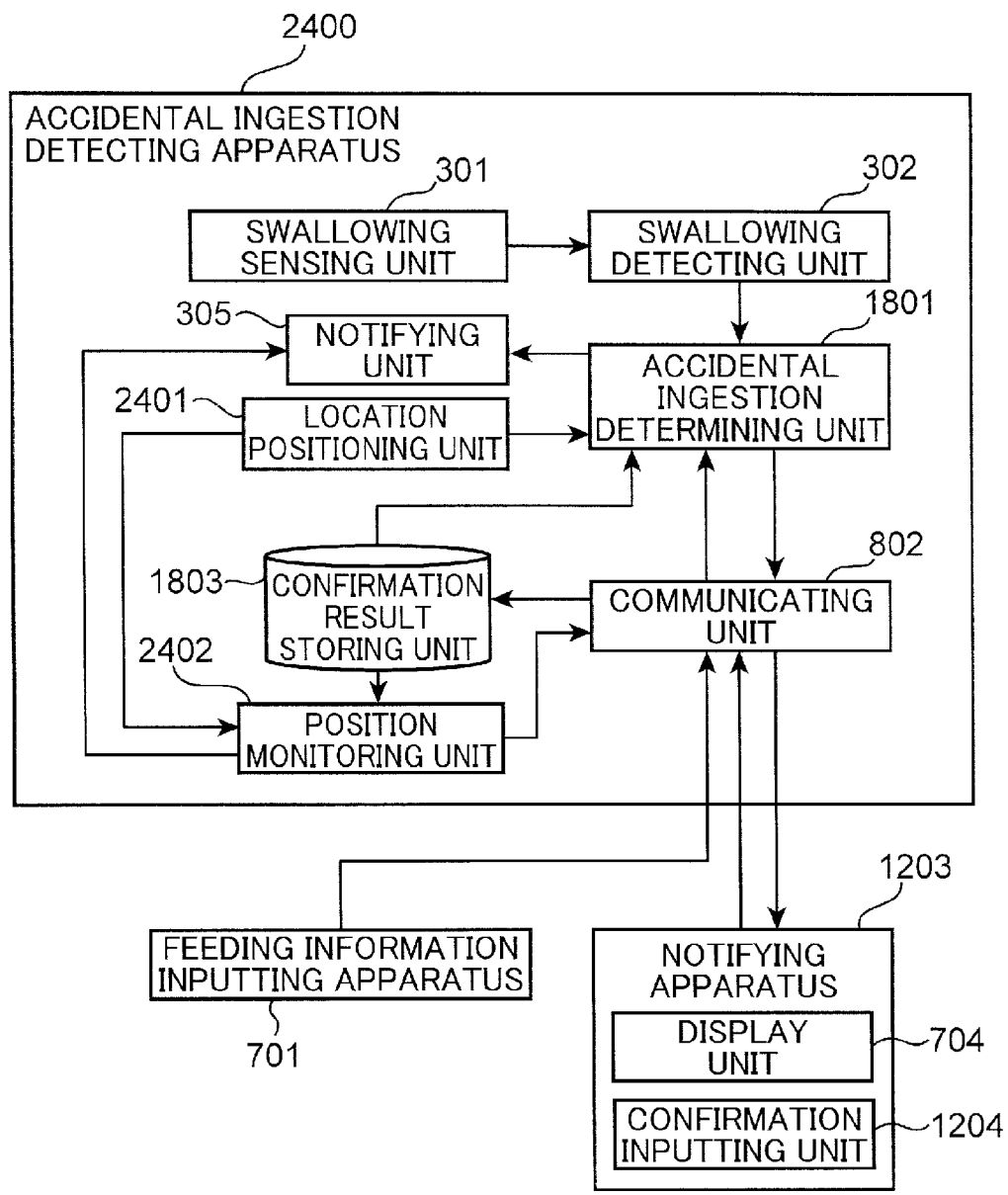
FIG. 24 is a block diagram showing a functional configuration of an accidental ingestion detecting system according to Embodiment 5.

FIG. 24 is a block diagram showing a functional configuration of an accidental ingestion detecting system according to Embodiment 5. In addition to the configuration described in Embodiment 4, the accidental ingestion detecting system according to Embodiment 5 further includes a position monitoring unit 2402 that monitors a position of an accidental ingestion detecting apparatus 2400.

The position monitoring unit 2402 receives input of positioning data from a location positioning unit 2401 and checks whether there is "swallowing confirmed to be accidental ingestion by the owner" within a predetermined distance range from a current position among previous confirmation result information 2001 stored in a confirmation result storing unit 1803. When corresponding swallowing exists, the possibility that accidental ingestion by an animal may occur is notified to the owner by a notifying unit 305 of the accidental ingestion detecting apparatus 2400 and a notifying apparatus 1203 that is a different apparatus from the accidental ingestion detecting apparatus 2400.

Although the owner of the animal can be careful so as to prevent an occurrence of accidental ingestion by the animal by hiding objects that are more likely to be accidentally ingested from the animal at home, since the owner cannot always be as careful outdoors or inside another house or building, the risk of accidental ingestion increases. Depending on the location, there may be a large number of objects that are more likely to be accidentally ingested. Therefore, the owner must be attentive in advance at a location where accidental ingestion had previously occurred so that accidental ingestion does not happen again. With the accidental ingestion detecting system according to present Embodiment 5, when the animal mounted with the accidental ingestion detecting apparatus 2400 approaches a location where the owner had previously inputted a confirmation result that "accidental ingestion has occurred", the possibility that accidental ingestion may occur is notified to the owner. Therefore, the owner can pay close attention so that the animal does not perform accidental ingestion when the animal approaches such a location.

As shown in FIG. 24, the accidental ingestion detecting system includes the accidental ingestion detecting apparatus 2400 that is mounted to an animal, the feeding information inputting apparatus 701, and the notifying apparatus 1203.

The accidental ingestion detecting apparatus 2400 includes a swallowing sensing unit 301, a swallowing detecting unit 302, an accidental ingestion determining unit 1801, a location positioning unit 2401, a confirmation result storing unit 1803, a notifying unit 305, a communicating unit 802, and a position monitoring unit 2402. Since blocks other than the location positioning unit 2401 and the position monitoring unit 2402 are the same as those of the accidental ingestion detecting apparatus 1800 of the accidental ingestion detecting system according to Embodiment 4, a description thereof will be omitted.

The location positioning unit 2401 is constituted by a positioning sensor in a similar manner to the location positioning unit 1802 according to Embodiment 4. In the present embodiment, the positioning sensor is a GPS sensor. The location positioning unit 2401 measures a current position of the accidental ingestion detecting apparatus 2400 and outputs positioning data to the accidental ingestion determining unit 1801 and to the position monitoring unit 2402.

Figure 25:
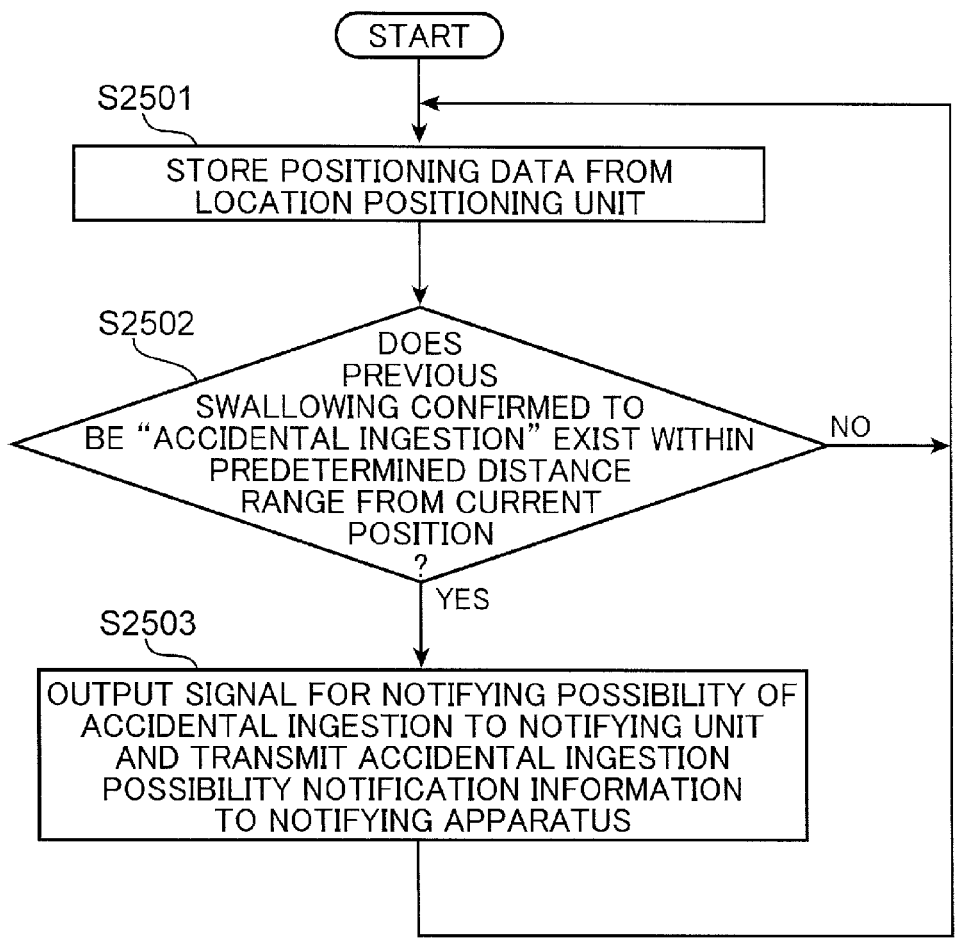
FIG. 25 is a flow chart showing an example of an operation of a position monitoring unit according to Embodiment 5.

FIG. 25 is a flow chart showing an example of an operation of the position monitoring unit 2402.

Upon receiving positioning data of the current position from the location positioning unit 2401 (S2501), the position monitoring unit 2402 refers to a confirmation result information table stored in the confirmation result storing unit 1803 and checks whether there exists confirmation result information 2001 related to "swallowing that is accidental ingestion" within a predetermined distance range from a position indicated by the positioning data (S2502). When corresponding confirmation result information 2001 does not exist (No in S2502), the accidental ingestion determining unit 1801 determines that there is no possibility of accidental ingestion and returns processing to awaiting reception (S2501) of positioning data. When corresponding confirmation result information 2001 exists (Yes in S2502), the accidental ingestion determining unit 1801 determines that there is a possibility of accidental ingestion. Subsequently, the accidental ingestion determining unit 1801 outputs a signal for notifying the possibility of accidental ingestion to the notifying unit 305 and transmits accidental ingestion possibility notification information for notifying the possibility of accidental ingestion to the notifying apparatus 1203 via the communicating unit 802 (S2503), and returns processing to awaiting reception (S2501) of positioning data.

For example, a case will be considered where the confirmation result information table shown in FIG. 21 is stored in the confirmation result storing unit 1803 and the accidental ingestion detecting apparatus 2400 is at a position of A degrees B minutes 32 seconds north and C degrees D minutes 35 seconds east at 15:03:24 on Mar. 22, 2013 (where B#E and D#F). In addition, the predetermined distance range in S2502 is assumed to be plus or minus 2 seconds for both latitude and longitude.

The location positioning unit 2401 of the accidental ingestion detecting apparatus 2400 outputs positioning data A degrees B minutes 32 seconds north and C degrees D minutes 35 seconds east to the position monitoring unit 2402. Upon receiving the positioning data, the position monitoring unit 2402 refers to the confirmation result information table to check whether there exists swallowing which had been detected within a predetermined distance range (plus or minus 2 seconds) from this position or, in other words, within a range of A degrees B minutes 30 seconds north to A degrees B minutes 34 seconds north and C degrees D minutes 33 seconds east to C degrees D minutes 37 seconds east and which had been confirmed by the owner to be "accidental ingestion". A result of swallowing which had been detected at A degrees B minutes 32 seconds north and C degrees D minutes 37 seconds east and which had been confirmed by the owner to be "accidental ingestion" is recorded in confirmation result information 2001 in row 1 of the confirmation result information table shown in FIG. 21. Since the position included in the confirmation result information 2001 is within the range described above of A degrees B minutes 30 seconds north to A degrees E minutes 34 seconds north and C degrees D minutes 33 seconds east to C degrees D minutes 37 seconds east, the position monitoring unit 2402 determines that corresponding swallowing "exists" and that "there is a possibility of accidental ingestion".

Figure 26:
FIG. 26 is a diagram showing an example of display content that is displayed by a notifying apparatus according to Embodiment 5.

FIG. 26 is a diagram showing an example of display contents that are displayed by the notifying apparatus 1203 having received accidental ingestion possibility notification information after a determination of "there is a possibility of accidental ingestion" had been made by the position monitoring unit 2402. As shown in FIG. 26, upon receiving accidental ingestion possibility notification information, the notifying apparatus 1203 notifies the possibility of accidental ingestion by the animal to the owner by causing a pop-up image 2601 to be displayed on the display unit 704 based on contents thereof. The pop-up image 2601 includes texts reading "Be aware of accidental ingestion by pet" and "Your pet is approaching a location of previous accidental ingestion". Therefore, the owner can be made aware of the possibility of accidental ingestion by the animal.

As shown, in addition to the configuration described in Embodiment 4, the accidental ingestion detecting system according to Embodiment 5 further includes a position monitoring unit 2402 that monitors a position of an accidental ingestion detecting apparatus 2400. When positioning data is inputted from a location positioning unit 2401, the position monitoring unit 2402 checks whether there is "swallowing confirmed to be accidental ingestion by the owner" within a predetermined distance range from a current position among previous confirmation result information 2001 stored in a confirmation result storing unit 1803. When corresponding swallowing exists, the possibility that accidental ingestion by an animal may occur is notified to the owner by a notifying unit 305 of the accidental ingestion detecting apparatus 2400 and a notifying apparatus 1203 that is a different apparatus from the accidental ingestion detecting apparatus 2400. Therefore, the owner can pay close attention so that the animal does not perform accidental ingestion when the animal approaches a location where accidental ingestion by the animal had previously occurred.

Moreover, contents of accidental ingestion possibility notification information are not particularly defined in the present embodiment and the notifying apparatus 1203 is configured so as to display the pop-up image 2601 shown in FIG. 26 upon reception of the accidental ingestion possibility notification information regardless of contents thereof. Therefore, the accidental ingestion possibility notification information has not been described by illustration. However, the present embodiment is not limited thereto. For example, the accidental ingestion possibility notification information may include information related to a distance between a current position of the accidental ingestion detecting apparatus 2400 and a position which is within a predetermined distance range from the current position and at which swallowing had previously occurred that had been confirmed by the owner to be "accidental ingestion". Subsequently, based on the accidental ingestion possibility notification information, the notifying apparatus 1203 causes the pop-up image 2601 displaying the distance between both positions to be displayed on the display unit 704. Accordingly, the owner's attention can be further aroused.

Embodiment 6

Figure 27:
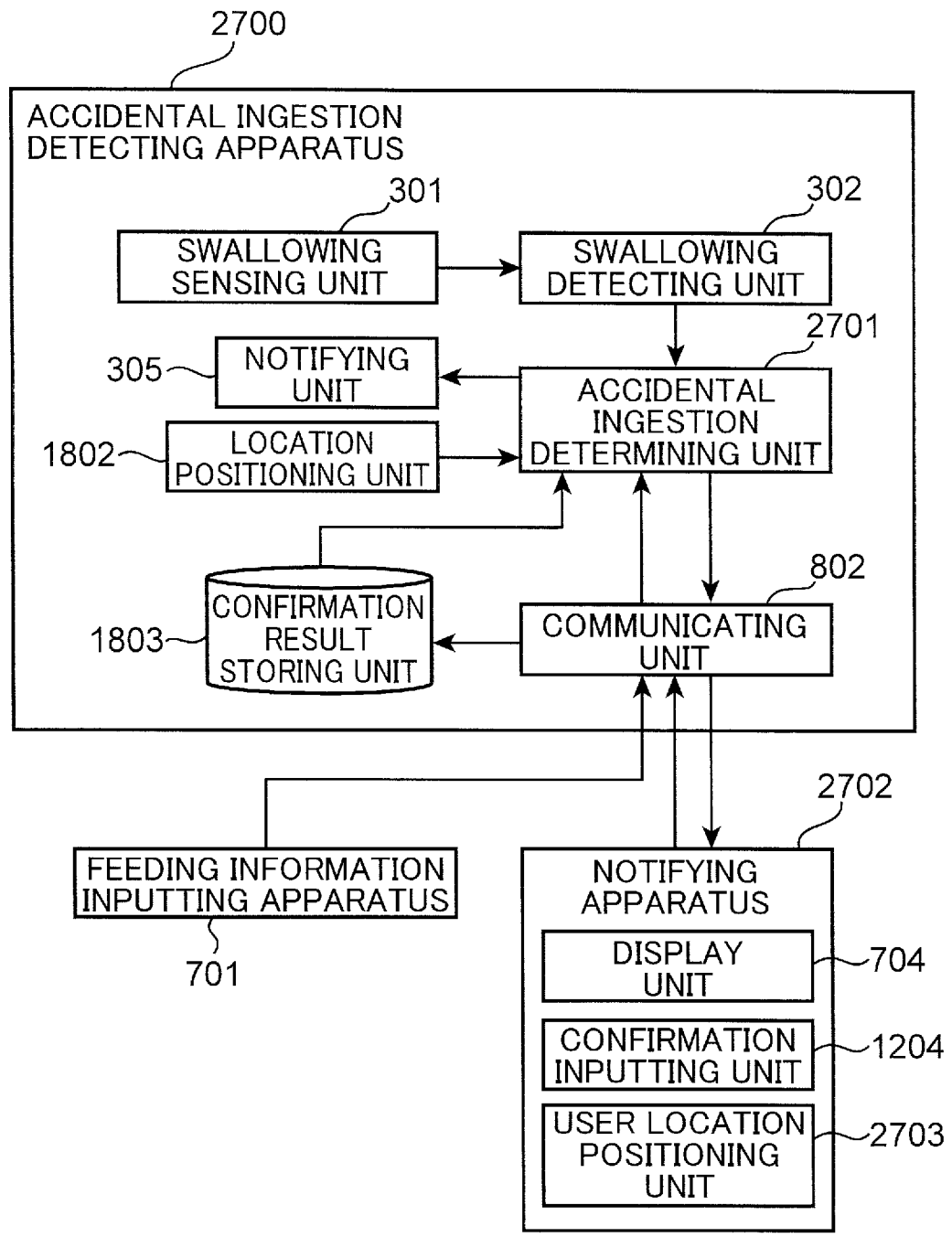
FIG. 27 is a block diagram showing a functional configuration of an accidental ingestion detecting system according to Embodiment 6.

FIG. 27 is a block diagram showing a functional configuration of an accidental ingestion detecting system according to Embodiment 6. In addition to the configuration described in Embodiment 4, the accidental ingestion detecting system according to Embodiment 6 further includes a user location positioning unit 2703 that measures a position of a notifying apparatus 2702.

When a swallowing detecting unit 302 detects swallowing by an animal, an accidental ingestion determining unit 2701 temporarily stores positioning data obtained from a location positioning unit 1802 and, at the same time, transmits a request to the notifying apparatus 2702 for acquiring user location positioning data that is positioning data with respect to a position of the notifying apparatus 2702 (in other words, a position of an owner holding the notifying apparatus 2702) and acquires user location positioning data from the notifying apparatus 2702. Next, based on positioning data at the time point where swallowing by the animal had been detected and on user positioning data, the accidental ingestion determining unit 2701 checks whether the distance between the accidental ingestion detecting apparatus 2700 and the notifying apparatus 2702 is within a predetermined distance range. When the distance between both apparatuses is within the predetermined distance range, the accidental ingestion determining unit 2701 determines that there is no possibility of accidental ingestion, and when the distance between both apparatuses is not within the predetermined distance range, the accidental ingestion determining unit 2701 continues performing determination of accidental ingestion.

With the accidental ingestion detecting system according to Embodiment 2, when the feeding information inputting apparatus 701 is an automatic feeder or the like, a determination of accidental ingestion is made when an owner manually feeds an animal food or a treat instead of using the automatic feeder. Even when the feeding information inputting apparatus 701 is constituted by an information processing device such as a mobile phone, a determination of accidental ingestion is made when input of feeding information before giving food or a treat to the animal is forgotten. Therefore, conceivably, the owner ends up receiving an excessive number of accidental ingestion notifications.

The accidental ingestion detecting system according to Embodiment 6 does not make a determination of accidental ingestion if a distance between the owner holding the notifying apparatus 2702 and an animal mounted with the accidental ingestion detecting apparatus 2700 is near. Therefore, an accidental ingestion notification can be prevented from being needlessly made to the owner.

As shown in FIG. 27, the accidental ingestion detecting system includes the accidental ingestion detecting apparatus 2700 that is mounted to an animal, the feeding information inputting apparatus 701, and the notifying apparatus 2702.

The accidental ingestion detecting apparatus 2700 includes a swallowing sensing unit 301, a swallowing detecting unit 302, an accidental ingestion determining unit 2701, a location positioning unit 1802, a confirmation result storing unit 1803, a notifying unit 305, and a communicating unit 802. Since respective units other than the accidental ingestion determining unit 2701 are the same as in the accidental ingestion detecting apparatus 1800 according to Embodiment 4, a description thereof will be omitted. Operations of the accidental ingestion determining unit 2701 will be described later.

Since the feeding information inputting apparatus 701 is the same as the feeding information inputting apparatus 701 in the accidental ingestion detecting system according to Embodiment 2, a description thereof will be omitted.

The notifying apparatus 2702 is, specifically, an information processing device such as a mobile phone. The notifying apparatus 2702 includes a communicating unit (not shown), a display unit 704 that is constituted by a liquid crystal display with a touch panel, a confirmation inputting unit 1204 that is used by the owner to input a confirmation result with respect to an accidental ingestion notification displayed on the display unit 704, and a user location positioning unit 2703 that measures a position of the notifying apparatus 2702. The user location positioning unit 2703 is constituted by a positioning sensor. In the present embodiment, a GPS sensor is used as the positioning sensor. The notifying apparatus 2702 transmits user location positioning data measured by the user location positioning unit 2703 to the accidental ingestion detecting apparatus 2700 in response to a request from the accidental ingestion detecting apparatus 2700.

Figure 28:
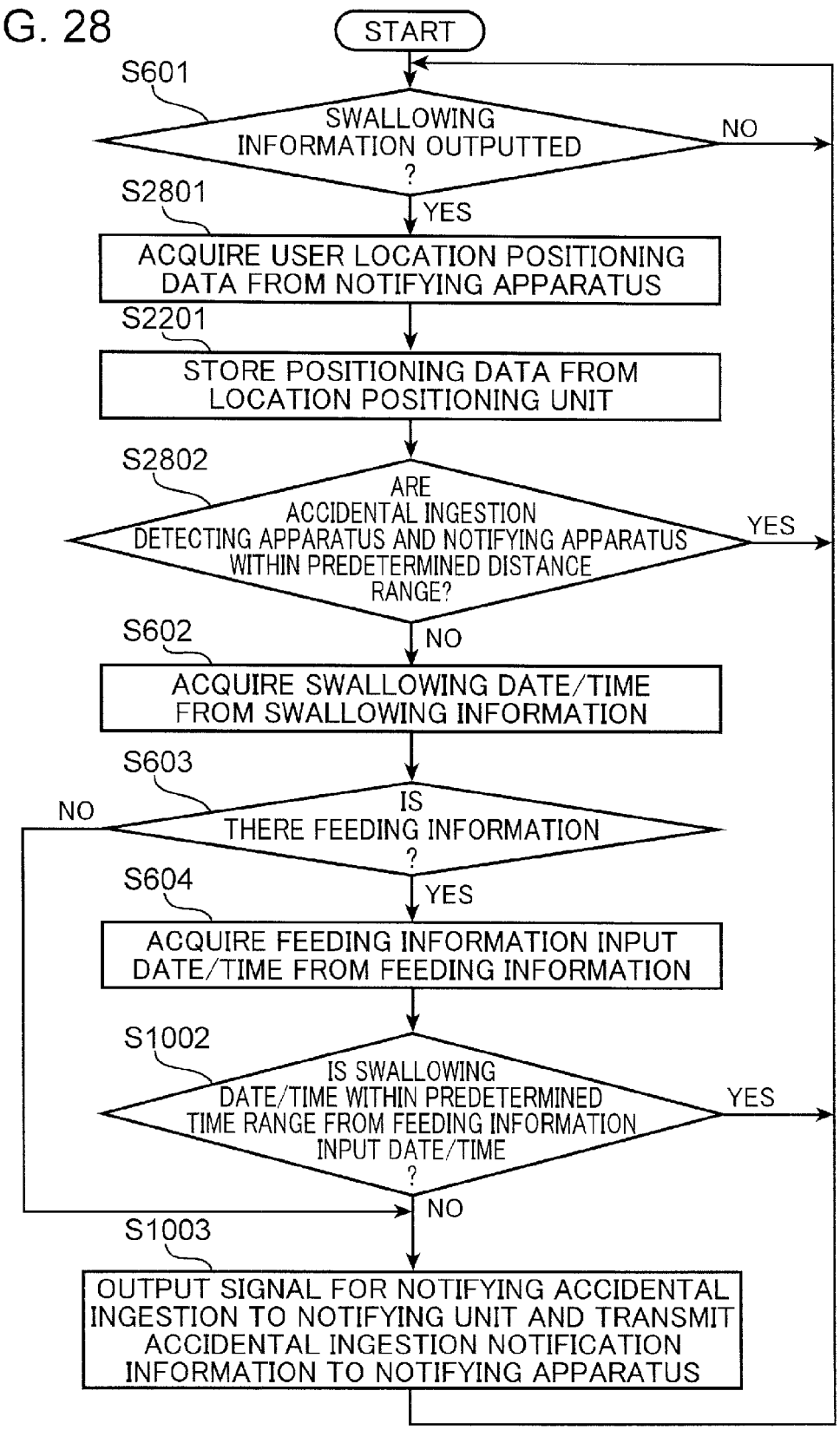
FIG. 28 is a flow chart showing an example of an operation of an accidental ingestion determining unit according to Embodiment 6.

FIG. 28 is a flow chart showing an example of an operation of the accidental ingestion determining unit 2701. Since steps other than S2801 and S2802 are the same as the respective steps in FIGS. 6, 10, and 22, a description thereof will be omitted.

In S2801, the accidental ingestion determining unit 2701 transmits an acquisition request for user location positioning data to the notifying apparatus 2702 via the communicating unit 802 and receives user location positioning data transmitted from the notifying apparatus 2702 via the communicating unit 802. In S2201, the accidental ingestion determining unit 2701 temporarily stores positioning data measured by the location positioning unit 1802. In addition, based on respective positioning data of the accidental ingestion detecting apparatus 2700 and the notifying apparatus 2702, the accidental ingestion determining unit 2701 checks whether a distance between both apparatuses is within a predetermined distance range (S2802). When the distance between both apparatuses is within a predetermined distance range (Yes in S2802), the accidental ingestion determining unit 2701 determines that there is no possibility of accidental ingestion and returns processing to monitoring (S601) of swallowing information. When the distance between both apparatuses is not within a predetermined distance range (No in S2802), the accidental ingestion determining unit 2701 continues a determination process with respect to whether or not the currently detected swallowing is accidental ingestion (S602 and thereafter).

Figure 29A:
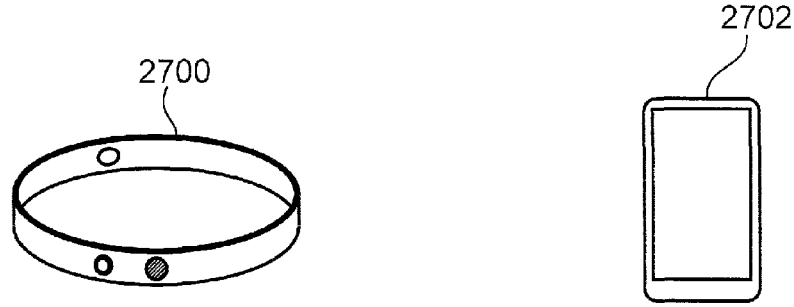
FIG. 29A is a diagram for specifically explaining an operation of the accidental ingestion determining unit according to Embodiment 6.
Figure 29B:
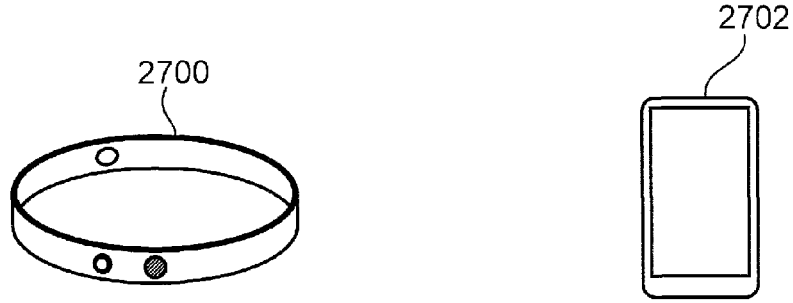
FIG. 29B is a diagram for specifically explaining an operation of the accidental ingestion determining unit according to Embodiment 6.

For example, a case will be considered where positioning data of the accidental ingestion detecting apparatus 2700 and the notifying apparatus 2702 is as shown in FIGS. 29A and 29B. In addition, the predetermined distance range in S2802 is assumed to be plus or minus 0.02 seconds (approximately 60 cm) for both latitude and longitude.

In FIG. 29A, a position where the accidental ingestion detecting apparatus 2700 had detected swallowing is A degrees B minutes 32.08 seconds north and C degrees D minutes 37.06 seconds east, and a position of the notifying apparatus 2702 at that time is A degrees B minutes 32.51 seconds north and C degrees D minutes 37.05 seconds east. Since the distance between both apparatuses at this time is 0.43 seconds in a latitude direction and 0.01 seconds in a longitude direction, the distance in the latitude direction does not fall within the predetermined distance range of 0.02 seconds. Therefore, the accidental ingestion determining unit 2701 continues the accidental ingestion determination process.

On the other hand, in FIG. 29B, a position where the accidental ingestion detecting apparatus 2700 had detected swallowing is A degrees B minutes 32.08 seconds north and C degrees D minutes 37.06 seconds east, and a position of the notifying apparatus 2702 at that time is A degrees B minutes 32.09 seconds north and C degrees D minutes 37.05 seconds east. Since the distance between both apparatuses at this time is 0.01 seconds in a latitude direction and 0.01 seconds in a longitude direction, the distance in both the latitude direction and the longitude direction falls within the predetermined distance range of 0.02 seconds. Therefore, the accidental ingestion determining unit 2701 determines that there is no possibility of accidental ingestion.

As shown, in addition to the configuration described in Embodiment 4, the accidental ingestion detecting system according to Embodiment 6 further includes a user location positioning unit 2703 that measures a position of a notifying apparatus 2702. When an accidental ingestion detecting apparatus 2700 mounted to an animal detects swallowing by the animal, an accidental ingestion determining unit 2701 temporarily stores positioning data obtained from a location positioning unit 1802 and, at the same time, transmits a request to the notifying apparatus 2702 for acquiring user location positioning data that is positioning data with respect to a position (in other words, a position of an owner holding the notifying apparatus 2702) from the notifying apparatus 2702 and acquires user location positioning data from the notifying apparatus 2702. Next, based on positioning data of the location positioning unit 1802 at the time point where swallowing by the animal had been detected and on user positioning data acquired from the notifying apparatus 2702, the accidental ingestion determining unit 2701 checks whether the distance between the accidental ingestion detecting apparatus 2700 and the notifying apparatus 2702 is within a predetermined distance range. When the distance between both apparatuses is within the predetermined distance range, the accidental ingestion determining unit 2701 determines that there is no possibility of accidental ingestion, and when the distance between both apparatuses is not within the predetermined distance range, the accidental ingestion determining unit 2701 continues performing determination of accidental ingestion. Therefore, an accidental ingestion notification can be prevented from being needlessly made to the owner.

Moreover, with the accidental ingestion detecting system according to the present embodiment, the location positioning unit 1802 and the user location positioning unit 2703 have been described as being GPS sensors, this configuration is not restrictive. For example, positioning may be performed using wireless communication (for example, using a wireless communication system for which standards are formulated as, for example, the IEEE 802.11 series and the IEEE 802.15 series) which is assumed as communicating units of the accidental ingestion detecting apparatus 2700 and the notifying apparatus 2702. Alternatively, a distance between the accidental ingestion detecting apparatus 2700 and the notifying apparatus 2702 (a user holding the notifying apparatus 2702) may be measured based on radio field intensity of wireless communication. Accordingly, the determination process can also be performed indoors.

Figure 40:
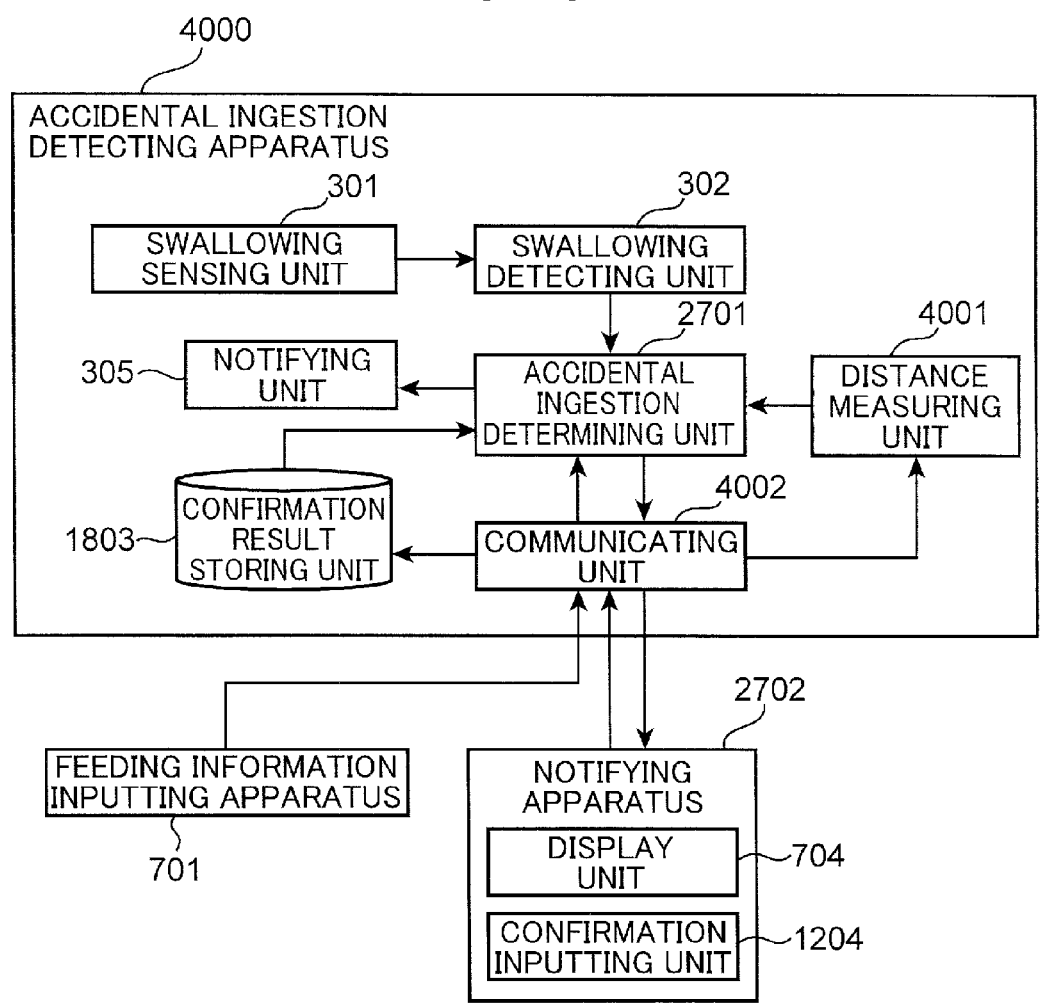
FIG. 40 is a block diagram showing a functional configuration of a modification of the accidental ingestion detecting system according to Embodiment 6.

The accidental ingestion detecting system in this case may be configured as shown in FIG. 40. FIG. 40 is a block diagram showing a functional configuration of an accidental ingestion detecting system according to a modification of Embodiment 6.

An accidental ingestion detecting apparatus 4000 is provided with a distance measuring unit 4001 and a communicating unit 4002 in place of the location positioning unit 1802 and the communicating unit 802 in the accidental ingestion detecting apparatus 2700 shown in FIG. 27. In addition, the user location positioning unit 2703 has been omitted from the notifying apparatus 2702 shown in FIG. 27.

The communicating unit 4002 is constituted by, for example, a wireless communication apparatus conforming to standards of the IEEE 802.11 series or the IEEE 802.15 series.

The distance measuring unit 4001 detects an intensity of a radio wave which is transmitted from the notifying apparatus 2702 and which is received by the communicating unit 4002 and, based on the detected intensity of the radio wave, measures a distance between the accidental ingestion detecting apparatus 4000 and the notifying apparatus 1203 as a distance between users holding the accidental ingestion detecting apparatus 4000 and the notifying apparatus 2702. In addition, the distance measuring unit 4001 notifies the measured distance to the accidental ingestion determining unit 2701. In this case, the distance measuring unit 4001 may regularly measure the distance between the accidental ingestion detecting apparatus 4000 and the notifying apparatus 2702.

Furthermore, the distance measuring unit 4001 may retain a distance conversion table which defines, in advance, a relationship between radio field intensity and a distance between the accidental ingestion detecting apparatus 4000 and the notifying apparatus 1203, and may measure a distance between the accidental ingestion detecting apparatus 4000 and the notifying apparatus 1203 using the distance conversion table.

Moreover, when the distance between the accidental ingestion detecting apparatus 4000 and the notifying apparatus 1203 is equal to or greater than a communicable distance according to the wireless communication standard described above, the communicating unit 4002 cannot notify radio field intensity to the distance measuring unit 4001. In this case, for example, the distance measuring unit 4001 may notify information indicating that the accidental ingestion detecting apparatus 4000 and the notifying apparatus 1203 are outside the communication range to the accidental ingestion determining unit 2701.

When swallowing by an animal is detected by the swallowing detecting unit 302, the accidental ingestion determining unit 2701 makes a determination of Yes in S2802 if the distance between the accidental ingestion detecting apparatus 4000 and the notifying apparatus 2702 as measured by the distance measuring unit 4001 within a certain period (a period considered to be substantially simultaneous such as 1 to 10 seconds) from the time of detection is within a predetermined distance range, and makes a determination of No in S2802 if not within a predetermined distance range.

In addition, while the user location positioning unit 2703 that measures a position of the owner has been described as being included in the notifying apparatus 2702 in the present embodiment, this configuration is not restrictive. For example, any positioning apparatus can be adopted as the user location positioning unit 2703 as long as the apparatus is a separate apparatus from the notifying apparatus 2702, can be constantly worn by the owner, and is capable of communicating with the accidental ingestion detecting apparatus 2700.

Furthermore, while the present embodiment is configured such that a distance between two points of the accidental ingestion detecting apparatus 2700 and the notifying apparatus 2702 is separately obtained for a latitude direction and a longitude direction and conditions are satisfied when both values are within a predetermined distance range in order to simplify description, a distance between two points may be obtained using the Hubeny formula, the Andoyer-Lambert formula, or the like on the basis of the latitude and longitude values of two points.

Embodiment 7

Figure 30:
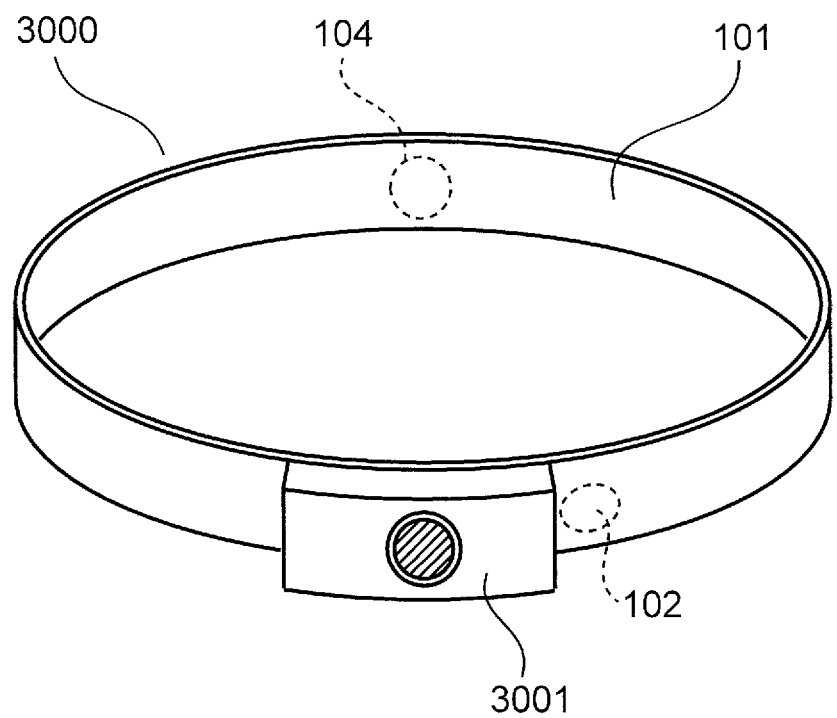
FIG. 30 is a diagram showing an appearance of an accidental ingestion detecting apparatus according to Embodiment 7.
Figure 31:
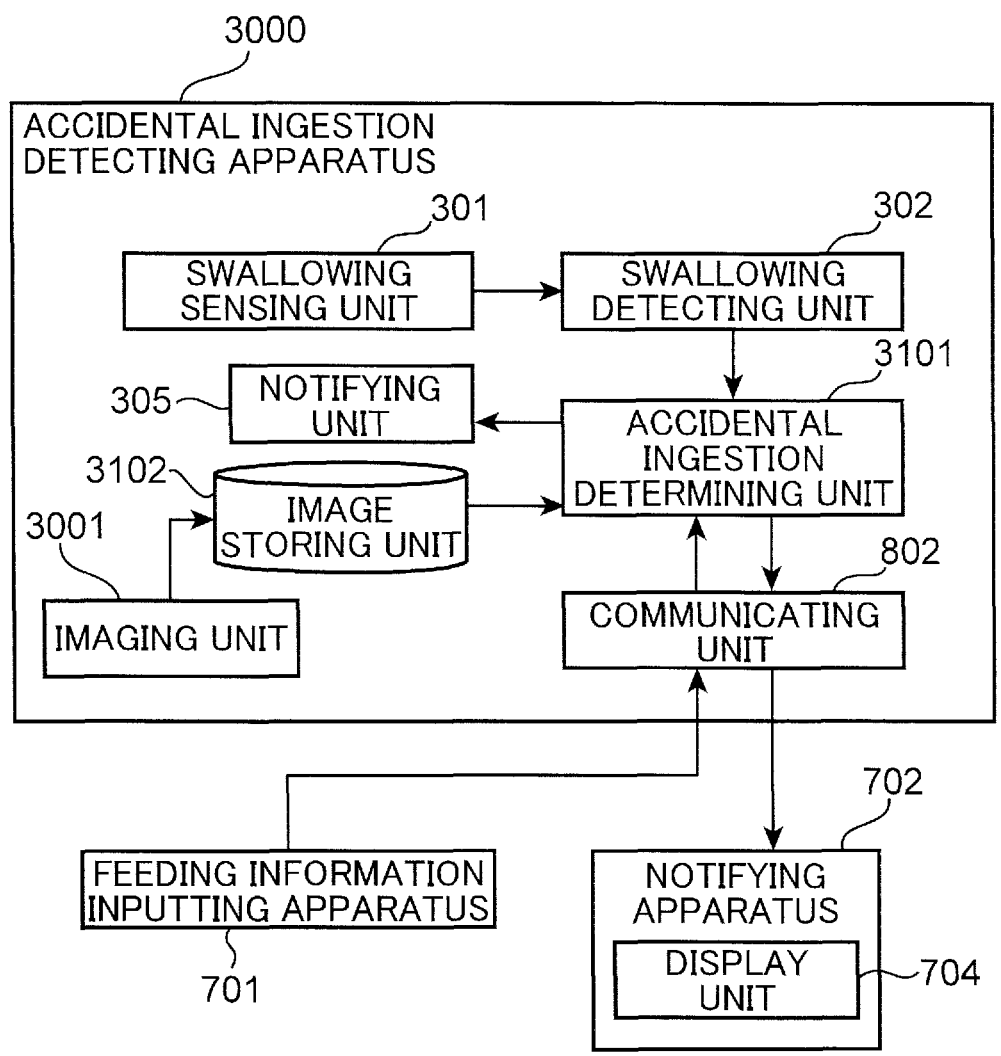
FIG. 31 is a block diagram showing a functional configuration of an accidental ingestion detecting system according to Embodiment 7.

FIG. 30 is a diagram showing an example of an appearance of an accidental ingestion detecting apparatus 3000 in an accidental ingestion detecting system according to Embodiment 7. FIG. 31 is a block diagram showing a functional configuration of an accidental ingestion detecting system according to Embodiment 7.

In addition to the configuration described in Embodiment 2, the accidental ingestion detecting system according to Embodiment 7 further includes an imaging unit 3001 that captures an image of a vicinity of the accidental ingestion detecting apparatus 3000 and an image storing unit 3102 that stores a predetermined amount of images captured by the imaging unit 3001.

The imaging unit 3001 captures still images at a predetermined time interval and outputs image data to the image storing unit 3102. Upon receiving outputted image data, the image storing unit 3102 stores the image data in an internal storage area. In this case, an upper limit of the number of pieces of image data to be stored is set to a predetermined number, and when new image data is inputted after the number of pieces of image data has reached the upper limit, the image storing unit 3102 deletes the oldest image data.

Upon detecting swallowing by an animal, a swallowing detecting unit 302 compares a date/time of the occurrence of the swallowing with a date/time included in feeding information which is inputted using a feeding information inputting apparatus 701. When the date/times are within a predetermined time range, an accidental ingestion determining unit 3101 determines that the detected swallowing is not accidental ingestion. On the other hand, the accidental ingestion determining unit 3101 makes a determination of accidental ingestion when the date/times are not within a predetermined time range and notifies that accidental ingestion by an animal has occurred to an owner through a notifying unit 305 of the accidental ingestion detecting apparatus 3000 and a notifying apparatus 702. In doing so, by transmitting a predetermined number of pieces of image data in a reverse chronological order to the notifying apparatus 702 through the communicating unit 802 among the image data stored in the image storing unit 3102, the accidental ingestion determining unit 3101 causes the notifying apparatus 702 to display "images before and after the occurrence of accidental ingestion by the animal".

With the accidental ingestion detecting system according to present Embodiment 7, when receiving an accidental ingestion notification from the accidental ingestion detecting system, the owner can confirm whether an object swallowed by the animal was food by checking an image captured at a time point slightly preceding the detection of accidental ingestion. In addition, by showing the image to a veterinarian, the owner can provide material for the veterinarian's consideration with respect to what kind of treatment should be performed (would vomiting be enough, is removal using an endoscope necessary, or the like).

As shown in FIG. 30, the accidental ingestion detecting apparatus 3000 includes a collar-type main body unit 101 mounted to an animal, a sound pickup sensor 102, a display apparatus 104, and an imaging unit 3001. The imaging unit 3001 includes an imaging lens and an imaging element, and captures an image and generates image data. The accidental ingestion detecting apparatus 3000 is mounted to the animal so that the imaging unit 3001 faces forward as seen from the animal. Accordingly, the sound pickup sensor 102 can be brought into close contact with a neck area of the animal to collect a swallowing sound at the neck area, and the imaging unit 3001 can capture an image of the front of the animal immediately before the animal performs swallowing. Moreover, it is assumed that an orientation of an optical axis of the imaging lens is adjusted so that when the animal tries to hold an object in the mouth, the object is captured by the imaging element.

As shown in FIG. 31, the accidental ingestion detecting system includes the accidental ingestion detecting apparatus 3000 that is mounted to an animal, a feeding information inputting apparatus 701, and the notifying apparatus 702.

The accidental ingestion detecting apparatus 3000 includes a swallowing sensing unit 301, a swallowing detecting unit 302, an accidental ingestion determining unit 3101, the notifying unit 305, the communicating unit 802, the imaging unit 3001, and the image storing unit 3102. Since respective units other than the accidental ingestion determining unit 3101, the imaging unit 3001, and the image storing unit 3102 are the same as in the accidental ingestion detecting apparatus 700 according to Embodiment 2, a description thereof will be omitted. Operations of the accidental ingestion determining unit 3101 will be described later.

The imaging unit 3001 captures images at a predetermined time interval and outputs image data to the image storing unit 3102. In the present embodiment, the time interval at which the imaging unit 3001 captures images is set to 1 second.

Upon receiving image data outputted from the imaging unit 3001, the image storing unit 3102 stores the image data in an internal storage area. In the present embodiment, an upper limit of the number of pieces of image data internally stored by the image storing unit 3102 is set to, for example, 20.

Since the feeding information inputting apparatus 701 is the same as the feeding information inputting apparatus 701 in the accidental ingestion detecting system according to Embodiment 2, a description thereof will be omitted.

While the notifying apparatus 702 shares the same functions as the notifying apparatus 702 in the accidental ingestion detecting system according to Embodiment 2, display contents when notifying accidental ingestion differ from Embodiment 2. The display contents will be described later.

Figure 32:
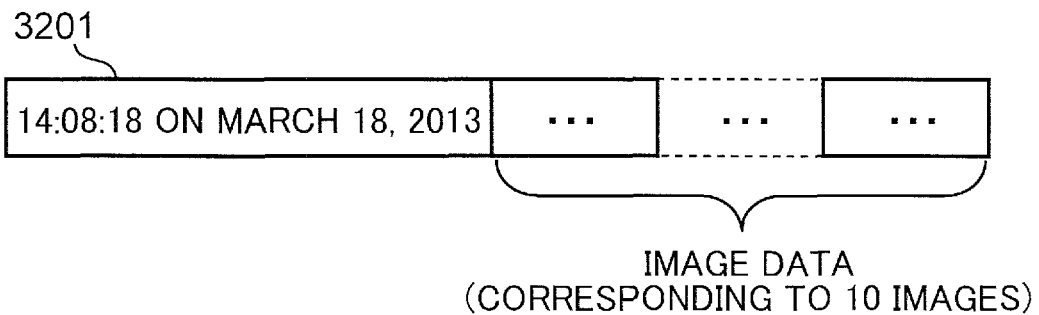
FIG. 32 is a diagram showing an example of accidental ingestion notification information according to Embodiment 7.

FIG. 32 is a diagram showing an example of accidental ingestion notification information 3201. As shown in FIG. 32, the accidental ingestion notification information 3201 includes information on a date/time of detection of swallowing that had been determined to be accidental ingestion and a predetermined number of pieces of image data in a reverse chronological order among image data stored in the image storing unit 3102 at the time point of determination of accidental ingestion. In present Embodiment 7, the number of pieces of image data included in accidental ingestion notification information is set to, for example, 10. In other words, image data from the time point of detection of swallowing to 10 seconds prior thereto is transmitted to the notifying apparatus 702 as accidental ingestion notification information 3201.

Figure 33:
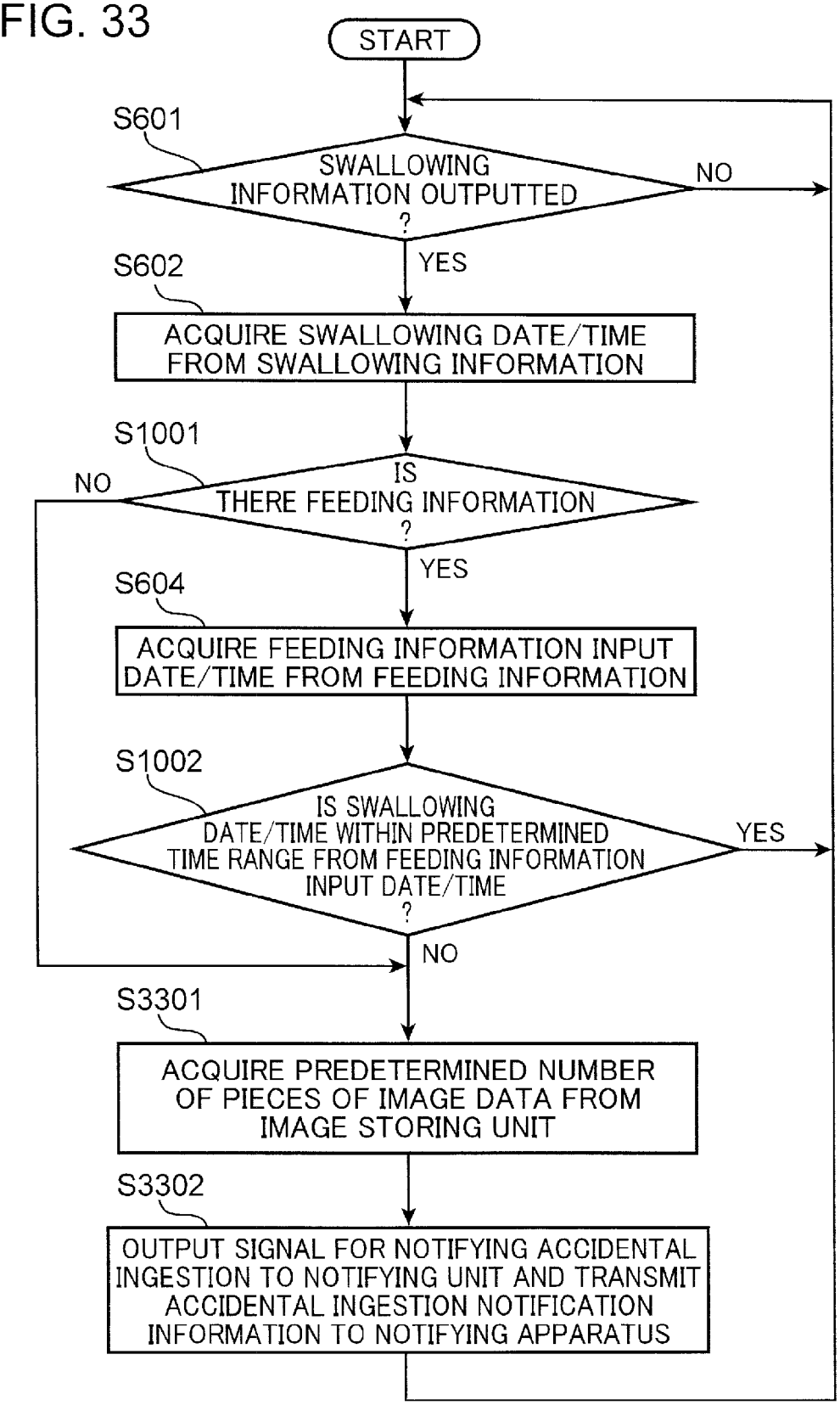
FIG. 33 is a flow chart showing an example of an operation of an accidental ingestion determining unit according to Embodiment 7.

FIG. 33 is a flow chart showing an example of an operation of the accidental ingestion determining unit 3101. Since steps other than S3301 and S3302 are the same as operations in the respective steps in FIG. 10 that shows operations according to Embodiment 2, a description thereof will be omitted.

When No or, in other words, accidental ingestion is determined in S1002, the accidental ingestion determining unit 3101 acquires a predetermined number of pieces of image data in a reverse chronological order of storage from the image storing unit 3102 (S3301). Next, the accidental ingestion determining unit 3101 generates accidental ingestion notification information 3201 based on information on a date/time of detection of swallowing and the image data acquired in S3301 and transmits the accidental ingestion notification information 3201 to the notifying apparatus 702 via the communicating unit 802 and, at the same time, outputs a signal for notifying accidental ingestion to the notifying unit 305 (S3302).

Figure 34:
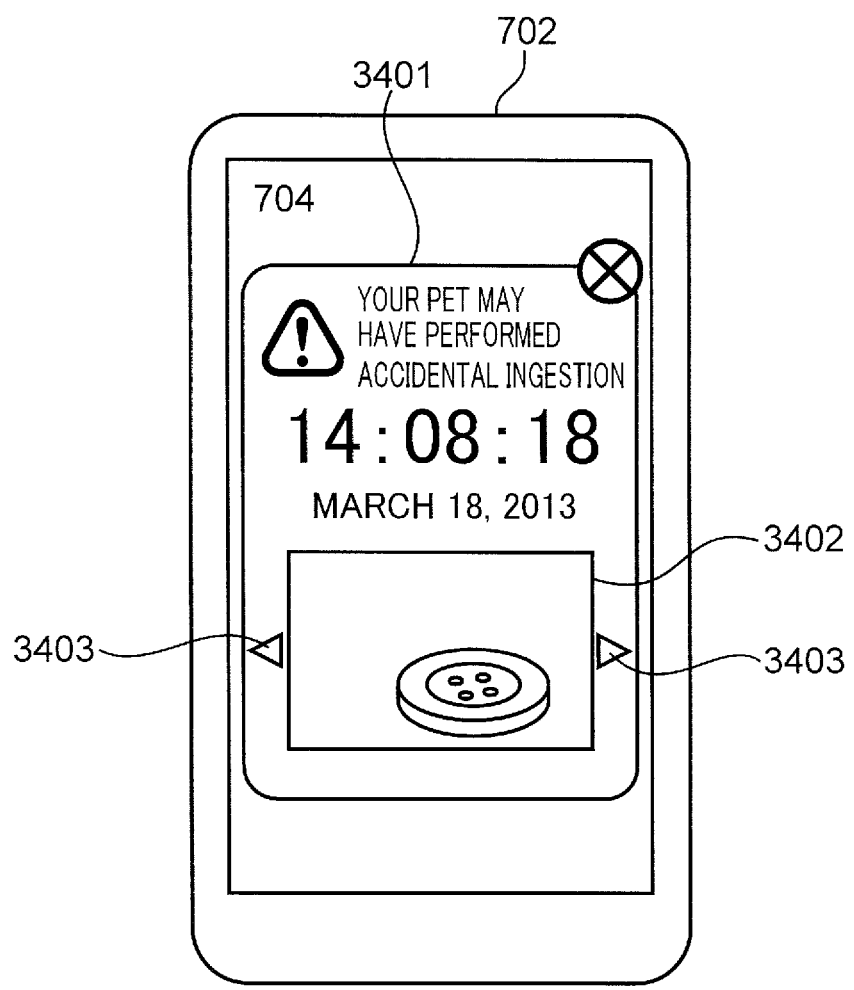
FIG. 34 is a diagram showing an example of display content that is displayed by a notifying apparatus according to Embodiment 7.

FIG. 34 is a diagram showing an example of a pop-up image 3401 that is displayed by the notifying apparatus 702 having received accidental ingestion notification information. As shown in FIG. 34, upon receiving accidental ingestion notification information 3201, the notifying apparatus 702 generates the pop-up image 3401 using the accidental ingestion notification information 3201 and displays the pop-up image 3401 on the display unit 704. Accordingly, accidental ingestion by the animal is notified to the owner. In the example shown in FIG. 34, a pop-up image 3401 is displayed which includes "14:08:18 on Mar. 18, 2013" and image data that are recorded in the accidental ingestion notification information 3201 shown in FIG. 32.

Specifically, in addition to a display field of the fact that accidental ingestion has occurred and the date/time of occurrence of the accidental ingestion, the pop-up image 3401 is further provided with an image display field 3402. Image data included in the accidental ingestion notification information 3201 is displayed in the image display field 3402. A pair of frame-by-frame buttons 3403 is provided to the left and right of the image display field 3402. When the left-side frame-by-frame button 3403 is pressed by the owner, the notifying apparatus 702 causes image data of 1 frame prior to the image data currently being displayed in the image display field 3402 to be displayed in the image display field 3402. On the other hand, when the right-side frame-by-frame button 3403 is pressed by the owner, the notifying apparatus 702 causes image data of 1 frame subsequent to the image data currently being displayed in the image display field 3402 to be displayed in the image display field 3402. Therefore, by pressing the left and right frame-by-frame buttons 3403, the owner can confirm actions related to swallowing by the animal for a period from the time point of detection of swallowing to a certain time point prior thereto.

In addition, when the owner brings a finger into contact with the image display field 3402 and slides the finger rightward, the notifying apparatus 702 causes image data of 1 frame prior to the image data currently being displayed in the image display field 3402 to be displayed in the image display field 3402. On the other hand, when the owner brings a finger into contact with the image display field 3402 and slides the finger leftward, the notifying apparatus 702 causes image data of 1 frame subsequent to the image data currently being displayed in the image display field 3402 to be displayed in the image display field 3402. Therefore, by bringing a finger into contact with the image display field 3402 and moving the finger to the left or right, the owner can confirm actions related to swallowing by the animal for a period from the time point of detection of swallowing to a certain time point prior thereto. In the example shown in FIG. 34, since an image of a button is displayed in the image display field 3402, the owner can determined that the animal has accidentally ingested a button.

As shown, in addition to the configuration described in Embodiment 2, the accidental ingestion detecting system according to Embodiment 7 further includes an imaging unit 3001 that captures an image of a vicinity of the accidental ingestion detecting apparatus 3000 and an image storing unit 3102 that stores a predetermined amount of images captured by the imaging unit 3001. When swallowing by an animal is detected by an accidental ingestion detecting apparatus 3000 that is mounted to the animal, a date/time of the occurrence of the swallowing and a date/time included in feeding information which is inputted using a feeding information inputting apparatus 701 are compared to one another. When the date/times are within a predetermined time range, the detected swallowing is determined not to be accidental ingestion. However, when the date/times are not within a predetermined time range, a determination of accidental ingestion is made. Subsequently, the accidental ingestion by the animal is notified to the owner through a notifying unit 305 of the accidental ingestion detecting apparatus 3000 and a notifying apparatus 702 that is a different apparatus from the accidental ingestion detecting apparatus 3000. In doing so, a predetermined number of pieces of image data in a reverse chronological order among image data stored in the image storing unit 3102 is transmitted from the accidental ingestion detecting apparatus 3000 to the notifying apparatus 702. In addition, "images before and after the accidental ingestion by the animal" are displayed by the notifying apparatus 702. Accordingly, the owner can confirm whether an object that had been swallowed by the animal is food.

Moreover, while images which are captured by the imaging unit 3001 and stored in the image storing unit 3102 have been described as still images in the accidental ingestion detecting system according to the present embodiment, the images may alternatively be moving images. In this case, the predetermined amount of images to be stored in the image storing unit 3102 may be defined by time. For example, the predetermined amount is defined as a moving image of 60 seconds.

In this case, there is a possibility that a data amount of the accidental ingestion notification information 3201 may become excessively large when moving image data is included in accidental ingestion notification information 3201. In consideration thereof, instead of moving image data, the accidental ingestion notification information 3201 may include a uniform resource locator (URL) indicating a storage location of image data for streaming reproduction of the moving image data. In addition, when the owner inputs an access instruction for the URL to the notifying apparatus 702, the accidental ingestion detecting apparatus 3000 may transmit the image data for streaming reproduction that is stored at the URL to the notifying apparatus 702. Furthermore, the image storing unit 3102 may be realized by an information processing device (such as a home server device or a server device on the Internet) that is separate from the accidental ingestion detecting apparatus 3000.

In addition, in the present embodiment, the accidental ingestion determining unit 3101 may perform a determination of accidental ingestion in consideration of confirmation result information stored in the confirmation result storing unit 1803 in a similar manner to the accidental ingestion determining unit 1201 shown in FIG. 12. In this case, the accidental ingestion detecting apparatus 3000 may be further provided with the confirmation result storing unit 1202 shown in FIG. 12.

Embodiment 8

Figure 35:
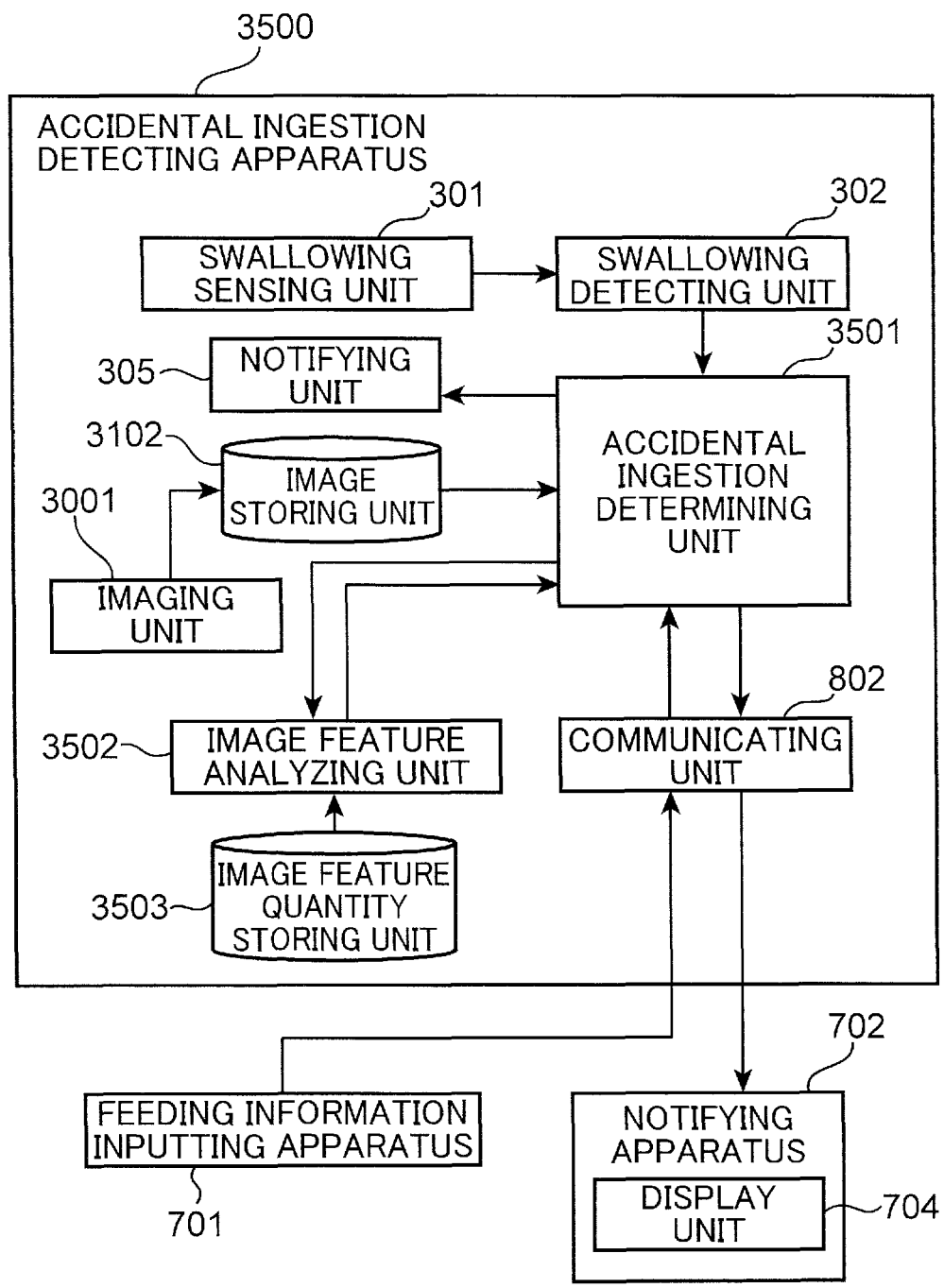
FIG. 35 is a block diagram showing a functional configuration of an accidental ingestion detecting system according to Embodiment 8.

FIG. 35 is a block diagram showing a functional configuration of an accidental ingestion detecting system according to Embodiment 8. In addition to the configuration described in Embodiment 7, the accidental ingestion detecting system according to Embodiment 8 further includes an image feature analyzing unit 3502 which analyzes image data to extract a feature quantity and compares the feature quantity with a feature quantity that is stored in an image feature quantity storing unit 3503, and the image feature quantity storing unit 3503 that stores image feature quantities.

When a swallowing detecting unit 302 detects swallowing by an animal, the accidental ingestion determining unit 3501 compares a date/time of the occurrence of the swallowing with a date/time included in feeding information which is inputted using a feeding information inputting apparatus 701. When the date/times are within a predetermined time range, the accidental ingestion determining unit 3501 determines that the detected swallowing is not accidental ingestion. On the other hand, when the date/times are not within a predetermined time range, the accidental ingestion determining unit 3501 determines that there is a possibility of accidental ingestion, acquires a predetermined number of pieces of image data in a reverse chronological order among image data stored in the image storing unit 3102, and outputs the acquired image data to the image feature analyzing unit 3502. By subjecting the image data to image analysis, the image feature analyzing unit 3502 extracts a feature quantity of the image data. In addition, the image feature analyzing unit 3502 compares the feature quantity obtained as a result of the analysis with a feature quantity stored in advance in the image feature quantity storing unit 3503 and outputs a comparison result to the accidental ingestion determining unit 3501. In this case, when a currently obtained feature quantity is equal to or only differs slightly from any of the feature quantities stored in the image feature quantity storing unit 3503, the image feature analyzing unit 3502 determines that the detected swallowing is not accidental ingestion. On the other hand, when a difference between feature quantities is not sufficiently small, the image feature analyzing unit 3502 determines that the detected swallowing is accidental ingestion. Subsequently, upon receiving a comparison result of accidental ingestion, the accidental ingestion determining unit 3501 notifies the owner that an accidental ingestion by the animal has occurred through the notifying unit 305 of the accidental ingestion detecting apparatus 3500 and the notifying apparatus 702.

With the accidental ingestion detecting system according to Embodiment 2, when the feeding information inputting apparatus 701 is an automatic feeder or the like, a determination of accidental ingestion is made when an owner manually feeds an animal food or a treat instead of using the automatic feeder. Even when the feeding information inputting apparatus 701 is constituted by an information processing device such as a mobile phone, a determination of accidental ingestion is made when input of feeding information before giving food or a treat to the animal is forgotten. Therefore, conceivably, the owner ends up receiving an excessive number of accidental ingestion notifications.

With the accidental ingestion detecting system according to Embodiment 8, a determination of accidental ingestion is not made when the owner or food that has been registered in advance appear in an image captured during a period from the time point of detection of swallowing to a time point slightly prior thereto. Therefore, an accidental ingestion notification is prevented from being needlessly made to the owner.

As shown in FIG. 35, the accidental ingestion detecting system includes the accidental ingestion detecting apparatus 3500 that is mounted to an animal, the feeding information inputting apparatus 701, and the notifying apparatus 702.

The accidental ingestion detecting apparatus 3500 includes a swallowing sensing unit 301, a swallowing detecting unit 302, an accidental ingestion determining unit 3501, the notifying unit 305, the communicating unit 802, the imaging unit 3001, the image storing unit 3102, the image feature analyzing unit 3502, and the image feature quantity storing unit 3503. Since respective units other than the accidental ingestion determining unit 3501, the image feature analyzing unit 3502, and the image feature quantity storing unit 3503 are the same as the respective units in the accidental ingestion detecting apparatus 3000 according to Embodiment 7, a description thereof will be omitted. Operations of the accidental ingestion determining unit 3501 will be described later.

The image feature analyzing unit 3502 receives the predetermined number of pieces of image data which the accidental ingestion determining unit 3501 had acquired from the image storing unit 3102, performs image analysis on each piece of image data, and extracts an image feature quantity. Specifically, the image feature analyzing unit 3502 detects an object included in image data and extracts a feature quantity of the detected object. Examples of objects include specific items such as a human face and food.

Since a feature quantity extraction technique for extracting a feature quantity of an object and an object area detection technique for checking whether an object appears in content are well known, a detailed description will not be given. For example, when the object is a face, a distance between the eyes or a width of the nose may be adopted as a feature quantity of the face. Alternatively, a pattern distribution of colors or shades of the surface of the face may be adopted as a feature quantity of the face. In addition, detection of a facial area may be performed with a classifier such as a support vector machine (SVM) or AdaBoost using these feature quantities as input. Extraction of a feature quantity of a specific item such as food can be performed in a similar manner.

Furthermore, the image feature analyzing unit 3502 acquires a feature quantity stored in the image feature quantity storing unit 3503, compares the feature quantity with the feature quantity extracted earlier, and outputs a comparison result that a stored object appeared in the current acquired image data to the accidental ingestion determining unit 3501 when values of the feature quantities are the same or a difference between the values is sufficiently small. On the other hand, when a difference between the feature quantities is not sufficiently small, the image feature analyzing unit 3502 outputs a comparison result that the stored object did not appear to the accidental ingestion determining unit 3501. As a specific method of comparing feature quantities, for example, a method can be adopted in which a distance between feature quantities that are comparison objects is calculated and a determination is made as to whether the calculation result is a value equal to or smaller than a specified value (a value small enough to enable the objects to be considered the same).

Moreover, when feature quantities are expressed by vectors, a method may be adopted in which a Euclidean distance between vectors is calculated as a distance between feature quantities. In addition, when feature quantities are expressed by scalars, a method may be adopted in which a difference absolute value between the feature quantities is calculated as a distance between feature quantities. However, the method of calculating a distance between feature quantities is not limited to these methods.

FIG. 36 is a diagram showing an example of an image feature quantity table that is stored in the image feature quantity storing unit 3503. As shown in FIG. 36, the image feature quantity table stores a feature quantity 3602 of an object registered in advance, a type 3603 (in this example, a "person" or "food") of the registered object, and a name 3604 of the object in association with an automatically assigned feature quantity ID 3601. As an operation for object registration, it is assumed that the owner captures an image of himself/herself, an image of a face of a family member, or an image of food (feed or a treat) that can be fed to the animal prior to the start of use of the accidental ingestion detecting system according to the present embodiment.

Figure 37:
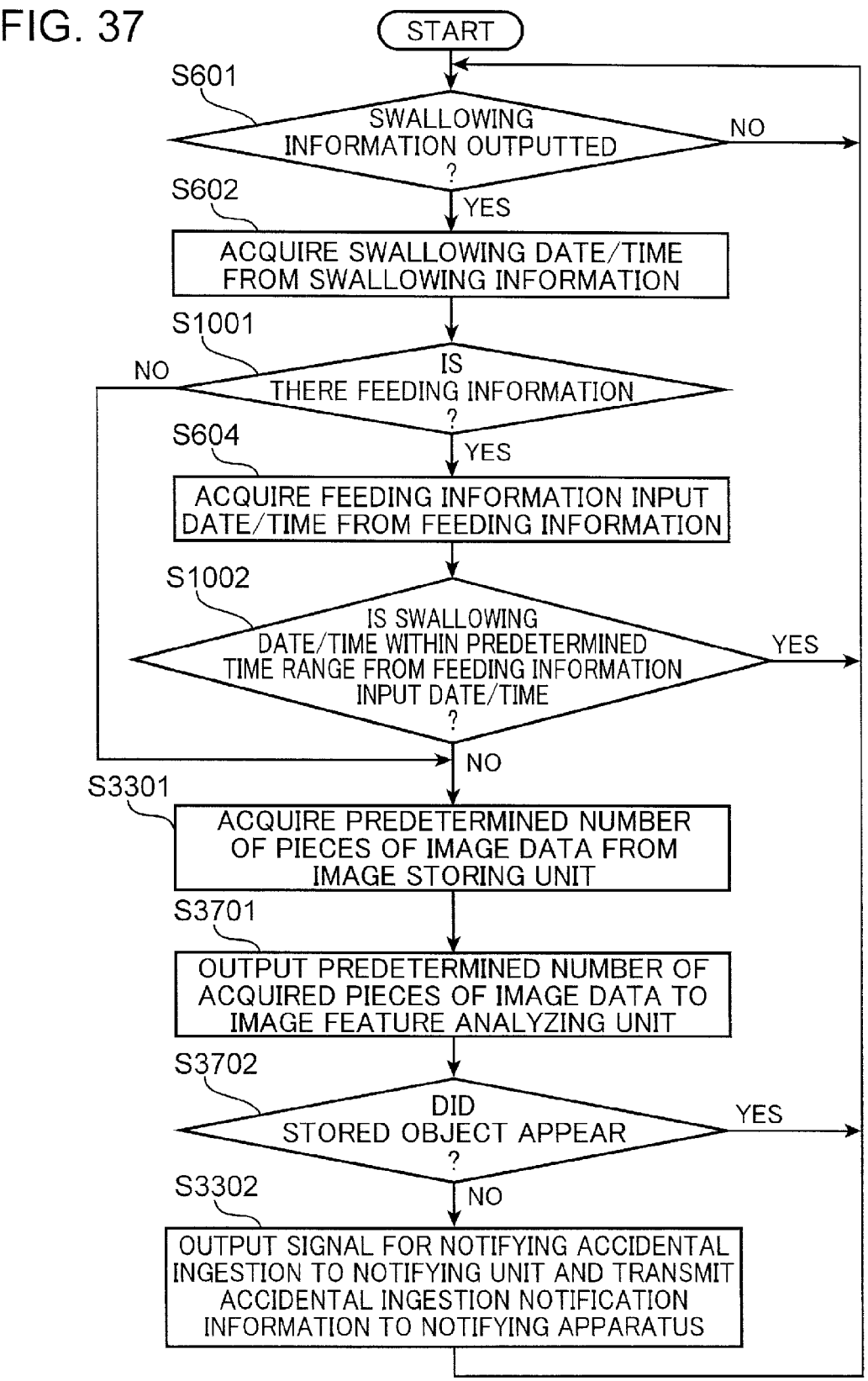
FIG. 37 is a flow chart showing an example of an operation of an accidental ingestion determining unit according to Embodiment 8.

FIG. 37 is a flow chart showing an example of an operation of the accidental ingestion determining unit 3501. Since steps other than S3701 and S3702 are the same as operations in the respective steps in FIG. 33 that shows operations according to Embodiment 7, a description thereof will be omitted.

Upon acquiring a predetermined number of pieces of image data from the image storing unit 3102 in S3301, the accidental ingestion determining unit 3501 outputs the acquired image data to the image feature analyzing unit 3502 (S3701). In addition, the accidental ingestion determining unit 3501 awaits transmission of a comparison result between a feature quantity extracted from the image data and a feature quantity stored in the image feature quantity storing unit 3503 from the image feature analyzing unit 3502. Upon receiving a comparison result from the image feature analyzing unit 3502 (S3701), the accidental ingestion determining unit 3501 checks the comparison result (S3702), and determines whether or not a stored object had appeared in the currently acquired image data. When a stored object had appeared in the currently acquired image data (Yes in S3702), the accidental ingestion determining unit 3501 makes a determination of "not accidental ingestion" and returns processing to monitoring (S601) of swallowing information. When a stored object had not appeared in the currently acquired image data (No in S3702), the accidental ingestion determining unit 3501 makes a determination of "accidental ingestion". Next, the accidental ingestion determining unit 3501 generates accidental ingestion notification information 3201 based on information on a date/time of detection of swallowing and the image data acquired in S3301 and transmits the accidental ingestion notification information 3201 to the notifying apparatus 702 and, at the same time, outputs a signal for notifying accidental ingestion to the notifying unit 305 (S3302).

As shown, in addition to the configuration described in Embodiment 7, the accidental ingestion detecting system according to Embodiment 8 further includes an image feature analyzing unit 3502 which analyzes image data to extract a feature quantity and compares the feature quantity with an image feature quantity that is stored in an image feature quantity storing unit 3503, and the image feature quantity storing unit 3503 that stores image feature quantities. When swallowing by an animal is detected by a swallowing detecting unit 302, a date/time of the occurrence of the swallowing is compared with a date/time included in feeding information which is inputted using a feeding information inputting apparatus 701. When the date/times are within a predetermined time range, the detected swallowing is determined not to be accidental ingestion. On the other hand, when the date/times are not within a predetermined time range, a determination is made that there is a possibility of accidental ingestion, a predetermined number of pieces of image data in a reverse chronological order is acquired from image data stored in the image storing unit 3102, the image data is subjected to image analysis, and a feature quantity included in the image data is extracted. In addition, the feature quantity obtained by the analysis and a feature quantity stored in advance in the image feature quantity storing unit 3503 are compared with each other, and when the currently obtained feature quantity is equal to or differs only slightly from any of the feature quantities stored in the image feature quantity storing unit 3503, the detected swallowing is determined not to be accidental ingestion. On the other hand, when the difference between the feature quantity obtained by the analysis and any of the feature quantities stored the image feature quantity storing unit 3503 is not sufficiently small, the detected swallowing is determined to be accidental ingestion and the occurrence of accidental ingestion by the animal is notified to the owner through the notifying unit 305 of the accidental ingestion detecting apparatus 3500 and the notifying apparatus 702. Therefore, an accidental ingestion notification can be prevented from being needlessly made to the owner.

Figure 38:
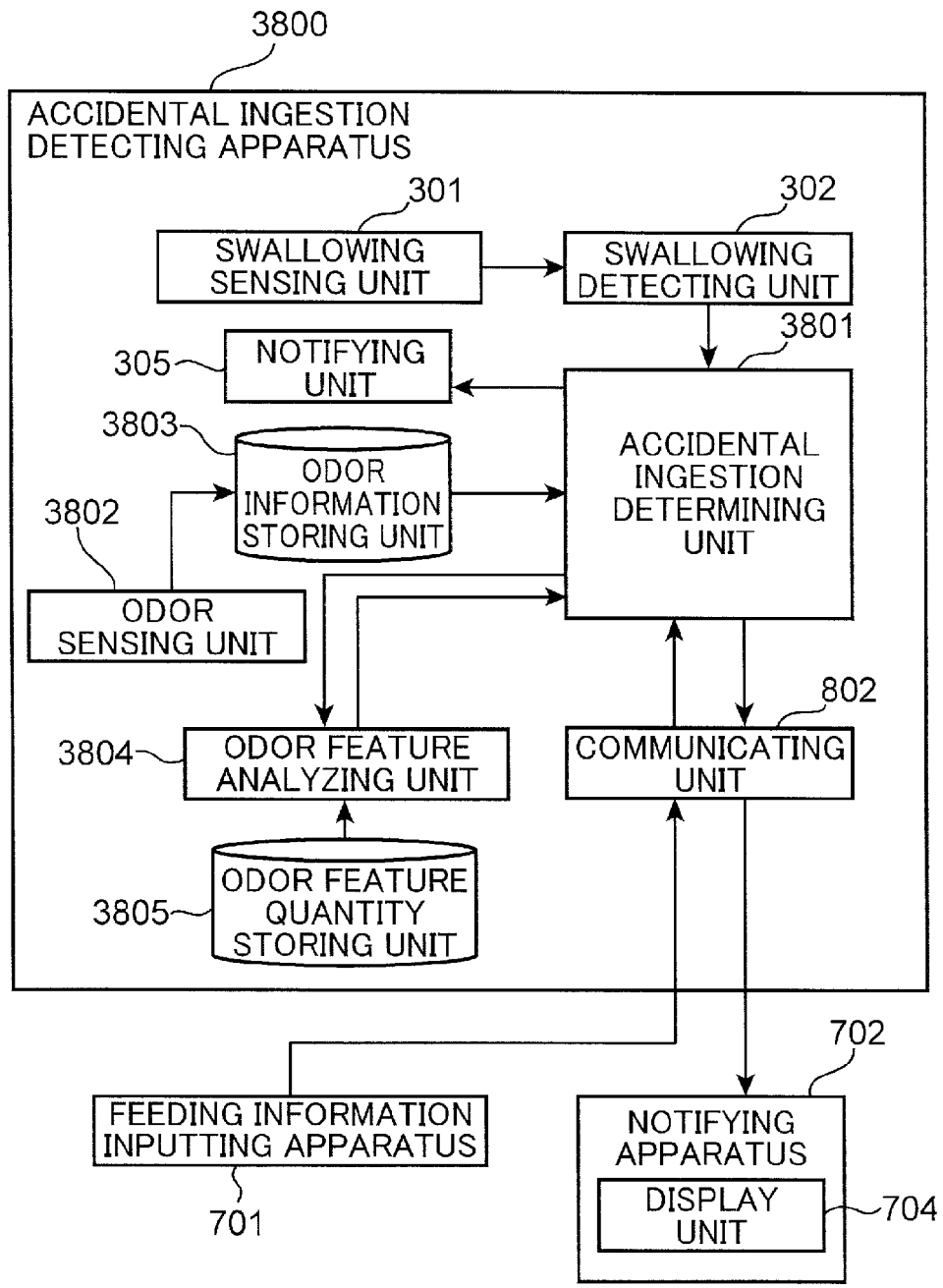
FIG. 38 is a block diagram showing a functional configuration of a modification of the accidental ingestion detecting system according to Embodiment 8.

Moreover, while an image feature quantity of an object registered in advance is used for determination of accidental ingestion in the accidental ingestion detecting system according to the present embodiment, a feature quantity of odor information may be used instead of an image feature quantity. FIG. 38 is a block diagram showing a functional configuration of a modification of the accidental ingestion detecting system according to Embodiment 8.

For example, an accidental ingestion detecting apparatus 3800 shown in FIG. 38 includes an odor sensing unit 3802, an odor information storing unit 3803, an odor feature analyzing unit 3804, and an odor feature quantity storing unit 3805 in place of the imaging unit 3001, the image storing unit 3102, the image feature analyzing unit 3502, and the image feature quantity storing unit 3503 of the accidental ingestion detecting apparatus 3500 according to the present embodiment.

The odor sensing unit 3802 measures an odor in a vicinity of the accidental ingestion detecting apparatus 3800. In this case, for example, the odor sensing unit 3802 detects a concentration of one or more odor component contained in air in the vicinity of the accidental ingestion detecting apparatus 3800 and outputs the concentration to the odor information storing unit 3803. Moreover, for example, the odor sensing unit 3802 detects odor information periodically (for example, 1 second). Upon receiving the outputted odor information, the odor information storing unit 3803 stores the odor information in an internal storage area. In this case, an upper limit of the number of pieces of odor information to be stored is set to a predetermined number, and when new odor information is inputted after the number of pieces of odor information has reached the upper limit, the odor information storing unit 3803 deletes the oldest odor information.

When the accidental ingestion determining unit 3801 determines, similarly to the accidental ingestion determining unit 3501, that there is a possibility of accidental ingestion, the accidental ingestion determining unit 3801 acquires a predetermined number of pieces of odor information in a reverse chronological order from odor information stored in the odor information storing unit 3803 and outputs the odor information to the odor feature analyzing unit 3804. The odor feature analyzing unit 3804 extracts a feature quantity of the odor information by analyzing the odor information. In addition, the odor feature analyzing unit 3804 compares the feature quantity obtained as a result of the analysis with a feature quantity stored in advance in the odor feature quantity storing unit 3805 and outputs a comparison result regarding whether or not accidental ingestion had occurred to the accidental ingestion determining unit 3801.

In this case, when a currently obtained feature quantity is equal to or only differs slightly from any of the feature quantities stored in the odor feature quantity storing unit 3805, the accidental ingestion determining unit 3801 determines that the detected swallowing is not accidental ingestion. On the other hand, when comparison result is received to the effect that a difference between feature quantities is not sufficiently small, the accidental ingestion determining unit 3801 determines that the detected swallowing is accidental ingestion. Subsequently, when the accidental ingestion determining unit 3801 makes a determination of accidental ingestion, the accidental ingestion determining unit 3801 notifies the owner that an accidental ingestion by the animal has occurred through the notifying unit 305 of the accidental ingestion detecting apparatus 3800 and the notifying apparatus 702.

Moreover, the odor feature analyzing unit 3804 may extract a feature quantity of odor information using a classifier such as SVM and AdaBoost described earlier. In addition, the odor feature analyzing unit 3804 may compare an extracted feature quantity with a feature quantity stored in the odor feature quantity storing unit 3805 using a method similar to that used by the image feature analyzing unit 3502.

The odor feature quantity storing unit 3805 stores feature quantities of predetermined odors. In this case, for example, feature quantities of one or more pieces of odor information representing an odor of food that is given to the animal or an odor of the owner are stored in the odor feature quantity storing unit 3805. A data configuration of the odor feature quantity storing unit 3805 is similar to the data configuration of the image feature quantity storing unit 3503.

As shown, the accidental ingestion detecting apparatus 3800 analyzes odor information of a period from a time point of detection of swallowing to a time point slightly prior thereto, and if analyzed odor information is odor information representing an odor that is similar to an odor of food or an odor of the owner which is registered in advance, a determination of accidental ingestion is not made. Therefore, an accidental ingestion notification is prevented from being needlessly made to the owner. Therefore, the accidental ingestion detecting system shown in FIG. 38 can achieve the same object as the accidental ingestion detecting system shown in FIG. 35.

While the accidental ingestion detecting apparatus and the accidental ingestion detecting system according to the present invention have been described based on embodiments thereof, the present invention is not limited to these embodiments. It is to be understood that various modifications to the present embodiment as will occur to those skilled in the art and forms constructed by combining components of different embodiments may be made without departing from the spirit of the present invention, and that such modifications and forms are to be included in the scope of the present invention.

Figure 39:
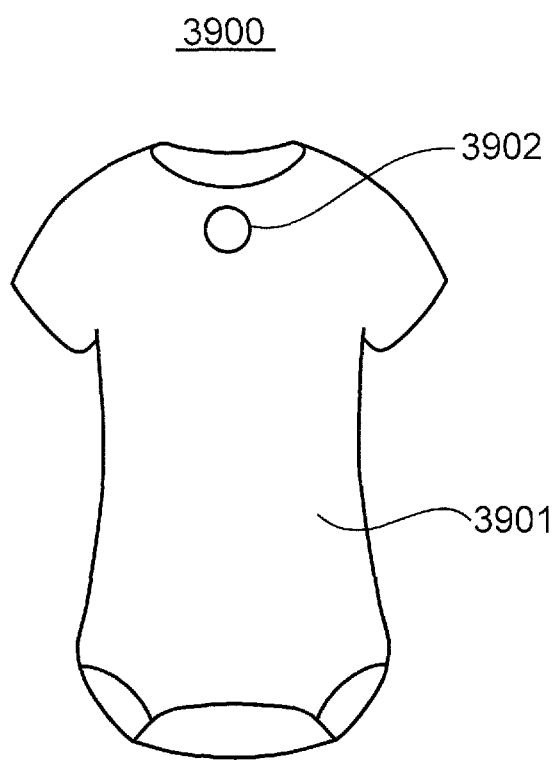
FIG. 39 is a diagram showing an appearance configuration of an accidental ingestion detecting apparatus when an infant is adopted as an animal.

Moreover, all of the embodiments have been described on the premise that a pet is primarily assumed as the animal and the accidental ingestion detecting apparatus and the accidental ingestion detecting system detect accidental ingestion by the pet. However, this is simply an example and the present embodiment can also be applied to animals other than pets such as humans (in particular, infants). FIG. 39 is a diagram showing an appearance configuration of an accidental ingestion detecting apparatus 3900 when an infant is adopted as an animal. In the accidental ingestion detecting apparatus 3900 shown in FIG. 39, a shirt-type main body unit 3901 is adopted in place of the collar-type main body unit 101. In this case, the main body unit 3901 is constituted by, for example, a shirt such as rompers that is worn by an infant as everyday underwear.

A sound pickup sensor 3902 for collecting sounds in the body is attached to the main body unit 3901. In this case, for example, the sound pickup sensor 3902 is attached to a position that comes into close contact with at least any of a neck area, a chest area, and an abdomen area of the person wearing the main body unit 3901. In the example shown in FIG. 39, the sound pickup sensor 3902 is attached to the main body unit 3901 so as to be positioned in a chest area of an infant.

Moreover, when adopting the mode shown in FIG. 39, for example, the CPU 201, the ROM 202, the RAM 203, the inputting apparatus 103, and the display apparatus 104 shown in FIG. 2 may be consolidated into a single chip and attached to the main body unit 3901. In this case, communication circuits of a wireless LAN, Bluetooth (registered trademark), or the like may be provided in a chip unit configured as a single chip and the sound pickup sensor 3902 to be connected to one another so as to be capable of communication, or the sound pickup sensor 3902 may be provided in the chip unit.

Alternatively, only the sound pickup sensor 3902 may be attached to the main body unit 3901 and the CPU 201, the ROM 202, the inputting apparatus 103, and the display apparatus 104 may be built into the notifying apparatus 702 that is a mobile terminal owned by a parent or guardian. In this case, for example, the swallowing detecting unit 302, the accidental ingestion determining unit 801, the notifying unit 305, and the communicating unit 802 may be mounted to the notifying apparatus 702 in FIG. 8.

In addition, while the accidental ingestion detecting apparatuses according to Embodiments 2 to 8 include a swallowing sensing unit, a swallowing detecting unit, a notifying unit, an accidental ingestion determining unit, a communicating unit, and various other functional blocks, the functional blocks other than the swallowing sensing unit and the communicating unit may be realized by a different device (such as a home server or a server on the Internet) that is separate from the main body of the accidental ingestion detecting apparatus.

Furthermore, the notifying unit 305 included in the accidental ingestion detecting apparatuses according to Embodiments 2 to 8 and the notifying apparatus that is independent of the accidental ingestion detecting apparatuses may notify accidental ingestion using any one of light, sound, text, and image display or a combination thereof.

The present disclosure is useful for an apparatus, a system, and a method for detecting accidental ingestion by animals.

This application is based on Japanese Patent application No. 2013-085346 filed in Japan Patent Office on Apr. 16, 2013, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An accidental ingestion detecting apparatus comprising:
a swallowing sensing unit which senses swallowing by an animal;
a swallowing detecting unit which detects swallowing based on sensing data outputted by the swallowing sensing unit and which outputs swallowing information that is information related to the swallowing;
a feeding information inputting unit which accepts input of information related to feeding of the animal and which outputs the information as feeding information; and
an accidental ingestion determining unit which determines accidental ingestion by the animal, wherein
the accidental ingestion determining unit determines:
accidental ingestion by the animal has not occurred when a swallowing date/time indicated by date/time information included in the swallowing information is within a predetermined time range from a feeding information input date/time indicated by date/time information included in the feeding information; and
accidental ingestion by the animal has occurred when the swallowing date/time is not within the predetermined time range.

2. The accidental ingestion detecting apparatus according to claim 1, further comprising
a notifying unit which notifies a user that accidental ingestion by the animal has occurred when the accidental ingestion determining unit determines that accidental ingestion by the animal has occurred.

3. The accidental ingestion detecting apparatus according to claim 2, wherein
the notifying unit issues a notification using at least one of light, sound, text, and an image.

4. The accidental ingestion detecting apparatus according to claim 1, wherein
the swallowing sensing unit is a sound pickup sensor which is mounted to a neck area of the animal and which picks up sound generated in the throat during swallowing, and
the swallowing detecting unit detects swallowing by performing a frequency analysis on sound signal data that is outputted from the sound pickup sensor.

5. The accidental ingestion detecting apparatus according to claim 1, wherein
the swallowing sensing unit is a sound pickup sensor which is mounted to at least one of a chest area and an abdomen area of the animal and which picks up sound generated in at least one of an esophagus and a stomach during swallowing, and
the swallowing detecting unit detects swallowing by performing a frequency analysis on sound signal data that is outputted from the sound pickup sensor.

6. An accidental ingestion detecting system comprising an accidental ingestion detecting apparatus that detects accidental ingestion by an animal and a feeding information inputting apparatus that accepts information related to feeding of the animal and that outputs the information as feeding information, wherein
the accidental ingestion detecting apparatus includes:
a swallowing sensing unit which senses swallowing by an animal;
a swallowing detecting unit which detects swallowing based on sensing data outputted by the swallowing sensing unit and which outputs first swallowing information that is information related to the swallowing;
an accidental ingestion determining unit which determines accidental ingestion by the animal; and
a communicating unit which performs communication with the feeding information inputting apparatus, and
the accidental ingestion determining unit determines that:
accidental ingestion by the animal has not occurred when a swallowing date/time indicated by date/time information included in the first swallowing information is within a predetermined time range from a feeding information input date/time indicated by date/time information included in the feeding information; and the accidental ingestion by the animal has occurred when the swallowing date/time is not within the predetermined time range.

7. The accidental ingestion detecting apparatus according to claim 6, further comprising
a first notifying unit which notifies a user that accidental ingestion by the animal has occurred when the accidental ingestion determining unit determines that accidental ingestion by the animal has occurred.

8. The accidental ingestion detecting system according to claim 7, further comprising
a second notifying unit which is independent of the accidental ingestion detecting apparatus and which communicates with a communicating unit included in the accidental ingestion detecting apparatus and notifies the user that accidental ingestion by the animal has occurred when the accidental ingestion determining unit determines that accidental ingestion by the animal has occurred, wherein
the first notifying unit and the second notifying unit issue a notification using at least one of light, sound, text, and an image.

9. The accidental ingestion detecting system according to claim 6, further comprising
a second notifying unit that is independent of the accidental ingestion detecting apparatus, wherein
when the accidental ingestion determining unit determines that accidental ingestion by the animal has occurred, the second notifying unit communicates with a communicating unit included in the accidental ingestion detecting apparatus and notifies a user that accidental ingestion by the animal has occurred.

10. An accidental ingestion detecting system comprising an accidental ingestion detecting apparatus that detects accidental ingestion by an animal and a feeding information inputting apparatus that accepts information related to feeding of the animal and that outputs the information as feeding information, wherein
the accidental ingestion detecting apparatus includes:
a swallowing sensing unit which senses swallowing by an animal;
a swallowing detecting unit which detects swallowing based on sensing data outputted by the swallowing sensing unit and which outputs first swallowing information that is information related to the swallowing;
a communicating unit which performs communication with the feeding information inputting apparatus;
an accidental ingestion determining unit which determines accidental ingestion by the animal based on date/time information included in the first swallowing information and date/time information included in feeding information, which is inputted using the feeding information inputting apparatus and which is included in feeding information obtained through the communicating unit; and
a first notifying unit which notifies a user that accidental ingestion by the animal has occurred when the accidental ingestion determining unit determines that accidental ingestion by the animal has occurred;
the accidental ingestion detecting system further comprising:
a second notifying unit which is independent of the accidental ingestion detecting apparatus and which communicates with a communicating unit included in the accidental ingestion detecting apparatus and notifies the user that accidental ingestion by the animal has occurred when the accidental ingestion determining unit determines that accidental ingestion by the animal has occurred; and
a confirmation inputting unit to which is inputted a confirmation result by the user indicating whether or not the swallowing reported by the accidental ingestion notification that is notified by at least one of the first notifying unit and the second notifying unit is accidental ingestion.

11. The accidental ingestion detecting system according to claim 10, further comprising
a confirmation result storing unit which stores confirmation result information, in which the confirmation result inputted using the confirmation inputting unit and second swallowing information including date/time information of swallowing indicated by the accidental ingestion notification to which the confirmation result had been inputted are associated with each other, wherein
the accidental ingestion determining unit determines,
in a case where a first swallowing date/time indicated by the first swallowing information is not within a predetermined first time range with respect to a feeding date/time indicated by the feeding information,
that the swallowing indicated by the first swallowing information is not accidental ingestion when confirmation result information indicating that the swallowing is not accidental ingestion is stored in the confirmation result storing unit within a predetermined second time range with respect to the first swallowing date/time.

12. The accidental ingestion detecting system according to claim 10, further comprising:
a location positioning unit which measures a position of the accidental ingestion detecting apparatus and which outputs positioning data; and
a confirmation result storing unit which stores confirmation result information, in which the confirmation result inputted using the confirmation inputting unit and second swallowing information including a position of the accidental ingestion detecting apparatus upon input of the confirmation result are associated with each other, wherein
the first swallowing information includes a first swallowing date/time indicating a date/time of swallowing and first location information indicating a location where the swallowing had occurred, and
the accidental ingestion determining unit determines that in a case where the first swallowing date/time is not within a predetermined first time range with respect to a feeding date/time indicated by the feeding information,
the swallowing indicated by the first swallowing information is not accidental ingestion when confirmation result information indicating that the swallowing is not accidental ingestion is stored in the confirmation result storing unit within a predetermined distance range with respect to the first location information.

13. The accidental ingestion detecting system according to claim 10, further comprising:
a location positioning unit which measures a position of the accidental ingestion detecting apparatus and which outputs positioning data;
a position monitoring unit which monitors the position of the accidental ingestion detecting apparatus based on positioning data from the location positioning unit; and a confirmation result storing unit that stores confirmation result information, in which the confirmation result inputted using the confirmation inputting unit and second swallowing information including date/time information of swallowing and a position of the accidental ingestion detecting apparatus upon input of the confirmation result are association with each other, wherein when the position monitoring unit detects that the accidental ingestion detecting apparatus has entered a predetermined distance range from a confirmation result input position where a confirmation result that swallowing is accidental ingestion had been previously inputted, at least one of the first notifying unit and the second notifying unit notifies the user that the animal has approached a location where accidental ingestion by the animal had previously occurred.

14. The accidental ingestion detecting system according to claim 10, further comprising:

a location positioning unit which measures a position of the accidental ingestion detecting apparatus and which outputs positioning data; and a user location positioning unit which measures a position of the user and which outputs user positioning data, wherein the accidental ingestion determining unit determines accidental ingestion based on the positioning data outputted by the location positioning unit and the user positioning data outputted by the user location positioning unit at the time point of detection of swallowing.

15. The accidental ingestion detecting system according to claim 10, further comprising a distance measuring unit which measures a distance between the accidental ingestion detecting apparatus and the user and which outputs distance data, wherein the accidental ingestion determining unit determines accidental ingestion based on distance data outputted by the distance measuring unit at the time point of detection of swallowing.

16. An accidental ingestion detecting system comprising an accidental ingestion detecting apparatus that detects accidental ingestion by an animal and a feeding information inputting apparatus that accepts information related to feeding of the animal and that outputs the information as feeding information, wherein the accidental ingestion detecting apparatus includes:

a swallowing sensing unit which senses swallowing by an animal;

a swallowing detecting unit which detects swallowing based on sensing data outputted by the swallowing sensing unit and which outputs first swallowing information that is information related to the swallowing;

a communicating unit which performs communication with the feeding information inputting apparatus;

an accidental ingestion determining unit which determines accidental ingestion by the animal based on date/time information included in the first swallowing information and date/time information included in feeding information, which is inputted using the feeding information inputting apparatus and which is included in feeding information obtained through the communicating unit; and a first notifying unit which notifies a user that accidental ingestion by the animal has occurred when the accidental ingestion determining unit determines that accidental ingestion by the animal has occurred;

the accidental ingestion detecting system further comprising:

a second notifying unit which is independent of the accidental ingestion detecting apparatus and which communicates with a communicating unit included in the accidental ingestion detecting apparatus and notifies the user that accidental ingestion by the animal has occurred when the accidental ingestion determining unit determines that accidental ingestion by the animal has occurred;

an imaging unit which captures an image of a vicinity of the accidental ingestion detecting apparatus; and a captured image storing unit which stores an image captured by the imaging unit, wherein when the accidental ingestion determining unit determines that accidental ingestion by the animal has occurred, at least one of the first notifying unit and the second notifying unit includes an image which is stored in the captured image storing unit and which had been captured during a certain past time period since detection of the accidental ingestion in an accidental ingestion notification for notifying the user that accidental ingestion by the animal has occurred.

17. An accidental ingestion detecting system comprising an accidental ingestion detecting apparatus that detects accidental ingestion by an animal and a feeding information inputting apparatus that accepts information related to feeding of the animal and that outputs the information as feeding information, wherein the accidental ingestion detecting apparatus includes:

a swallowing sensing unit which senses swallowing by an animal;

a swallowing detecting unit which detects swallowing based on sensing data outputted by the swallowing sensing unit and which outputs first swallowing information that is information related to the swallowing;

a communicating unit which performs communication with the feeding information inputting apparatus; and an accidental ingestion determining unit which determines accidental ingestion by the animal based on date/time information included in the first swallowing information and date/time information included in feeding information, which is inputted using the feeding information inputting apparatus and which is included in feeding information obtained through the communicating unit;

the accidental ingestion detecting system further comprising:

an imaging unit that captures an image of a vicinity of the accidental ingestion detecting apparatus;

an image feature quantity storing unit that stores a feature quantity of a predetermined image in advance; and an image feature analyzing unit which analyzes an image captured by the imaging unit to extract a feature quantity and which compares the feature quantity with a feature quantity stored in the image feature quantity storing unit, wherein the accidental ingestion determining unit determines accidental ingestion based on the feature quantity of an image captured by the imaging unit from a predetermined period of time prior to a time point of detection of swallowing and a feature quantity of the predetermined image that is stored in the image feature quantity storing unit.

18. An accidental ingestion detecting system comprising an accidental ingestion detecting apparatus that detects accidental ingestion by an animal and a feeding information inputting apparatus that accepts information related to feeding of the animal and that outputs the information as feeding information, wherein the accidental ingestion detecting apparatus includes:
a swallowing sensing unit which senses swallowing by an animal;
a swallowing detecting unit which detects swallowing based on sensing data outputted by the swallowing sensing unit and which outputs first swallowing information that is information related to the swallowing;
a communicating unit which performs communication with the feeding information inputting apparatus; and
an accidental ingestion determining unit which determines accidental ingestion by the animal based on date/time information included in the first swallowing information and date/time information included in feeding information, which is inputted using the feeding information inputting apparatus and which is included in feeding information obtained through the communicating unit;
the accidental ingestion detecting system further comprising:
an odor sensing unit that measures an odor in a vicinity of the accidental ingestion detecting apparatus;
an odor feature quantity storing unit that stores a feature quantity of a predetermined odor in advance; and
an odor feature analyzing unit which analyzes odor data obtained from the odor sensing unit to extract a feature quantity and compare the feature quantity with the feature quantity stored in the odor feature quantity storing unit, wherein
the accidental ingestion determining unit determines accidental ingestion based on the feature quantity of an odor measured by the odor sensing unit from a predetermined period of time prior to a time point of detection of swallowing and a feature quantity of the predetermined odor that is stored in the odor feature quantity storing unit.

19. An accidental ingestion detecting method of an accidental ingestion detecting system including an accidental ingestion detecting apparatus and a feeding information inputting apparatus, the accidental ingestion detecting method comprising:
sensing swallowing by an animal;
detecting swallowing based on the sensing data and outputting swallowing information that is information related to the swallowing;
accepting input of information related to feeding of the animal and outputting the information as feeding information; and
determining accidental ingestion by the animal, wherein
in the determination, it is determined that: accidental ingestion by the animal has not occurred when a swallowing date/time indicated by date/time information included in the swallowing information is within a predetermined time range from a feeding information input date/time indicated by date/time information included in the feeding information; and the accidental ingestion by the animal has occurred when the swallowing date/time is not within the predetermined time range.

20. A computer-readable storage medium storing a program that causes a computer to execute the accidental ingestion detecting method according to claim 19.

* * * * *